US012427106B2

(12) United States Patent
Xia et al.

(10) Patent No.: US 12,427,106 B2
(45) Date of Patent: Sep. 30, 2025

(54) ELASTIC SHEET WITH FUNCTION OF RE-ACTIVATING ENDOMETRIAL BASAL LAYER IN UTERINE CAVITY AND FORMING METHOD THEREOF

(71) Applicant: YIPURUN (SHANGHAI) BIOTECHNOLOGY CO., LTD., Shanghai (CN)

(72) Inventors: Peipei Xia, Shanghai (CN); Zheng Wei, Shanghai (CN); Wei Yan, Shanghai (CN); Rui Yang, Shanghai (CN)

(73) Assignee: YIPURUN (SHANGHAI) BIOTECHNOLOGY CO., LTD., Shanghai (CN)

( * ) Notice: Subject to any disclaimer, the term of this patent is extended or adjusted under 35 U.S.C. 154(b) by 1346 days.

(21) Appl. No.: 16/445,939

(22) Filed: Jun. 19, 2019

(65) Prior Publication Data
US 2019/0328659 A1    Oct. 31, 2019

(30) Foreign Application Priority Data
Apr. 19, 2018   (CN) .......................... 201810354277.2
Mar. 29, 2019   (CN) .......................... 201910252398.0

(51) Int. Cl.
*A61K 9/00*       (2006.01)
*A61K 31/565*    (2006.01)
(Continued)

(52) U.S. Cl.
CPC .......... *A61K 9/0039* (2013.01); *A61K 31/565* (2013.01); *A61K 47/32* (2013.01);
(Continued)

(58) Field of Classification Search
CPC ........ A61M 31/002; A61M 2210/1433; A61M 31/00; A61M 2205/0216;
(Continued)

(56) References Cited

U.S. PATENT DOCUMENTS 3,516,403 A * 6/1970 Cournut .................... A61F 6/18
                                                                    604/285
3,913,573 A * 10/1975 Gutnick ................. A61F 6/144
                                                                    128/833

(Continued)

FOREIGN PATENT DOCUMENTS

CN          103566462 A  *  2/2014
EP          3446664 A1  *  2/2019

OTHER PUBLICATIONS

Kwang, Effects of estrogen on the vascular wall: vasomotor function and inflammation, 2002, Eldevier, 55, 714-726 (Year: 2002).*

*Primary Examiner* — Chelsea E Stinson
*Assistant Examiner* — Hamza A Darb
(74) *Attorney, Agent, or Firm* — Dickinson Wright PLLC

(57) ABSTRACT

An elastic sheet for re-activating an endometrial basal layer in a uterine cavity comprises a silicone rubber and a drug, wherein the drug is encased inside the silicone rubber in the manner of a drug storage zone, or uniformly dispersed inside the silicone rubber, or carried by an outer surface of the silicone rubber as a coating, and the drug comprises an estrogen. A method for forming the elastic sheet with a drug in a matrix-type elastic sheet; or as a sustained release coating is provided. The estrogen is loaded on the silicone rubber, and thus the endometrial basal layer is continuously activated through drug stimulation, allowing for the endometrial basal layer to re-proliferate the functional layers, thereby restoring the normal endometrial structure and completely preventing adhesions.

16 Claims, 41 Drawing Sheets

(51) Int. Cl.
*A61K 47/32* (2006.01)
*A61M 31/00* (2006.01)
*B29B 7/90* (2006.01)
*B29C 48/00* (2019.01)
*B29C 48/07* (2019.01)
B29K 83/00 (2006.01)
B29K 105/00 (2006.01)
B29K 509/02 (2006.01)
B29L 7/00 (2006.01)

(52) U.S. Cl.
CPC ............... *A61M 31/00* (2013.01); *B29B 7/90* (2013.01); *B29C 48/022* (2019.02); *B29C 48/07* (2019.02); *A61M 2205/0216* (2013.01); *A61M 2210/1433* (2013.01); *B29K 2083/00* (2013.01); *B29K 2105/0035* (2013.01); *B29K 2509/02* (2013.01); *B29L 2007/002* (2013.01)

(58) Field of Classification Search
CPC .. A61M 2210/1425; A61M 2210/1475; A61K 9/0039; A61K 31/565; A61K 47/32; B29B 7/90; B29C 48/022; B29C 48/07; B29K 2083/00; B29K 2105/0035; B29K 2509/02; B29L 2007/002; A61F 2002/0072; A61F 6/142; A61F 2002/9511; A61F 6/148; A61F 6/18
See application file for complete search history.

(56) References Cited

U.S. PATENT DOCUMENTS

| | | | | |
|---|---|---|---|---|
| 4,585,451 | A | * | 4/1986 | Millar ................. A61K 9/0036 424/432 |
| 2002/0161352 | A1 | * | 10/2002 | Lin .......................... A61F 6/08 604/515 |
| 2006/0264912 | A1 | * | 11/2006 | McIntyre ............. A61K 9/0036 604/8 |
| 2015/0202076 | A1 | * | 7/2015 | Wijzen ..................... A61F 6/18 128/833 |
| 2017/0319833 | A1 | * | 11/2017 | Shaked ..................... A61F 6/14 |
| 2017/0340476 | A1 | * | 11/2017 | Kuster ............... A61B 5/14503 |
| 2019/0167575 | A1 | * | 6/2019 | Gazvani ............. A61K 9/0039 |

* cited by examiner

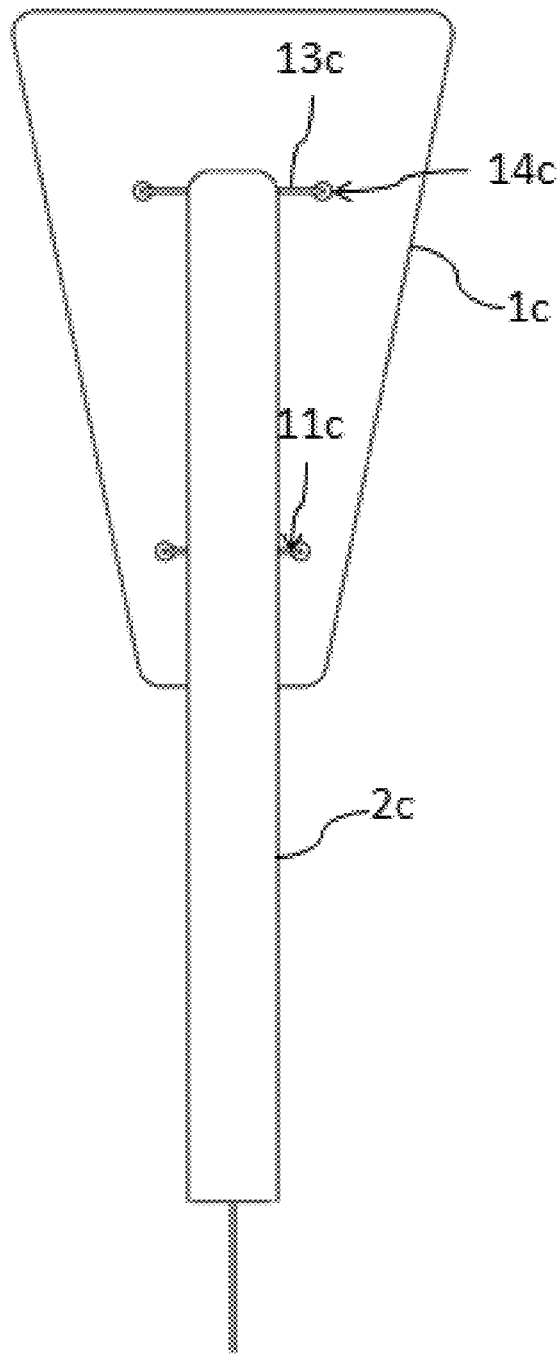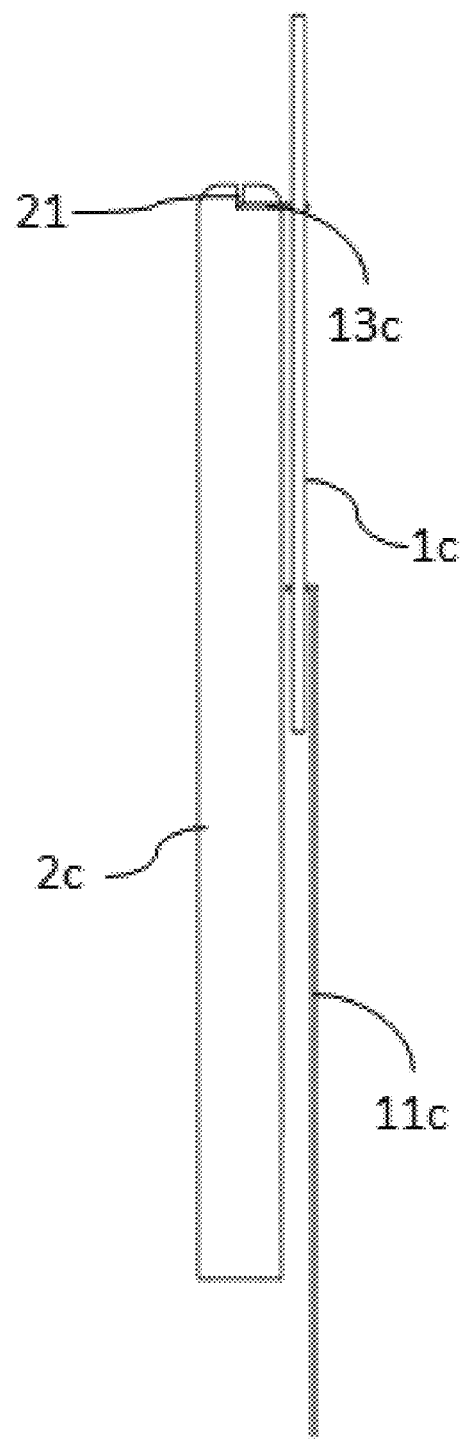
FIG. 3
FIG. 4

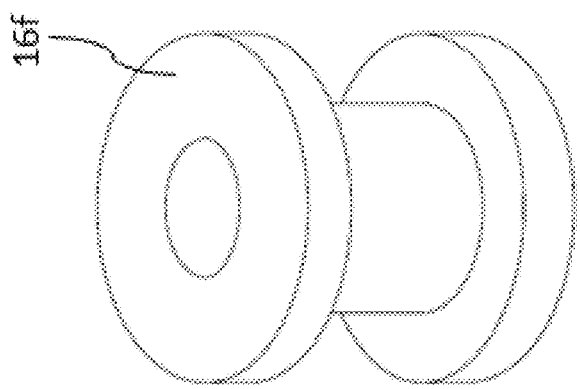
FIG. 8
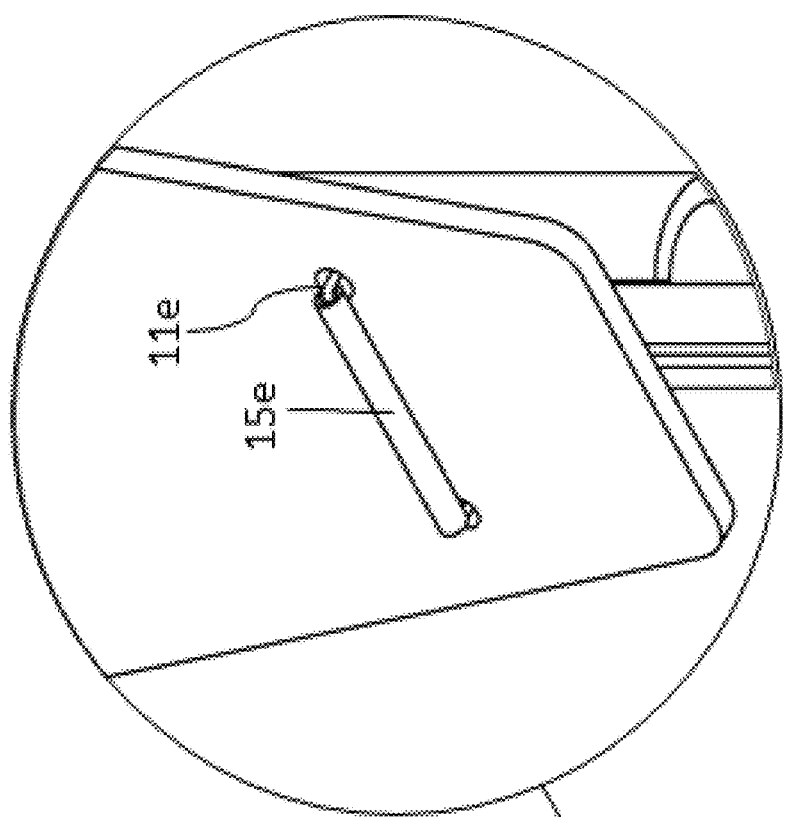
FIG. 7
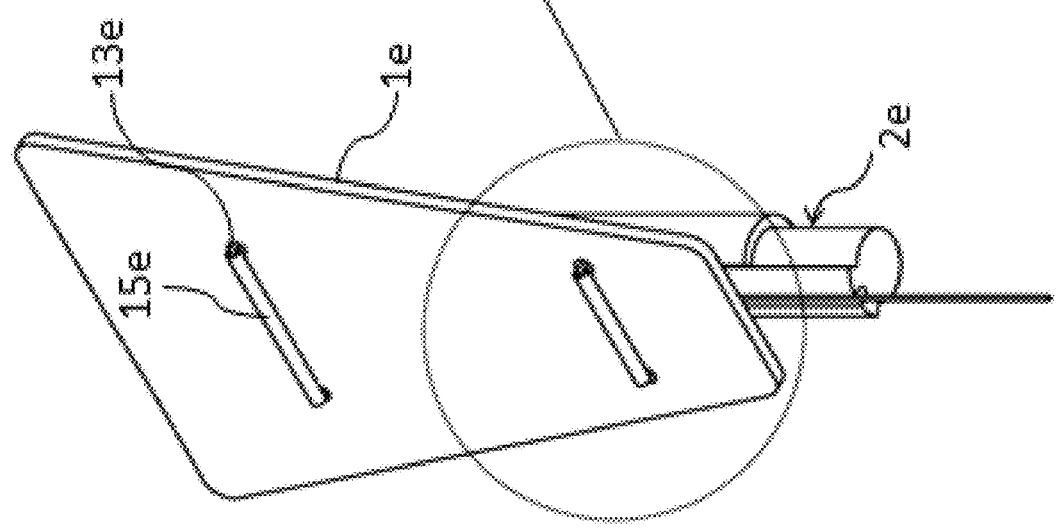

ELASTIC SHEET WITH FUNCTION OF RE-ACTIVATING ENDOMETRIAL BASAL LAYER IN UTERINE CAVITY AND FORMING METHOD THEREOF

CROSS REFERENCE TO RELATED APPLICATIONS

This U.S. utility patent application claims the benefit of Chinese patent application No. CN 2018 1 0354277.2, filed Apr. 19, 2018, and Chinese patent application CN 2019 1 0252398.0, filed Mar. 29, 2019, and Chinese patent application CN 2019 1 0270137.1, filed Mar. 29, 2019, and Chinese patent application CN 2019 1 0270119.3, filed Mar. 29, 2019, and Chinese patent application CN 2019 1 0270128.2, filed Mar. 29, 2019, the contents of which are incorporated herein by reference in their entirety.

BACKGROUND OF THE INVENTION

1. Field of the Invention

The present disclosure relates generally to medical instruments, and more particularly to an elastic sheet. Specifically, the present disclosure relates to elastic sheets for use in uteri, and more particularly to an elastic sheet with a function of re-activating an endometrial basal layer in a uterine cavity and a forming method thereof.

2. Related Art

The uterus is the organ where menstruation takes place and fetus is conceived. It is located at the center of the pelvic cavity and is exclusive to the female body. The size of the uterus is related to age and fertility. For women who have not given birth, it is about 7.5 cm long, 5 cm wide and 3 cm thick. The uterus can be divided into three parts, namely a bottom part, a body part and a neck part. The uterine cavity has an inverted triangle shape about 6 cm deep. The two upper corners are called as "uterine horns" leading to the fallopian tubes. The lower end is narrowed to an "isthmus" about 1 cm long.

Various uterine diseases can be caused by abortion, contraceptive device implantation and removal, surgery and other intrauterine operation, as well as infection, etc. Uterine disease is one of the most common diseases for females, whose normal life and health, including the ability to become pregnant would be seriously affected. Such diseases comprise endometritis, endometriosis, uterine hypertrophies, uterine polyps, uterine fibroids, uterine cysts, uterine prolapse, endometrial cancers, etc.

The therapeutic effects of drug treatments on the above-mentioned diseases is limited. With the rapid development of minimally invasive surgery, diagnosis and surgery under hysteroscopy have been widely used in gynecological treatment. Due to a series of advantages such as fewer traumas and less intraoperative bleeding, hysteroscopy becomes an important device of minimally invasive surgery.

However, the surgery still involves damages to the uterine cavity. Operations such as the separation of polyps, fibroids, cysts and adhesions, and curettages, etc. may cause damage to the endometrial basal layer, leading to endometrial fibrosis and intrauterine adhesions.

Muscle is a main component of the uterus. The anterior and posterior walls of the uterine body are almost in contact with each other, and the uterine cavity therebetween is only a crack. The walls of the uterine body consist of three layers of tissue, namely a serosal layer, a muscular layer and a mucosal layer. The mucosal layer is the endometrial layer (i.e., endometrium), which also can be divided into three layers, namely a dense layer, a sponge layer and a basal layer. The dense layer and the sponge layer are the proliferating zones regenerated by the basal layer, which are collectively called as a functional layer. It is sensitive to sex hormones and periodically changes under the influence of ovarian hormones. The functional layer will be eventually detached at each periodicity with the uterine bleeding if there is no pregnancy. Clinical manifestation is in menstrual period. The basal layer is tightly close to the muscular layer and is not sensitive to ovarian hormones, with no periodic changes. Normal endometrial glands secrete a thin alkaline fluid to keep the uterine cavity moist. Therefore, the normal anterior and posterior walls of the uterus are close to each other but do not adhere and grow together.

After intrauterine surgery, the intrauterine adhesions may form when the endometrial basal layer is damaged, in particular when the corresponding positions of the anterior and posterior walls are damaged simultaneously. It is currently agreed that the trauma to the pregnant uterus is the main cause of intrauterine adhesions. Trauma often occurs in 1-4 weeks after postpartum or abortion due to curettage from excessive bleeding. During this susceptibility period, any trauma can cause the detachment of endometrial basal layer, resulting in permanent adhesions, uterine deformations and disappearance of uterine symmetry. Secondly, trauma to non-pregnant endometrium also can cause intrauterine adhesions. It has been reported that intrauterine adhesions can occur after diagnostic curettage, transabdominal myomectomy, cervical biopsy, endometrial polyp removal, intrauterine contraceptive implantation, or radiation therapy. In addition, intrauterine adhesions can also occur after various hysteroscopic surgeries, such as myomectomy and uterine mediastinotomy under hysteroscopy, etc.

After minimally invasive surgery, damage to the uterine cavity can create a high probability of adhesions between the corresponding wound surfaces. Intrauterine adhesions can prevent menstrual blood from being discharged smoothly. Intrauterine adhesions can also inhibit women of childbearing age from becoming pregnant normally. The usual method is the hysteroscopic adhesiolysis to separate the adhesion sites again. However, despite the widespread use of hysteroscopic surgery, treatment of intrauterine adhesion is still very difficult, and the prognosis of intrauterine adhesion therapy is still unsatisfactory. Some adhesions, such as those at uterine horns or severe intrauterine adhesions, are still prone to recurrence and are difficult to be cured, even after the hysteroscopic adhesiolysis. Pregnancy after intrauterine adhesion is a high-risk pregnancy with high risk of abortion and abnormal placenta. Close monitoring is needed to prevent complications. Therefore, the treatment of intrauterine adhesions not only includes the hysteroscopic surgery to restore the normal shape of the uterine cavity, but also means to promote endometrial repair, prevent recurrence of intrauterine adhesions, and ultimately restore the normal life and fertility function.

At present, there are many methods and means for preventing re-adhesion after intrauterine adhesiolysis. Such conventional methods include drug therapy, intrauterine barrier media, balloon dilatation, bio-gel therapy, amniotic membrane transplantation, fiber hysteroscopy and blunt adhesiolysis. However, there is still no method available that can effectively and completely avoid the re-adhesion, and there is no unified treatment standard.

Oral estradiol drug has an effect on preventing adhesions, but due to the first-pass effect of the liver of oral drugs, coupled with the relative independence of the pelvic blood circulation system, most of the oral drug is intercepted by the liver, and the systemic blood concentration is not high. In particular, the concentration reaching the inside of the uterus is very low, and the bioavailability is very low.

There are many cases of transdermal drug delivery in clinical practice. Some publications have shown that the serum concentration of estradiol (E2) is increased by 211.89±57.40 pg/ml after the oral administration of 4 mg (2 mg bid) estradiol valerate; the serum concentration of estradiol is increased by 201.01±51.196 pg/ml after the vaginal external use of 0.5 mg of femoston estradiol; and the serum concentration of estradiol is increased by about 589.65 pg/ml after the vaginal external use of 1 mg of femoston estradiol. It is observed that vaginal administration of the drug femoston estradiol can have an absorption effect about 10 to 20 times that of oral administration.

When estradiol valerate or estradiol is administered vaginally, the estrogen can be quickly and effectively absorbed into the blood by the vaginal mucosa. Estradiol valerate is lysed by the esterase in the blood during vaginal administration. This process is very rapid, but due to the absorption efficiency of the vaginal mucosa, it has an effect on absorption and utilization. It is generally believed that the vaginal administration of estradiol valerate is about 4 to 8 times that of the oral administration. 95% of orally-administered estrogen is inactivated by the liver. However, the estrogen absorbed in the vagina enters the inferior vena cava directly through the vaginal vein without passing through the portal vein of liver, thus the first-pass effect of the liver is avoided. Transvaginal administration can prevent estradiol from being converted into estrone (E1) in the intestine and liver, making E2/E1 closer to physiological ratio. In vaginal administration, E2 acts directly on the endometrial related receptors and exerts an effect on the endometrium.

These examples show that the intrauterine targeted drug can achieve small-dose and high-efficiency.

Most of the above treatment is only temporary to reduce the chance of adhesions. After the disappearance of the device or drug, the probability of re-adhesion is very high, especially for patients with moderate to severe adhesions. It is a challenge of the growth of the endometrium, especially the growth of the endometrium whose basal layer has been damaged. Large doses of oral drugs have little effect on the endometrium whose basal layer has been damaged, and may cause great side effects on patients. Insufficient endometrial thickness is one of the main factors of infertility. Therefore, how to activate the basal layer cells to re-activate and differentiate the functional layer, in order to obtain a reasonable thickness of the endometrium, is the key to prevent adhesion and to restore fertility.

Silicone rubber is a kind of polymer material with excellent performance in medical applications. It is widely used as a medical artificial material with a low cost. The material is safe for the body with less exclusive reactions. That is to say, the silicone rubber has a good biological adaptability without adhering to the capillaries of the body.

Silicone rubber products have good medical characteristics, such as colorless, non-toxic, high temperature resistance, oxidation resistance, softness, and high transparency. Thus, silicone rubber products can solve many medical problems and meet requirements for medical use.

In addition, silicone rubber can also be used in the manufacture of products such as artificial heart valves, artificial lungs, bone adhesives, artificial skins, burn dressings, cardiac pacemaker insulated wires, sutures, various splints, catheters, grafts, tracheas, dental materials, insert materials, family planning products, gynecological products, etc.

The application of silicone rubber in obstetrics and gynecology is mainly on birth control devices and other anti-inflammatory products. There is typically a tail wire at the end of the gynecological products, such as birth control devices and anti-inflammatory products for placement in the uterus in order to facilitate the removal of the product. Specifically, there may be through-holes in the silicone rubber film for passing though the wire to be pulled. However, the pulling wires can cause a cutting force on the silicone rubber film near the through-holes, and cracks often happen on the silicone rubber product due to the softness of the silicone rubber material, resulting in removal difficulties.

Therefore, it is highly desirable to provide an elastic sheet that is easy to be implanted into the body and that is easy to be removed from the body.

SUMMARY OF THE INVENTION

The present disclosure provides an elastic sheet with a function of re-activating an endometrial basal layer in a uterine cavity and a forming method thereof.

The present disclosure provides an elastic sheet with a function of re-activating an endometrial basal layer in a uterine cavity, comprising a silicone rubber and a drug, wherein the drug is encased inside the silicone rubber in the manner of a drug storage zone, or uniformly dispersed inside the silicone rubber, or carried by an outer surface of the silicone rubber as a coating, and the drug comprises an estrogen.

It should be understood that the elastic sheet in which the drug is encased inside the silicone rubber in the manner of the drug storage zone is called a reservoir-type elastic sheet, the elastic sheet in which the drug is uniformly dispersed inside the silicone rubber is called a matrix-type elastic sheet, and the elastic sheet in which the drug is carried by the outer surface of the silicone rubber as the coating is called a coating-type elastic sheet.

In some embodiments, the silicone rubber includes heat vulcanized silicone rubber (HTV), room temperature vulcanized silicone rubber (RTV), low temperature vulcanized silicone rubber (LTV), DOWCORNING Silastic-382 medical silicone rubber, and DOWCORNING Q7 medical silicone rubber series and implantable MDX series.

In some embodiments, the silicone rubber is a self-modifying HTV. The silicone rubber is formed by kneading 40-80 wt % of HTV silicone rubber, 10-50 wt % of silica, 5-15 wt % of hydroxy silicone oil, 5-30 wt % of medical barium sulfate, 0.1-2 wt % of iron oxide red, and 0.5-1.5 wt % of benzoyl peroxide, under the condition that the sum of the components is 100 wt %. The elastic sheet is thus processed in such a manner that the above silicone rubber and the drug are mixed in a weight ratio, and then vulcanized and crosslinked, and solidified into a mixed sheet from the silicone rubber and drug to form the matrix-type elastic sheet.

In some embodiments, the silicone rubber is an additive RTV-2 or LTV. The silicone rubber is formed by kneading 40-80 wt % of silicone rubber, 20-60 wt % of silica, 5-15 wt % of hydroxy silicone oil, 5-30 wt % of medical barium sulfate, 0.1-2 wt % of iron oxide red, under the condition that the sum of the components is 100 wt % in a rubber mixer, which is then divided into two groups each with an equal weight. The elastic sheet is thus processed in such a manner that the above two groups of silicone rubber and the drug are mixed in a weight ratio, wherein the group A is kneaded with 0.1-1% platinum catalyst in a rubber mixer to form a uniform, the group B is kneaded with 1-10% active hydrogen cross-linking agent in a rubber mixer to form a uniform and cut into small pieces, and then the products obtained from the two groups are mixed and extruded, and then vulcanized and crosslinked, and solidified into a mixed sheet from the silicone rubber and drug to form the matrix-type elastic sheet.

In some embodiments, a weight ratio of the silicone rubber to the drug of the matrix-type elastic sheet is 80-99%: 20-1%, preferably 50-85:15-50. The matrix-type elastic sheet has a thickness of 0.02 mm-1 mm. It should be understood that the small thickness is beneficial to the delivery into and the removal from the uterus after the implantation. The enabled lower limit of the uniform thickness is 0.02 mm. The elastic sheet can be contracted into a roll and then placed in a delivery tube. Under normal circumstances, the outer diameter of the maximum tube that can pass through the cervical canal is 5 mm. The outer diameter of the maximum tube that can pass through the cervical canal is about 12 mm if the cervical canal is expanded by an instrument. Therefore, the patient suffers less surgical pains with the thinner elastic sheet. In some embodiments, the matrix-type elastic sheet is formed by fewer steps with a lower cost, compared with the reservoir-type and the coating-type elastic sheets.

In some embodiments, an outer surface of the matrix-type elastic sheet may be further wrapped with a separate outer silicone rubber film to form a reservoir-type elastic sheet. The outer silicone rubber film completely wraps the matrix-type elastic sheet. The outer silicone rubber film does not contain drug and can play a role in additional controlled release of the drug.

In some embodiments, a weight ratio of the silicone rubber to the drug of the reservoir-type elastic sheet is 0-99%:100-1%. The matrix-type elastic sheet has a thickness of 0.02 mm-1 mm, and the outer silicone rubber film has a thickness of 0.02 mm-0.5 mm.

In some embodiments, the coating-type elastic sheet can be formed by dissolving the drug and a degradable polymer (such as PLGA) in a solvent to form a drug solution, and then spraying the drug solution onto the silicone rubber to form a sustained release coating. A weight ratio of the drug to the degradable polymer in the drug solution is 10-90%: 90-10%, and the concentration of the two in the solvent is 0.1%-50%.

In some embodiments, the estrogen includes but not limited to 17β estradiol, estrone, estriol, estradiol derivatives, such as estradiol benzoate, estradiol valerate, ethinyl estradiol, ethinyl estradiol, conjugated estrogens, etc. Compared with oral administration or other administration methods, the estrogen of the present disclosure is locally targeted and released, and acts to stimulate endometrial hyperplasia without side effects such as hormonal disturbance caused by a large dose.

In some embodiments, the drug further comprises a drug for increasing capillary blood supply to improve endometrial blood flow, which works well together with the estrogen to better promote endometrial hyperplasia. The drug for improving endometrial blood flow includes but not limited to aspirin, sildenafil citrate, pentoxifylline (PTX) and vitamin E, L-arginine, and low molecular weight heparin. In some embodiments, the daily release amount of the drug for improving endometrial blood flow is 200 μg-2 mg, and the elastic sheet has estrogen of 2 mg-500 mg.

In some embodiments, the drug further comprises a colony stimulating factor for modulating local immunity of the uterine cavity, which is capable of promoting endometrial basal cell proliferation. The colony stimulating factor includes but not limited to granulocyte colony stimulating factor (G-CSF), granulocyte-macrophage colony stimulating factor (GM-CSF), etc.

In some embodiments, the release period of the sustained release system of the elastic sheet can be designed to be 3-90 days as needed, and in particular, it can be designed as a release period of 7 days, 14 days, 30 days, 60 days, 90 days, etc. If more than two drugs work synergistically, the release periods of all drugs can overlap each other, namely the release periods of all drugs are equivalent. The release periods of different drugs can also be different, but the longest release period does not exceed the designed release period range. For example, the drug for improving endometrial blood flow is released at first to improve endometrial blood flow, and the estrogen is released for treatment during the release period of the drug for improving endometrial blood flow.

In some embodiments, the elastic sheet has an intervening removal wire and/or an intervening implant wire. In some embodiments, the removal wire is sheathed with a thin tube and/or the implant wire is sheathed with a thin tube. In some embodiments, the removal wire is inserted into bores of the elastic sheet through rivet structures and/or the implant wire is inserted into bores of the elastic sheet through rivet structures. In some embodiments, a region with the bores has a thickened portion. In some embodiments, the elastic sheet comprises 25-100 mg of the drug.

In some embodiments, the elastic sheet is designed to have a big upper end and a small lower end. After the implantation, the upper end corresponds to the uterine fundus, and the lower end corresponds to the uterine cervix at an intrauterine opening. The preferred shape is an inverted trapezoidal shape, and the trapezoidal lower bottom (the upper end of the sheet, at the uterine fundus) has a length of 20-40 mm, the trapezoidal upper bottom (the lower end of the sheet, at the intrauterine opening of the uterine cervix) has a length of 5 mm-15 mm, and the trapezoidal height is 25 mm-35 mm. In some embodiments, the thickness of the elastic sheet is between 0.1 mm and 4 mm, preferably between 0.2 mm and 1 mm. In some embodiments, the elastic sheet has estrogen of 10 mg-200 mg.

Usually, when the basal layer of the uterus is damaged, the damaged part does not change with the change of hormones. Therefore, after the adhesion is separated by a known method, since the adhesive portion still cannot produce the functional layer, adhesion is likely to occur again. Surprisingly, according to the present disclosure, the estrogen is loaded on the silicone rubber, and thus the endometrial basal layer is continuously activated through drug stimulation, allowing for the endometrial basal layer to re-proliferate the functional layers, thereby restoring the normal endometrial structure and completely preventing adhesions. In particular, in patients with scarred uterus or uterine fibrosis, it is only necessary to surgically separate the fibrotic endometrial basal layer or scar to create a wound surface, so that the regeneration ability of endometrial functional layers can be activated through continuous estrogen stimulation. In some embodiments, the estrogen has a daily release of 10 μg-4 mg to a threshold of action for at least one week to provide a sustained release system with a controlled release rate and a release period. In some embodiments, the estrogen has a daily release of estrogen of 20 μg-1 mg, and the elastic sheet has estrogen of 10 mg-200 mg.

The present disclosure also provides a method for forming an elastic sheet, comprising: mixing, vulcanizing, crosslinking and solidifying a silicone rubber with a drug into a mixed sheet from the silicone rubber and drug to form a matrix-type elastic sheet.

In some embodiments, the silicone rubber is formed by kneading 40-80 wt % of HTV silicone rubber, 10-50 wt % of silica, 5-15 wt % of hydroxy silicone oil, 5-30 wt % of medical barium sulfate, 0.1-2 wt % of iron oxide red, and 0.5-1.5 wt % of benzoyl peroxide, under the condition that the sum of the components is 100 wt %.

In some embodiments, the silicone rubber is formed by kneading 40-80 wt % of silicone rubber, 20-60 wt % of silica, 5-15 wt % of hydroxy silicone oil, 5-30 wt % of medical barium sulfate, 0.1-2 wt % of iron oxide red, under the condition that the sum of the components is 100 wt % in a rubber mixer, which is then divided into two groups each with an equal weight; the two groups of silicone rubber and the drug are mixed in a weight ratio, wherein the group A is kneaded with 0.1-1% platinum catalyst in a rubber mixer to form a uniform, the group B is kneaded with 1-10% active hydrogen cross-linking agent in a rubber mixer to form a uniform and cut into small pieces, and then the products obtained from the two groups are mixed and extruded, and then vulcanized and crosslinked, and solidified into a mixed sheet from the silicone rubber and drug to form the matrix-type elastic sheet.

In some embodiments, an outer surface of the matrix-type elastic sheet is further wrapped with a separate outer silicone rubber film to form a reservoir-type elastic sheet.

The present disclosure also provides a method for forming an elastic sheet, comprising: dissolving the drug and a degradable polymer in a solvent to form a drug solution, and then spraying the drug solution onto the silicone rubber to form a sustained release coating.

In summary, according to the present disclosure, estrogen is loaded on the silicone rubber, and thus the endometrial basal layer is continuously activated through drug stimulation, allowing for the endometrial basal layer to re-proliferate the functional layers, thereby restoring the normal endometrial structure and completely preventing adhesions.

BRIEF DESCRIPTION OF THE DRAWINGS

Further details, features and advantages of designs of the invention result from the following description of embodiment examples in reference to the associated drawings.

FIG. 3 is a schematic view of an elastic sheet with a function of re-activating an endometrial basal layer in a uterine cavity according to yet another embodiment of the present disclosure;

FIG. 4 is a side view of FIG. 3;

FIG. 7 is a schematic view of an elastic sheet with a function of re-activating an endometrial basal layer in a uterine cavity according to yet another embodiment of the present disclosure;

FIG. 8 is a schematic view of a rivet structure of an elastic sheet with a function of re-activating an endometrial basal layer in a uterine cavity according to yet another embodiment of the present disclosure;

DESCRIPTION OF THE ENABLING EMBODIMENTS

Figure 1:
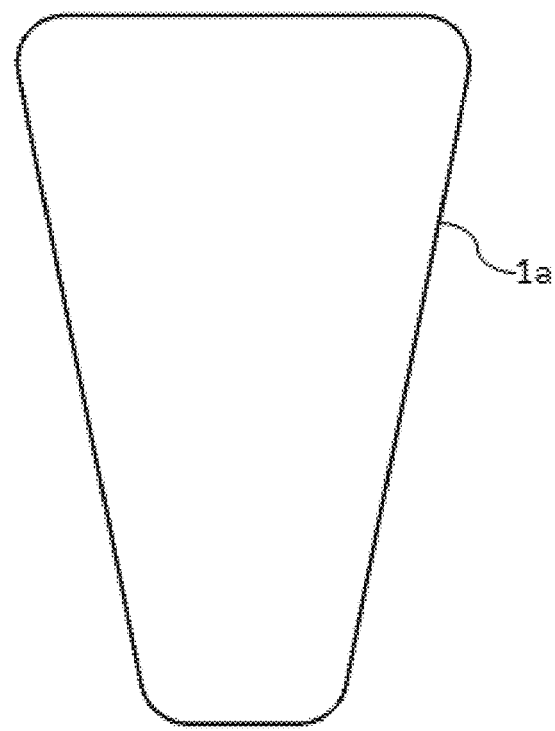
FIG. 1 is a schematic view of an elastic sheet with a function of re-activating an endometrial basal layer in a uterine cavity according to one embodiment of the present disclosure.

Referring to the drawings, the present invention will be described in detail in view of following embodiments.

As shown in FIG. 1, an elastic sheet 1a with a function of re-activating an endometrial basal layer in a uterine cavity according to one embodiment of the present disclosure has an inverted trapezoidal shape. After the implantation, the trapezoidal long bottom is located at the uterine fundus, and the trapezoidal short bottom is located at the cervix opening. It should be understood that, in the stretched state after the implantation, the shape of the elastic sheet 1a is adapted to the physiological shape and size of the uterus to isolate the anterior and posterior walls of the uterus as completely as possible, so that the contact between the anterior and posterior walls of the uterus is minimized. During the implantation, a conventional device is enough for the doctor to put the elastic sheet into the uterus. It should be understood that the elastic sheet can be contracted into a cylindrical shape by the doctor if necessary. The contracted elastic sheet can be delivery through the cervical canal into the uterus by a tube, and then be stretched after the implantation. Since the silicone rubber has glutinousness which prevents the contracted elastic sheet from being pushed out, the medical silicone oil can be applied at an end of the contracted elastic sheet to increase the lubrication between the sheet and the tube.

Figure 2:
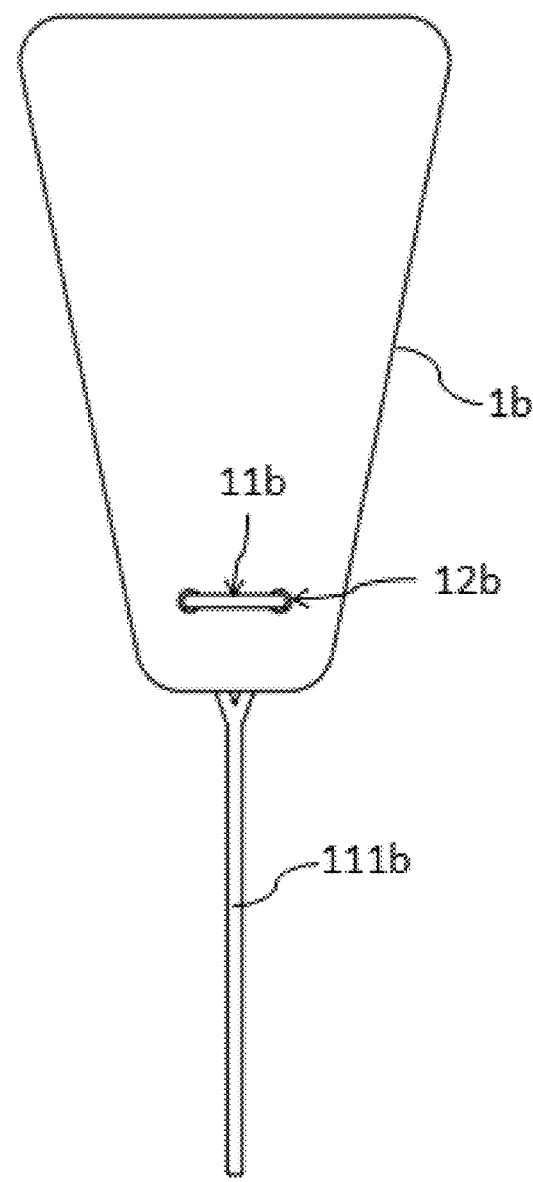
FIG. 2 is a schematic view of an elastic sheet with a function of re-activating an endometrial basal layer in a uterine cavity according to another embodiment of the present disclosure.

As shown in FIG. 2, an elastic sheet 1b with a function of re-activating an endometrial basal layer in a uterine cavity according to another preferred embodiment of the present disclosure has an intervening removal wire 11b. The elastic sheet 1b can be removed by the removal wire 11b after the release period or according to the doctor's follow-up evaluation. Specifically, the elastic sheet 1b has two tail wire holes 12b each of which is in a perfect circular shape. The removal wire 11b is inserted through the tail wire holes 12b and drags a tail wire 111b. The doctor can grip the tail wire 111b to pull the elastic sheet 1b out of the uterus if necessary. In the embodiment shown in FIG. 2, the tail wire holes 12b are located near the short bottom of the trapezoid, i.e., near the cervix opening, in order to reduce the take-out resistance. It should be understood that the tail wire holes 12b may be as close as possible to the end of the cervix opening, but may be at any position of the elastic sheet. The removal wire 11b is a biocompatible, non-degradable sewing thread, preferably a monofilament single-strand sewing thread. The material of the removal wire 11b includes but not limited to polypropylene, polyethylene, polyester, and polyamide. The removal wire 11b has a monofilament diameter of 0.1 mm-1 mm, and preferably has a diameter of 0.2-0.5 mm.

As shown in FIG. 3, an elastic sheet 1c with a function of re-activating an endometrial basal layer in a uterine cavity according to yet another preferred embodiment of the present disclosure has an implant wire 13c in addition to the intervening removal wire 11c. The delivery of the elastic sheet 1c can be assisted by the implant wire 13c during the implantation. Specifically, the elastic sheet 1c has two implant wire holes 14c each of which is in a perfect circular shape. The implant wire 13c is inserted through the implant wire holes 14c and does not drag any tail. In the embodiment shown in FIG. 3, the implant wire holes 14c are located near the long bottom of the trapezoid, i.e., near the uterine fundus, in order to facilitate the delivery. It should be understood that the implant wire holes 14c may be as close as possible to the end of the uterine fundus, but may be at any position of the elastic sheet. The implant wire 13c is a biocompatible, non-degradable sewing thread, preferably a monofilament single-strand sewing thread. The material of the implant wire 13c includes but not limited to polypropylene, polyethylene, polyester, and polyamide. The implant wire 13c has a monofilament diameter of 0.1 mm-1 mm, and preferably a diameter of 0.2-0.5 mm.

As shown in FIG. 4, the delivery device 2c for delivering the elastic sheet 1c has a rod shape, and its front end has a slit 21c by which the implant wire 13c is caught. It should be understood that two ends of the implant wire 13c are passed though the implant wire holes 14c and tied with a knot to form a coil, which should be tightened as much as possible without deforming the elastic sheet, so that the delivery force can be better transmitted through the implant wire 13c to the elastic sheet 1c. In the present embodiment, in order to facilitate the delivery, the width of the slit 21c is 0.1-0.3 mm larger than the diameter of the implant wire 13c, and the depth of the slit 21c is 2-8 mm. The maximum dimension of the cross section of the delivery device 2c is between 3 mm and 7 mm, preferably between 4 mm and 6 mm.

Figure 5:
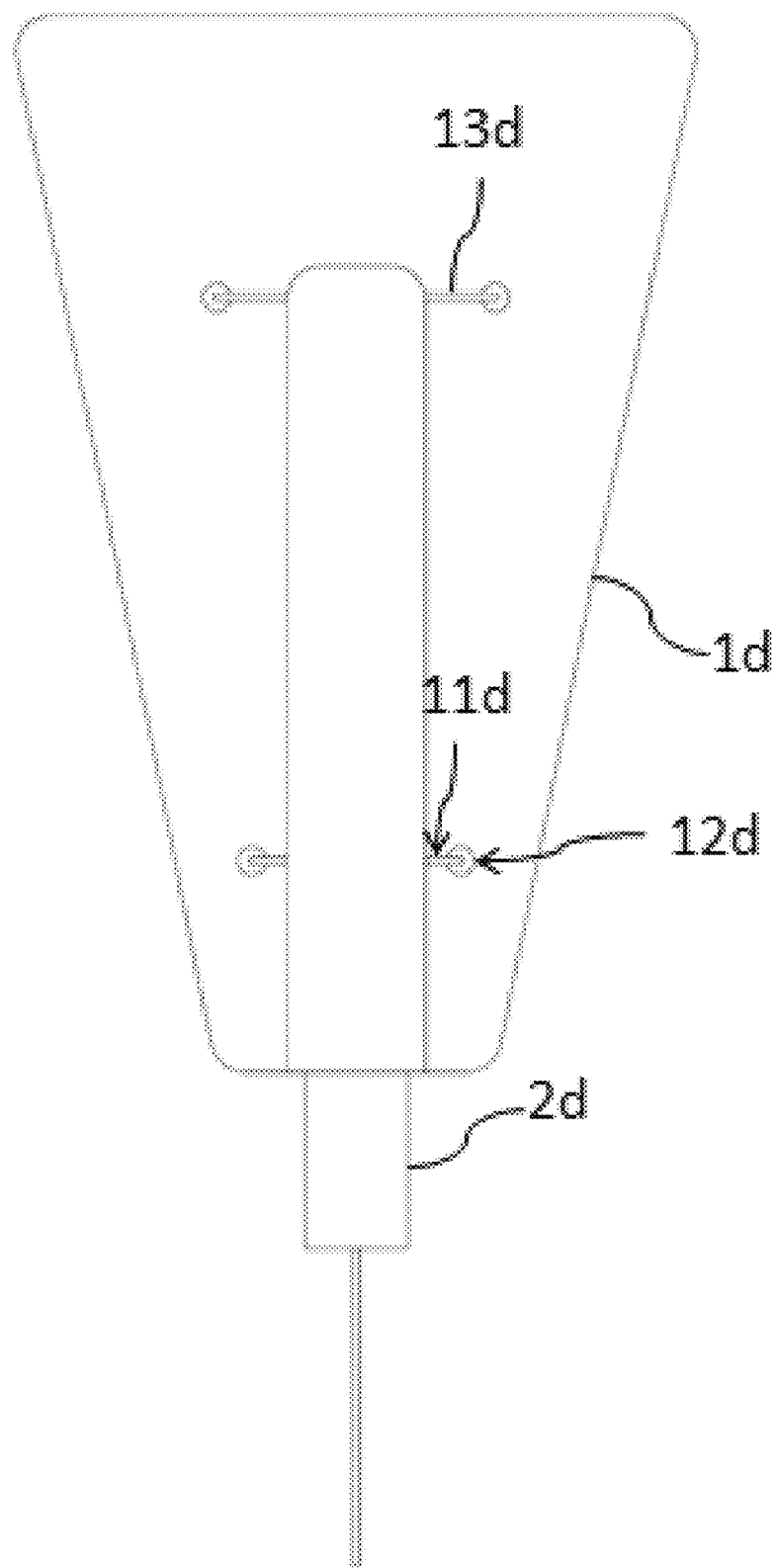
FIG. 5 is a schematic view of an elastic sheet with a function of re-activating an endometrial basal layer in a uterine cavity and a delivery device according to yet another embodiment of the present disclosure.

As shown in FIG. 5, an elastic sheet 1d with a function of re-activating an endometrial basal layer in a uterine cavity according to yet another embodiment of the present disclosure 1d has an intervening removal wire 11d and an intervening implant wire 13d, wherein two ends of the removal wire 11d are passed though the tail wire holes 12d and tied with a knot to form a coil of the removal wire 11d.

Figure 6:
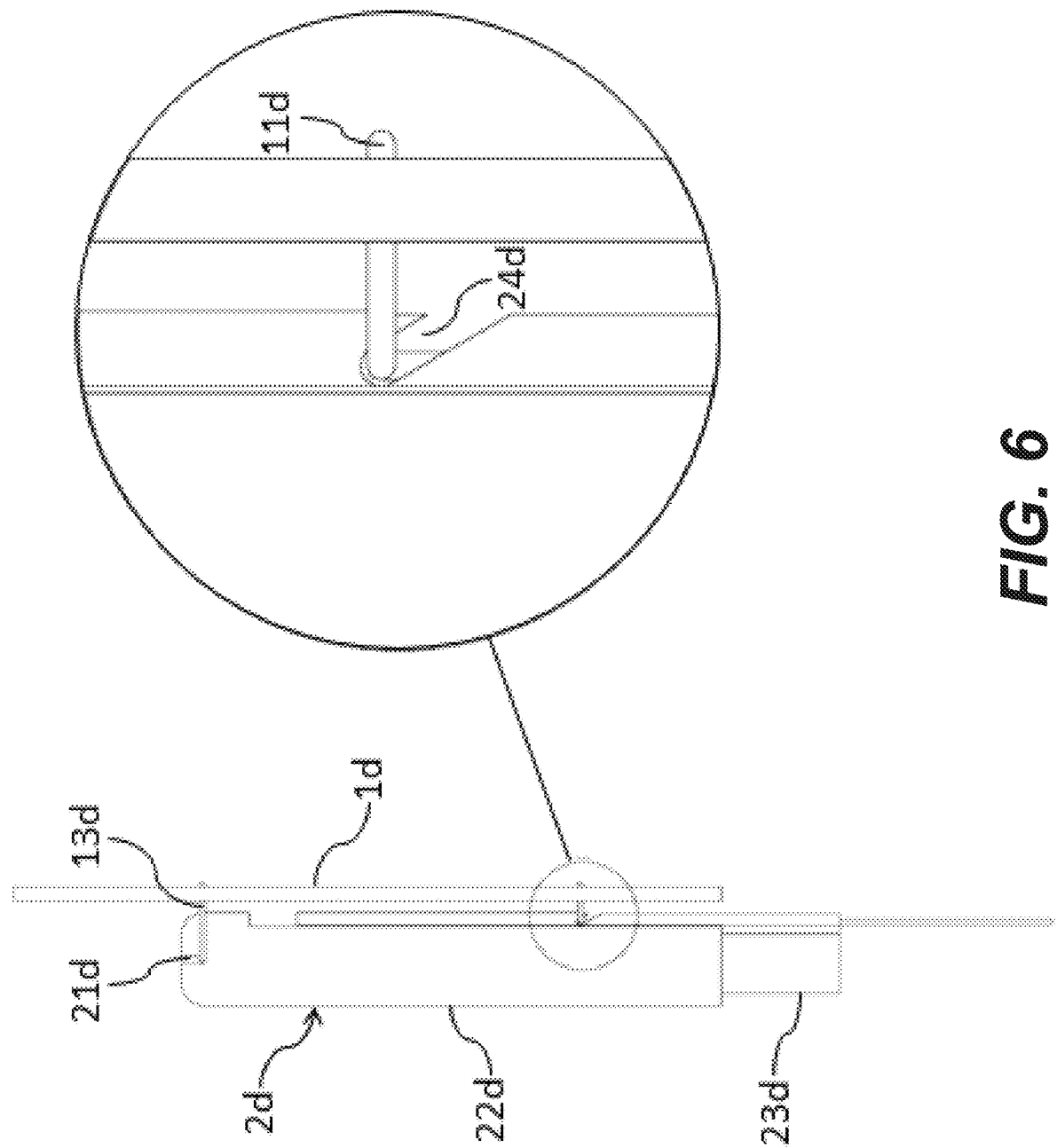
FIG. 6 is a side view of FIG. 5.

As shown in FIG. 6, the delivery device 2d for delivering the elastic sheet 1d has a rod shape, and includes a first portion 22d and a second portion 23d which are telescopic. The slit 21d having an upward opening is provided at the front end of the first portion 22d. The implant wire 13d is caught by the slit 21d. The second portion 23d has a barb 24d for hooking the removal wire 11d, wherein a downwardly oblique opening is formed by the barb. During the implantation, the first portion 22d and the second portion 23d slide away from each other to stretch the elastic sheet 1d in the axial direction of the rod, in order to maintain the orientation of the sheet for the successful implantation. After the elastic sheet 1d is stretched, the front end of the delivery device 2d does not exceed the bottom edge of the elastic sheet to avoid damaging the uterine fundus. After being implanted in place, the second portion 23d is slid toward the first portion 22d such that the removal wire 11d is released from the barb 24d to release the coil of the removal wire 11d, and then the delivery device 2d is taken out to complete the delivery. In the present embodiment, the depth of the barb 24d is 1-5 mm larger than the diameter of the removal wire 11d.

Figure 11:
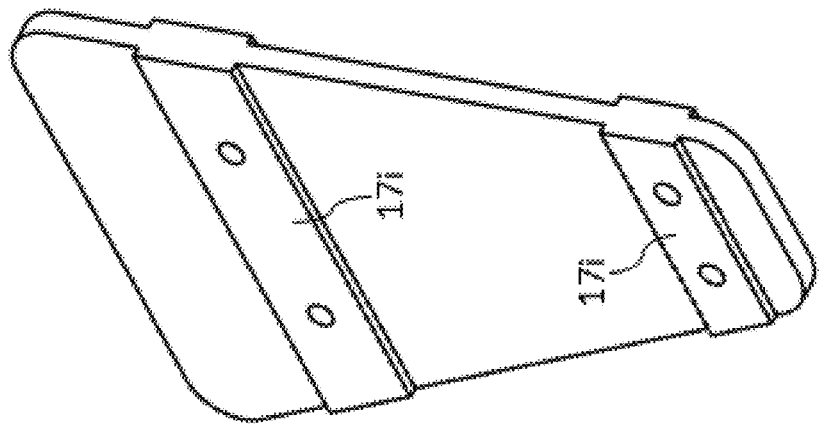
FIG. 11 is a schematic view of an elastic sheet with a function of re-activating an endometrial basal layer in a uterine cavity according to yet another embodiment of the present disclosure.
Figure 10:
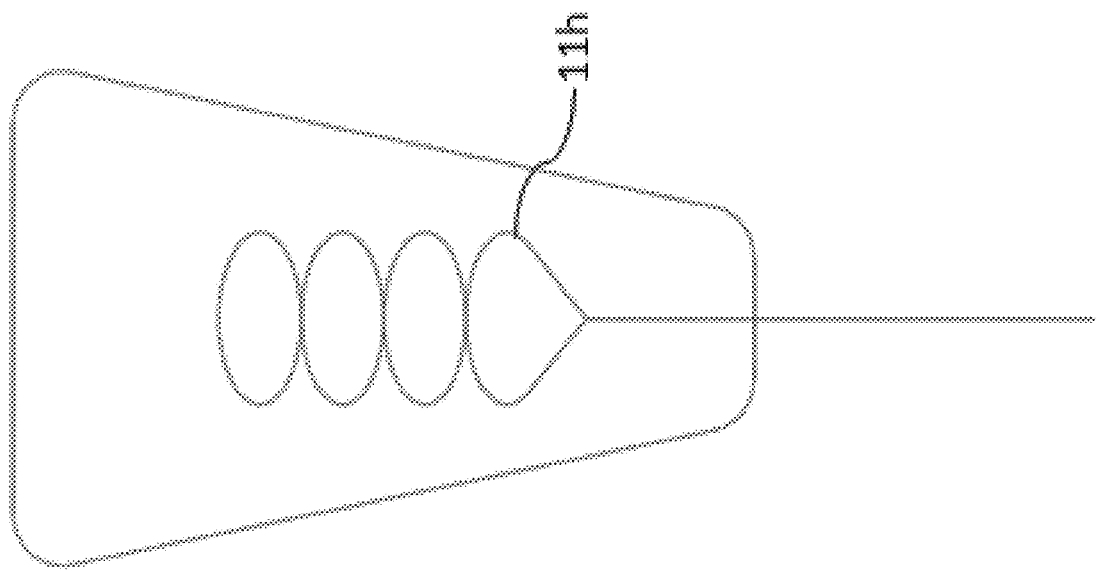
FIG. 10 is a schematic view of an elastic sheet with a function of re-activating an endometrial basal layer in a uterine cavity according to yet another embodiment of the present disclosure.
Figure 9:
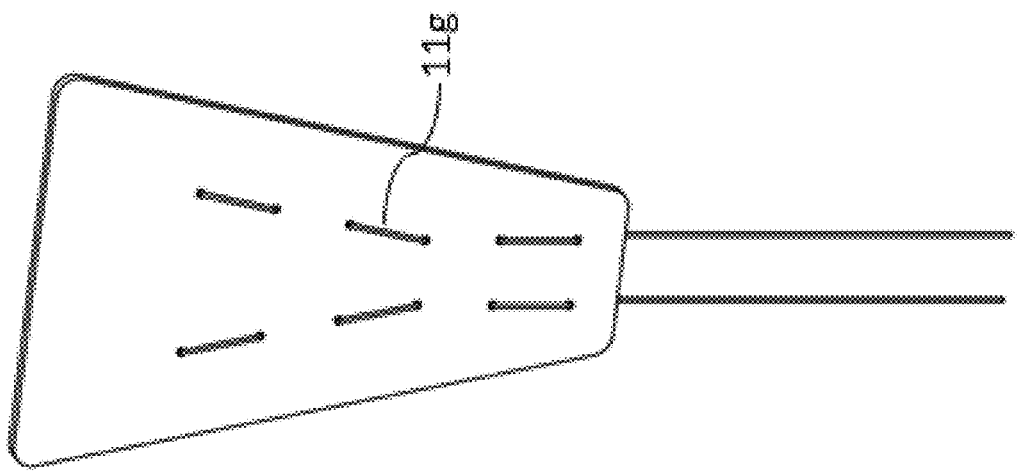
FIG. 9 is a schematic view of an elastic sheet with a function of re-activating an endometrial basal layer in a uterine cavity according to yet another embodiment of the present disclosure.

In the elastic sheet with a function of re-activating an endometrial basal layer in a uterine cavity according to the present application, the toughness of the silicone rubber is lowered after being filled with the drug, resulting in deterioration of the crack-resistant strength. In order to avoid the crack of the elastic sheet when the tail wire is pulled, namely in order to prevent the difficulty or even impossibility of the removal of the elastic sheet, the crack-resistant strength of the elastic sheet should be increased. In a preferred embodiment, as shown in FIG. 7, the coils of the removal wire 11e and implant wire 13e facing away from the delivery device 2e are sheathed each with a thin tube 15e, in order to reinforce the removal wire 11e and the implant wire 13e, so that the cracking force is transferred to the thin tube 15e from the removal wire 11e and the implant wire 13e. It should be understood that only the side facing away from the delivery device 2e of the coils is sheathed with thin tubes, namely the side facing the delivery device 2e of the coils is not sheathed to facilitate the stretch during the delivery. The material of the thin tube may be selected from a medical elastic body, preferably silicone rubber, having an inner diameter of 0.1-0.8 mm and an outer diameter of 0.3-2.5 mm. The length of the thin tube is cut as needed. However, the length of the thin tube should be greater than the straight length between the centers of the two holes, and shorter than the longest distance between the edges of the two holes. In another preferred embodiment, as shown in FIG. 8, a rivet structure 16f is provided in each of the tail wire holes and the implant wire holes for reinforcing. The rivet structure 16f is a prefabricated tubular with two large ends. Since the removal wire and the implant wire are passed through the rivet structure 16f which is caught in each of the tail wire holes and the implant wire holes, the region of the elastic sheet with holes is reinforced to prevent cracking. In still another preferred embodiment, as shown in FIG. 9, the rivet structure 16f is a prefabricated tubular with two large ends. Since the rivet structure 16f caught in each of the tail wire holes and the implant wire holes is passed through by the removal wire 11e or the implant wire 13e, the region of the elastic sheet with holes is reinforced in order to prevent the crack. In still another preferred embodiment, as shown in FIG. 11, the region with tail wire holes and the implant wire holes has a thickened portion 17i to improve its crack-resistant strength. In the present embodiment, the thickness of the thickened portion 17i does not exceed 2 mm.

Example 1

A matrix-type elastic sheet formed by a kneading sample containing 25 mg of estradiol:

i. 1 g of 17β estradiol (average particle size 5,000 mesh), 30 g of HTV medical silicone rubber (molecular weight 20-100 million), 10 g of silica, 5 g of hydroxy silicone oil, 6 g of medical barium sulfate, 0.5 g of iron oxide red, and 2 g of benzoyl peroxide were kneaded to a uniform on a rubber mixer, and hot pressed on a flat vulcanizer to form a sheet having a thickness of 0.5 mm, and then cut into a desired shape to obtain a matrix-type elastic sheet.

ii. The content of the drug in the sample was calculated according to the volume. The sample was dissolved in PBS solution at 37° C. on a drug dissolution tester, and the dissolution content was measured by HPLC. The result showed that within 30 days, the maximum amount of drug dissolution was 400 μg/d in the first 3 days, and then the drug dissolution was gradually stabilized, wherein the average drug release in 30 days was 178 μg/d.

iii. The New Zealand rabbits were tested. Before the implantation, 6 trauma models were obtained by surgical curettage and divided into two groups A and B. The group A was given the same dose per weight of estradiol by oral, and the group B was implanted the suitable size of the elastic sheet of the present embodiment without oral estradiol. After 30 days, different degrees of adhesions happened in the uteri of the test animals in group A, but there was no adhesion happened in the uteri of the test animals in group B, wherein the endometrial in group B grew well with mild and visible surgical trace.

Example 2

A reservoir-type elastic sheet formed by a kneading sample containing 50 mg of estradiol:
i. 3 g of 17β estradiol (average particle size 2,000 mesh) and 30 g of RTV-2 medical silicone rubber were kneaded to a uniform on a rubber mixer, and hot pressed on a flat vulcanizer to form a sheet having a thickness of 0.2 mm, and then cut into a desired shape to obtain a matrix-type elastic sheet.
ii. A certain amount of HTV medical silicone rubber was weighted and hot pressed to form a film with a thickness of 0.1 mm. The matrix-type elastic sheet obtained in step i. was sandwiched between two films of 0.1 mm to form a sandwich pattern, which was melted in a mold. The edge was cut off to form a composite sustained-release sheet, that is, a reservoir-type elastic sheet, wherein the outer HTV films further controls the amount of released drug.
iii. The content of the drug in the sample was calculated according to the volume. The sample was dissolved in PBS solution at 37° C. on a drug dissolution tester, and the dissolution content was measured by HPLC. The result showed that within 90 days, the maximum amount of drug dissolution was 100 μg/d in the first 3 days, and then the drug dissolution was gradually stabilized, wherein the average drug release in 90 days was 50 μg/d.
iv. The New Zealand rabbits were tested. Before the implantation, 6 trauma models were obtained by surgical curettage and divided into two groups A and B. The group A was given the same dose per weight of estradiol by oral, and the group B was implanted the suitable size of the elastic sheet of the present embodiment without oral estradiol. After 30 days, different degrees of adhesions happened in the uteri of the test animals in group A, but there was no adhesion happened in the uteri of the test animals in group B.

Example 3

A matrix-type elastic sheet formed by a kneading sample containing 100 mg of estradiol:
i. 5 g of 17β estradiol (average particle size 2,000 mesh), 30 g of HTV medical silicone rubber (molecular weight 20-100 million), 10 g of silica, 5 g of hydroxy silicone oil, 6 g of medical barium sulfate, 0.5 g of iron oxide red, and 2 g of benzoyl peroxide were kneaded to a uniform on a rubber mixer, and hot pressed on a flat vulcanizer to form a sheet having a thickness of 0.2 mm, and then cut into a desired shape to obtain a matrix-type elastic sheet.
ii. The content of the drug in the sample was calculated according to the volume. The sample was dissolved in PBS solution at 37° C. on a drug dissolution tester, and the dissolution content was measured by HPLC. The result showed that within 60 days, the maximum amount of drug dissolution was 760 μg/d in the first 3 days, and then the drug dissolution was gradually stabilized, wherein the average drug release in 60 days was 274 μg/d.
iii. The New Zealand rabbits were tested. Before the implantation, 6 trauma models were obtained by surgical curettage and divided into two groups A and B. The group A was given the same dose per weight of estradiol by oral, and the group B was implanted the suitable size of the elastic sheet of the present embodiment without oral estradiol. After 60 days, different degrees of adhesions happened in the uteri of the test animals in group A, but there was no adhesion happened in the uteri of the test animals in group B, wherein the endometrial in group B grew well.

Example 4

A matrix-type elastic sheet formed by a kneading sample containing 75 mg of estradiol:
i. Under the condition that the sum of the components was 100 wt %, 60 g of silicone rubber, 25 g of silica, 7 g of hydroxy silicone oil, 7.5 g of medical barium sulfate, and 0.5 g of iron oxide red were kneaded on a rubber mixer and divided into two groups according to the weight, each group being 50 g.
ii. 12.5 g of estradiol (average particle size 2,000 mesh) and 50 g of the group A, 0.1-1% of platinum catalyst were kneaded to a uniform on a rubber mixer. 12.5 g of estradiol (average particle size 2,000 mesh) and 50 g of the group B, and 1-10% active hydrogen cross-linking agent were kneaded to a uniform on a rubber mixer. Then the products obtained from the two groups were mixed and extruded, then vulcanized and crosslinked, and solidified into a mixed sheet from the silicone rubber and drug to form a matrix-type elastic sheet.
iii. The content of the drug in the sample was calculated according to the volume. The sample was dissolved in PBS solution at 37° C. on a drug dissolution tester, and the dissolution content was measured by HPLC. The result showed that within 60 days, the maximum amount of drug dissolution was 652 μg/d in the first 3 days, and then the drug dissolution was gradually stabilized, wherein the average drug release in 60 days was 243 μg/d.
iv. The New Zealand rabbits were tested. Before the implantation, 6 trauma models were obtained by surgical curettage and divided into two groups A and B. The group A was given the same dose per weight of estradiol by oral, and the group B was implanted the suitable size of the elastic sheet of the present embodiment without oral estradiol. After 60 days, different degrees of adhesions happened in the uteri of the test animals in group A, but there was no adhesion happened in the uteri of the test animals in group B, wherein the endometrial in group B grew well.

Example 5

A matrix-type elastic sheet formed by a kneading sample containing 10 mg of estradiol and 2 mg of aspirin:
i. Under the condition that the sum of the components was 100 wt %, 70 g of silicone rubber, 15 g of silica, 8 g of hydroxy silicone oil, 6 g of medical barium sulfate, and 1 g of iron oxide red were kneaded on a rubber mixer and divided into two groups according to the weight, each group being 50 g.
ii. 2.5 g of estradiol (average particle size 2,000 mesh) and 50 g of the group A, 0.1-1% of platinum catalyst were kneaded to a uniform on a rubber mixer. 0.5 g of aspirin (average particle size 500 mesh) and 50 g of the group B, and 1-10% active hydrogen cross-linking agent were kneaded to a uniform on a rubber mixer. Then the products obtained from the two groups were mixed and extruded, then vulcanized and crosslinked, and solidified into a mixed sheet from the silicone rubber and drug to form a matrix-type elastic sheet.

iii. The content of the drug in the sample was calculated according to the volume. The sample was dissolved in PBS solution at 37° C. on a drug dissolution tester, and the dissolution content was measured by HPLC. The result showed that within 60 days, the maximum amount of estradiol dissolution was 157 µg/d and the maximum amount of aspirin dissolution was 62 µg/d in the first 3 days, and then the drug dissolutions were gradually stabilized, wherein the average released estradiol was 94 µg/d and the average released aspirin was 42 µg/d in 60 days.

iv. The New Zealand rabbits were tested. Before the implantation, 6 trauma models were obtained by surgical curettage and divided into two groups A and B. The group A was given the same dose per weight of estradiol by oral, and the group B was implanted the suitable size of the elastic sheet of the present embodiment without oral estradiol. After 60 days, different degrees of adhesions happened in the uteri of the test animals in group A, but there was no adhesion happened in the uteri of the test animals in group B, wherein the endometrial in group B grew well.

Example 6

A matrix-type elastic sheet formed by a kneading sample containing 50 mg of estradiol and 20 mg of aspirin:

i. Under the condition that the sum of the components was 100 wt %, 70 g of silicone rubber, 15 g of silica, 8 g of hydroxy silicone oil, 6 g of medical barium sulfate, and 1 g of iron oxide red were kneaded on a rubber mixer and divided into two groups according to the weight, each group being 50 g.

ii. 12.5 g of estradiol (average particle size 2,000 mesh) and 50 g of the group A, 0.1-1% of platinum catalyst were kneaded to a uniform on a rubber mixer. 5 g of aspirin (average particle size 500 mesh) and 50 g of the group B, and 1-10% active hydrogen cross-linking agent were kneaded to a uniform on a rubber mixer. Then the products obtained from the two groups were mixed and extruded, then vulcanized and crosslinked, and solidified into a mixed sheet from the silicone rubber and drug to form a matrix-type elastic sheet.

iii. The content of the drug in the sample was calculated according to the volume. The sample was dissolved in PBS solution at 37° C. on a drug dissolution tester, and the dissolution content was measured by HPLC. The result showed that within 90 days, the maximum amount of estradiol dissolution was 543 µg/d and the maximum amount of aspirin dissolution was 489 µg/d in the first 3 days, and then the drug dissolutions were gradually stabilized, wherein the average released estradiol was 213 µg/d and the average released aspirin was 142 µg/d in 90 days.

iv. The New Zealand rabbits were tested. Before the implantation, 6 trauma models were obtained by surgical curettage and divided into two groups A and B. The group A was given the same dose per weight of estradiol by oral, and the group B was implanted the suitable size of the elastic sheet of the present embodiment without oral estradiol. After 90 days, different degrees of adhesions happened in the uteri of the test animals in group A, but there was no adhesion happened in the uteri of the test animals in group B, wherein the endometrial in group B grew well.

Example 7

A matrix-type elastic sheet formed by a kneading sample containing 10 mg of estradiol, 5 mg of pentoxifylline (PTX) and 5 mg of vitamin E:

i. Under the condition that the sum of the components was 100 wt %, 50 g of silicone rubber, 35 g of silica, 7 g of hydroxy silicone oil, 7 g of medical barium sulfate, and 1 g of iron oxide red were kneaded on a rubber mixer and divided into two groups according to the weight, each group being 50 g.

ii. 2.5 g of estradiol (average particle size 2,000 mesh) and 50 g of the group A, 0.1-1% of platinum catalyst were kneaded to a uniform on a rubber mixer. 1.5 g of PTX (average particle size 500 mesh), 1.5 g of vitamin E (average particle size 800 mesh) and 50 g of the group B, and 1-10% active hydrogen cross-linking agent were kneaded to a uniform on a rubber mixer. Then the products obtained from the two groups were mixed and extruded, then vulcanized and crosslinked, and solidified into a mixed sheet from the silicone rubber and drug to form a matrix-type elastic sheet.

iii. The content of the drug in the sample was calculated according to the volume. The sample was dissolved in PBS solution at 37° C. on a drug dissolution tester, and the dissolution content was measured by HPLC. The result showed that within 90 days, the maximum amount of estradiol dissolution was 145 µg/d, the maximum amount of PTX dissolution was 89 µg/d and the maximum amount of vitamin E dissolution was 99 µg/d in the first 3 days, and then the drug dissolutions were gradually stabilized, wherein the average released estradiol was 89 µg/d, the average released PTX was 63 µg/d and the average released vitamin E was 69 µg/d in 90 days.

iv. The New Zealand rabbits were tested. Before the implantation, 6 trauma models were obtained by surgical curettage and divided into two groups A and B. The group A was given the same dose per weight of estradiol by oral, and the group B was implanted the suitable size of the elastic sheet of the present embodiment without oral estradiol. After 90 days, different degrees of adhesions happened in the uteri of the test animals in group A, but there was no adhesion happened in the uteri of the test animals in group B, wherein the endometrial in group B grew well.

Example 8

A matrix-type elastic sheet formed by a kneading sample containing 50 mg of estradiol, 10 mg of pentoxifylline (PTX) and 10 mg of vitamin E:

i. Under the condition that the sum of the components was 100 wt %, 50 g of silicone rubber, 35 g of silica, 7 g of hydroxy silicone oil, 7 g of medical barium sulfate, and 1 g of iron oxide red were kneaded on a rubber mixer and divided into two groups according to the weight, each group being 50 g.

ii. 12.5 g of estradiol (average particle size 2,000 mesh) and 50 g of the group A, 0.1-1% of platinum catalyst were kneaded to a uniform on a rubber mixer. 3 g of PTX (average particle size 500 mesh), 3 g of vitamin E (average particle size 800 mesh) and 50 g of the group B, and 1-10% active hydrogen cross-linking agent were kneaded to a uniform on a rubber mixer. Then the products obtained from the two groups were mixed and extruded, then vulcanized and crosslinked, and solidified into a mixed sheet from the silicone rubber and drug to form a matrix-type elastic sheet.

iii. The content of the drug in the sample was calculated according to the volume. The sample was dissolved in PBS solution at 37° C. on a drug dissolution tester, and the dissolution content was measured by HPLC. The result showed that within 90 days, the maximum amount of estradiol dissolution was 562 µg/d, the maximum amount of PTX dissolution was 156 µg/d and the maximum amount of vitamin E dissolution was 175 µg/d in the first 3 days, and then the drug dissolutions were gradually stabilized, wherein the average released estradiol was 236 µg/d, the average released PTX was 109 µg/d and the average released vitamin E was 113 µg/d in 90 days.

iv. The New Zealand rabbits were tested. Before the implantation, 6 trauma models were obtained by surgical curettage and divided into two groups A and B. The group A was given the same dose per weight of estradiol by oral, and the group B was implanted the suitable size of the elastic sheet of the present embodiment without oral estradiol. After 90 days, different degrees of adhesions happened in the uteri of the test animals in group A, but there was no adhesion happened in the uteri of the test animals in group B, wherein the endometrial in group B grew well.

Example 9

A reservoir-type elastic sheet formed by a drug-only sample containing 75 mg of estradiol:

i. A certain amount of HTV medical silicone rubber was weighted and hot pressed to form a film with a thickness of 0.05 mm, and cut it into two inverted trapezoidal shape (as shown in FIG. 1). One of the film was tiled, and 75 mg of estradiol (average particle size of 5,000 mesh) was placed evenly in the center of the film, leaving at least 3 mm of the edge-sealing position, and then another inverted trapezoidal film was placed thereon. The two films were heat pressed or bonded together, wherein the drug powder was wrapped in a closed pocket.

ii. The content of the drug in the sample was calculated according to the volume. The sample was dissolved in PBS solution at 37° C. on a drug dissolution tester, and the dissolution content was measured by HPLC. The result showed that within 90 days, the maximum amount of drug dissolution was 186 µg/d in the first 3 days, and then the drug dissolution was gradually stabilized, wherein the average drug release in 90 days was 165 µg/d.

iii. The New Zealand rabbits were tested. Before the implantation, 6 trauma models were obtained by surgical curettage and divided into two groups A and B. The group A was given the same dose per weight of estradiol by oral, and the group B was implanted the suitable size of the elastic sheet of the present embodiment without oral estradiol. After 30 days, different degrees of adhesions happened in the uteri of the test animals in group A, but there was no adhesion happened in the uteri of the test animals in group B.

Example 10

A reservoir-type elastic sheet formed by a kneading sample containing 100 mg of estradiol:

i. 5 g of 17β estradiol (average particle size 2,000 mesh), 30 g of HTV medical silicone rubber (molecular weight 20-100 million), 10 g of silica, 5 g of hydroxy silicone oil, 6 g of medical barium sulfate, 0.5 g The iron oxide red, and 2 g of benzoyl peroxide were kneaded to a uniform on a rubber mixer, and hot pressed on a flat vulcanizer to form a sheet having a thickness of 0.2 mm, and then cut into a desired shape to obtain a matrix-type elastic sheet.

ii. A certain amount of HTV medical silicone rubber was weighted and hot pressed to form a film with a thickness of 0.1 mm. The matrix-type elastic sheet obtained in step i. was sandwiched between two films of 0.1 mm to form a sandwich pattern, which was melted in a mold. The edge was cut off to form a composite sustained-release sheet, that is, a reservoir-type elastic sheet, wherein the outer HTV films further controls the amount of released drug.

iii. The content of the drug in the sample was calculated according to the volume. The sample was dissolved in PBS solution at 37° C. on a drug dissolution tester, and the dissolution content was measured by HPLC. The result showed that within 90 days, the maximum amount of drug dissolution was 201 µg/d in the first 3 days, and then the drug dissolution was gradually stabilized, wherein the average drug release in 90 days was 180 µg/d.

iv. The New Zealand rabbits were tested. Before the implantation, 6 trauma models were obtained by surgical curettage and divided into two groups A and B. The group A was given the same dose per weight of estradiol by oral, and the group B was implanted the suitable size of the elastic sheet of the present embodiment without oral estradiol. After 30 days, different degrees of adhesions happened in the uteri of the test animals in group A, but there was no adhesion happened in the uteri of the test animals in group B.

Example 11

A coating-type elastic sheet formed by a spraying sample containing 10 mg of estradiol:

i. A certain amount of HTV medical silicone rubber was weighted and hot pressed to form a film with a thickness of 0.1 mm for use.

ii. 10 g of estradiol and 90 g of PLGA (mol ratio 10:90) were dissolved in 1000 ml of acetone, and the obtained drug solution was sprayed on both sides of the film obtained in step i, and then the solvent was evaporated.

iii. The elastic sheet was cut into suitable size. The sample was dissolved in PBS solution at 37° C. on a drug dissolution tester, and the dissolution content was measured by HPLC. The result showed that within 60 days, the maximum amount of drug dissolution was 486 µg/d in the first 7 days, and then the drug dissolution was gradually stabilized, wherein the average drug release in 60 days was 150 µg/d.

iv. The New Zealand rabbits were tested. Before the implantation, 6 trauma models were obtained by surgical curettage and divided into two groups A and B. The group A was given the same dose per weight of estradiol by oral, and the group B was implanted the suitable size of the elastic sheet of the present embodiment without oral estradiol. After 30 days, different degrees of adhesions happened in the uteri of the test animals in group A, but there was no adhesion happened in the uteri of the test animals in group B.

Example 12

A coating-type elastic sheet formed by a spraying sample containing 50 mg of estradiol
  i. A certain amount of HTV medical silicone rubber was weighted and hot pressed to form a film with a thickness of 0.1 mm.
  ii. 45 g of estradiol and 5 g of PLGA (mol ratio 10:90) were dissolved in 2500 ml of acetone, and the obtained drug solution was sprayed on both sides of the film obtained in step i, and then the solvent was evaporated.
  iii. The elastic sheet was cut into suitable size. The sample was dissolved in PBS solution at 37° C. on a drug dissolution tester, and the dissolution content was measured by HPLC. The result showed that within 30 days, the maximum amount of drug dissolution was 2356 μg/d in the first 7 days, and then the drug dissolution was gradually stabilized, wherein the average drug release in 30 days was 1354 μg/d.
  iv. The New Zealand rabbits were tested. Before the implantation, 6 trauma models were obtained by surgical curettage and divided into two groups A and B. The group A was given the same dose per weight of estradiol by oral, and the group B was implanted the suitable size of the elastic sheet of the present embodiment without oral estradiol. After 30 days, different degrees of adhesions happened in the uteri of the test animals in group A, but there was no adhesion happened in the uteri of the test animals in group B.

Obviously, a matrix-type elastic sheet 1' formed by a kneading sample containing 50 mg of estradiol can be obtained according to above Example 2 without the step ii. A matrix-type elastic sheet 1" formed by a kneading sample containing 100 mg of estradiol can be obtained according to above Example 3. The two obtained elastic sheets are specifically discussed below.

Figure 12:
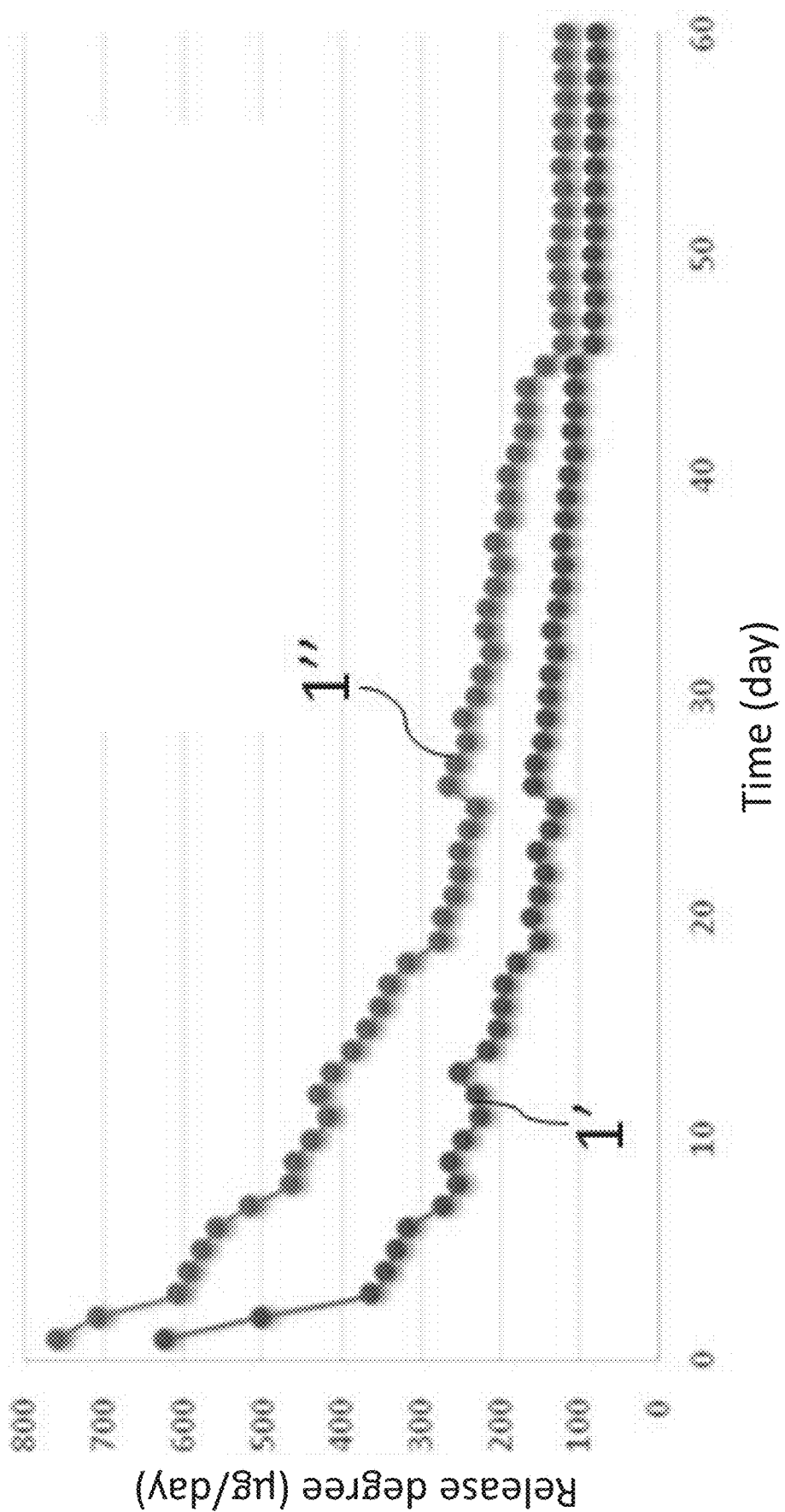
FIG. 12 shows the comparison of 60-day release curve in vitro of the matrix-type elastic sheet formed by a kneading sample containing 50 mg of estradiol and the matrix-type elastic sheet formed by a kneading sample containing 100 mg of estradiol.

FIG. 12 shows the comparison of 60-day release curve in vitro of the matrix-type elastic sheet 1' formed by a kneading sample containing 50 mg of estradiol and the matrix-type elastic sheet 1" formed by a kneading sample containing 100 mg of estradiol. It can be seen from the FIG. that the daily release amount of the matrix-type elastic sheet 1" formed by a kneading sample containing 100 mg of estradiol is larger than that of the matrix-type elastic sheet 1' formed by a kneading sample containing 50 mg of estradiol, but they are not in a multiple relationship. That is to say, the daily release can be increased by the total drug amount loaded on the elastic sheet, which is the key to activate the endometrium. Moreover, not all drugs can be released, and only 20% of the total drug amount is released in 60 days, which is limited by the fact that the silicone rubber is a non-degradable material, and most drugs cannot be completely released. It should be understood that in the case of a coating-type elastic sheet, since the drug is loaded on the outer surface of the silicone rubber and the polymer in the coating is degradable, more than 90% of the drug can be released. Therefore, the controlled release of the matrix-type elastic sheet and the reservoir-type elastic sheet is slower with a longer release period of 60-90 days, and even longer, while the coating-type elastic sheet has a rough control with a shorter release period of 30-60 days, and even shorter.

Figure 13:
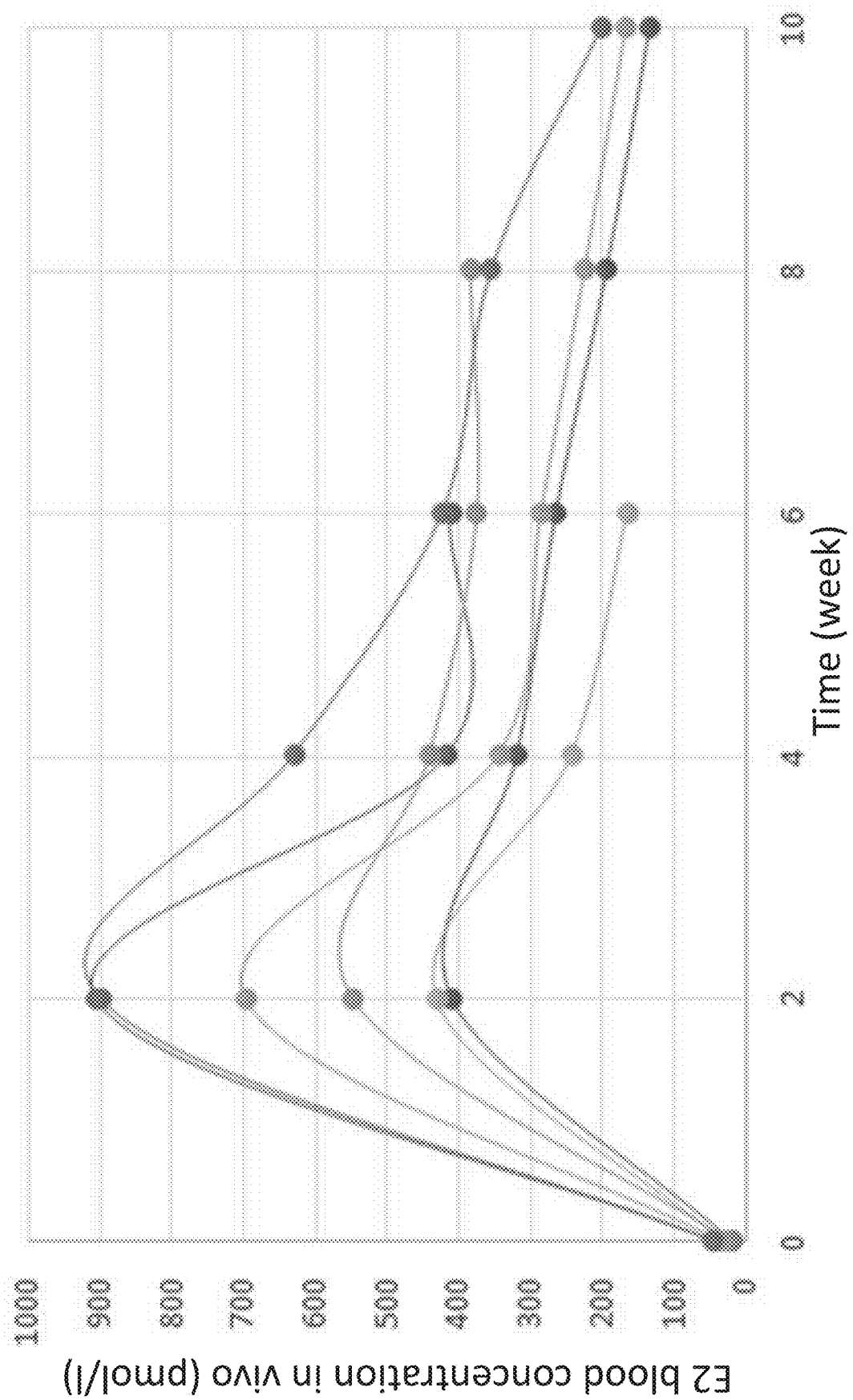
FIG. 13 shows the trend of the blood concentration change in vivo of 6 subjects within 10 weeks after the implantation of the matrix-type elastic sheet formed by a kneading sample containing 50 mg of estradiol.

FIG. 13 shows the trend of the blood concentration change in vivo of 6 subjects within 10 weeks after the implantation of the matrix-type elastic sheet 1' formed by a kneading sample containing 50 mg of estradiol. It can be seen from the FIG. that the blood concentration in the early stage of the implantation is higher, and the later stage is slowed down. The blood concentrations of subjects were measured per 2 weeks, and the trend in vivo matched the release in vitro despite the few of data points.

Figure 14:
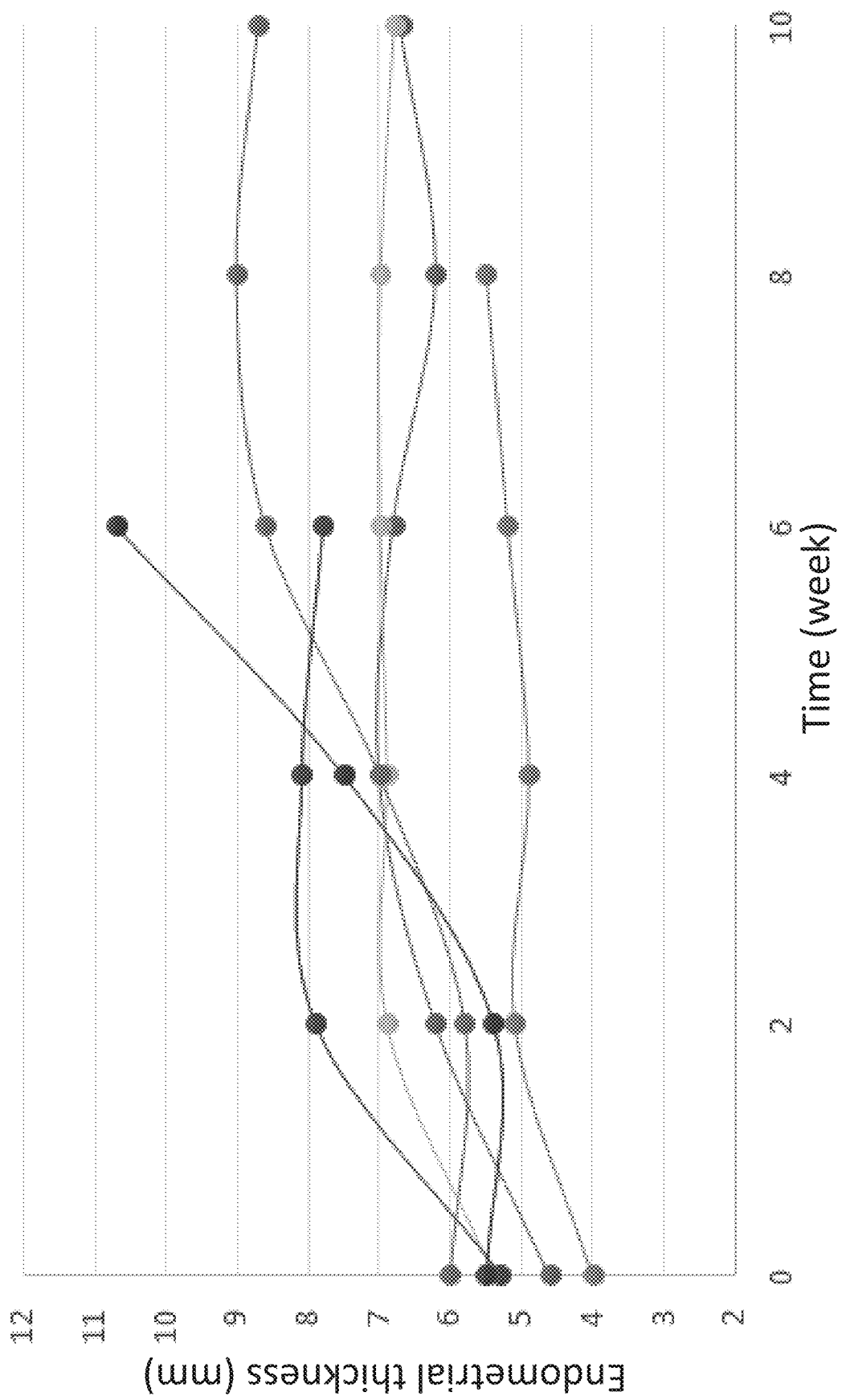
FIG. 14 shows the endometrial thickness change of 6 subjects within 10 weeks after the implantation of the matrix-type elastic sheet formed by a kneading sample containing 50 mg of estradiol.

FIG. 14 shows the endometrial thickness change of 6 subjects within 10 weeks after the implantation of the matrix-type elastic sheet 1' formed by a kneading sample containing 50 mg of estradiol, and the relevant data are shown in the following table:

TABLE 1

| | Week | | | | | | Improvement |
|---|---|---|---|---|---|---|---|
| | 0 | 2 | 4 | 6 | 8 | 10 | |
| A1 | 4.6 | 6.2 | 7 | 6.8 | 6.2 | 6.7 | Active |
| A2 | 5.3 | 7.9 | 8.1 | 7.8 | | | Active |
| A3 | 5.5 | 5.4 | 7.5 | 10.7 | | | Active |
| A4 | 4 | 5.1 | 4.9 | 5.2 | 5.5 | | Inactive |
| A5 | 5.4 | 6.9 | 6.9 | 7 | 7 | 6.8 | Active |
| A6 | 6 | 5.8 | 7 | 8.6 | 9 | 8.7 | Active |

Obviously, the endometrium of the subject was gradually increased, namely the elastic sheet had a significant effect. In fact, the matrix-type elastic sheet 1' formed by a kneading sample containing 50 mg of estradiol is mainly used for patients with moderate adhesion.

Figure 15:
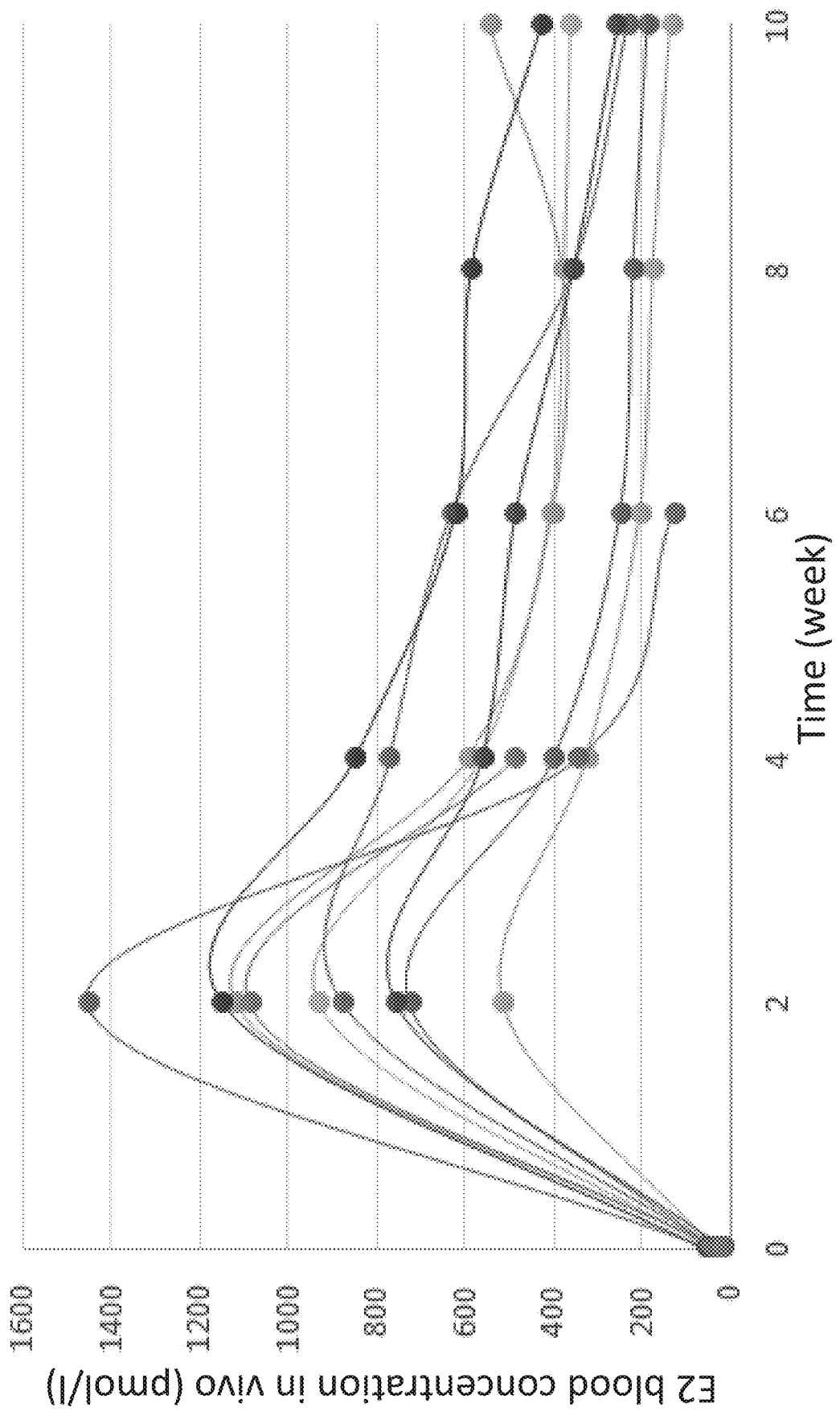
FIG. 15 shows the trend of the blood concentration change in vivo of 9 subjects within 10 weeks after the implantation of the matrix-type elastic sheet formed by a kneading sample containing 100 mg of estradiol.

FIG. 15 shows the trend of the blood concentration change in vivo of 9 subjects within 10 weeks after the implantation of the matrix-type elastic sheet 1" formed by a kneading sample containing 100 mg of estradiol. It can be seen from the FIG. that the blood concentration in the early stage of the implantation is higher, and the later stage is slowed down. The blood concentrations of subjects were measured per 2 weeks, and the trend in vivo matched the release in vitro despite the few of data points.

Figure 16:
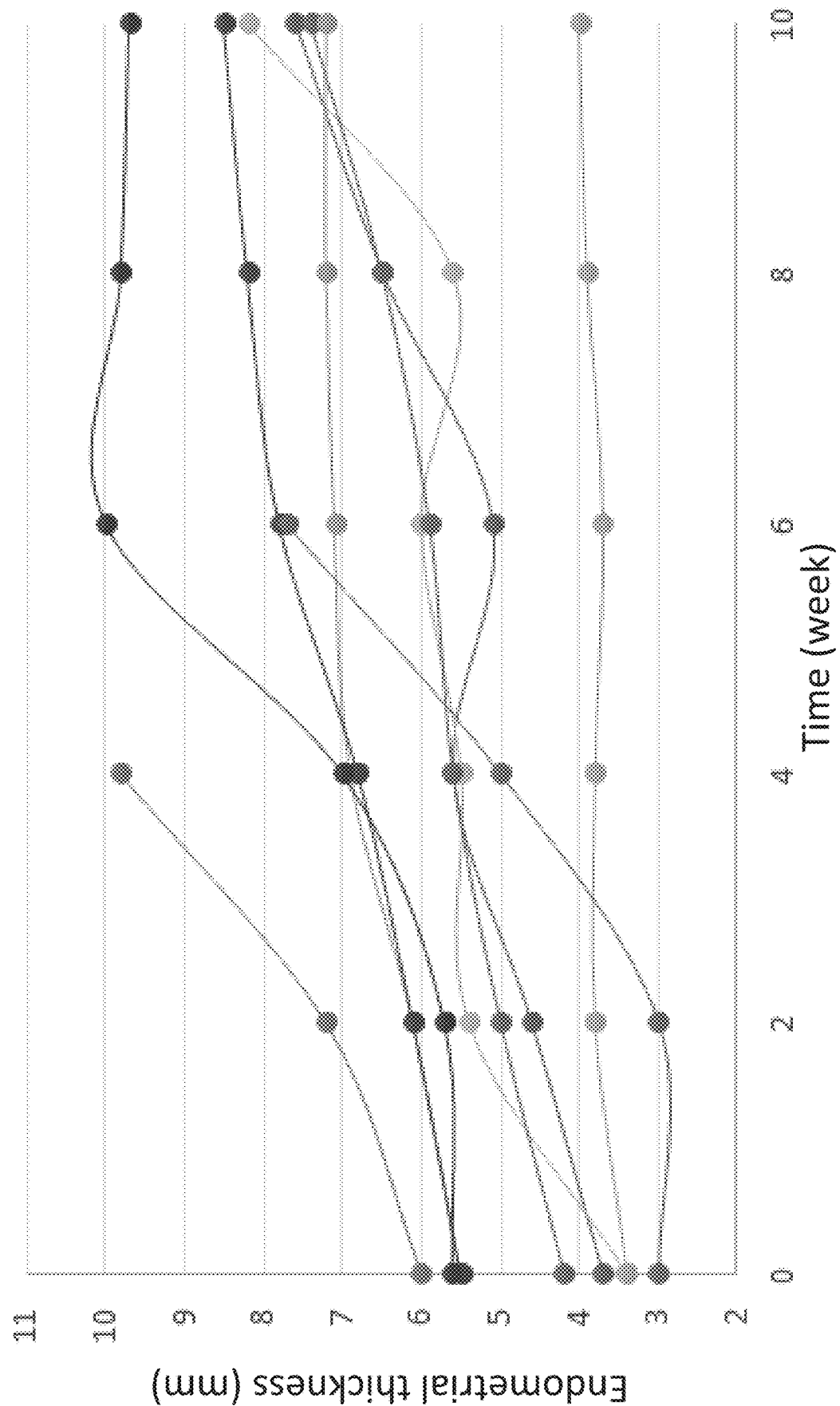
FIG. 16 shows the endometrial thickness change of 9 subjects within 10 weeks after the implantation of the matrix-type elastic sheet formed by a kneading sample containing 100 mg of estradiol.

FIG. 16 shows the endometrial thickness change of 9 subjects within 10 weeks after the implantation of the matrix-type elastic sheet 1" formed by a kneading sample containing 100 mg of estradiol, and the relevant data are shown in the following table:

TABLE 2

| | Week | | | | | | Improvement |
|---|---|---|---|---|---|---|---|
| | 0 | 2 | 4 | 6 | 8 | 10 | |
| B1 | 3.7 | 4.6 | 5.6 | 5.1 | 6.5 | 7.6 | Active |
| B2 | 3.4 | 5.4 | 5.5 | 6 | 5.6 | 8.2 | Active |
| B3 | 4.2 | 5 | 5.6 | 5.9 | 6.5 | 7.4 | Active |
| B4 | 5.5 | 6.1 | 6.9 | 7.1 | 7.2 | 7.2 | Active |
| B5 | 3 | 3 | 5 | 7.7 | | | Active |
| B6 | 3.4 | 3.8 | 3.8 | 3.7 | 3.9 | 4 | Inactive |
| B7 | 6 | 7.2 | 9.8 | | | | Active |
| B8 | 5.5 | 6.1 | 6.8 | 7.8 | 8.2 | 8.5 | Active |
| B9 | 5.6 | 5.7 | 7 | 10 | 9.8 | 9.7 | Active |

Obviously, the endometrium of the subject was gradually increased, namely the elastic sheet had a significant effect. In fact, the matrix-type elastic sheet 1" formed by a kneading sample containing 100 mg of estradiol is mainly used for patients with moderate adhesion.

Figure 17:
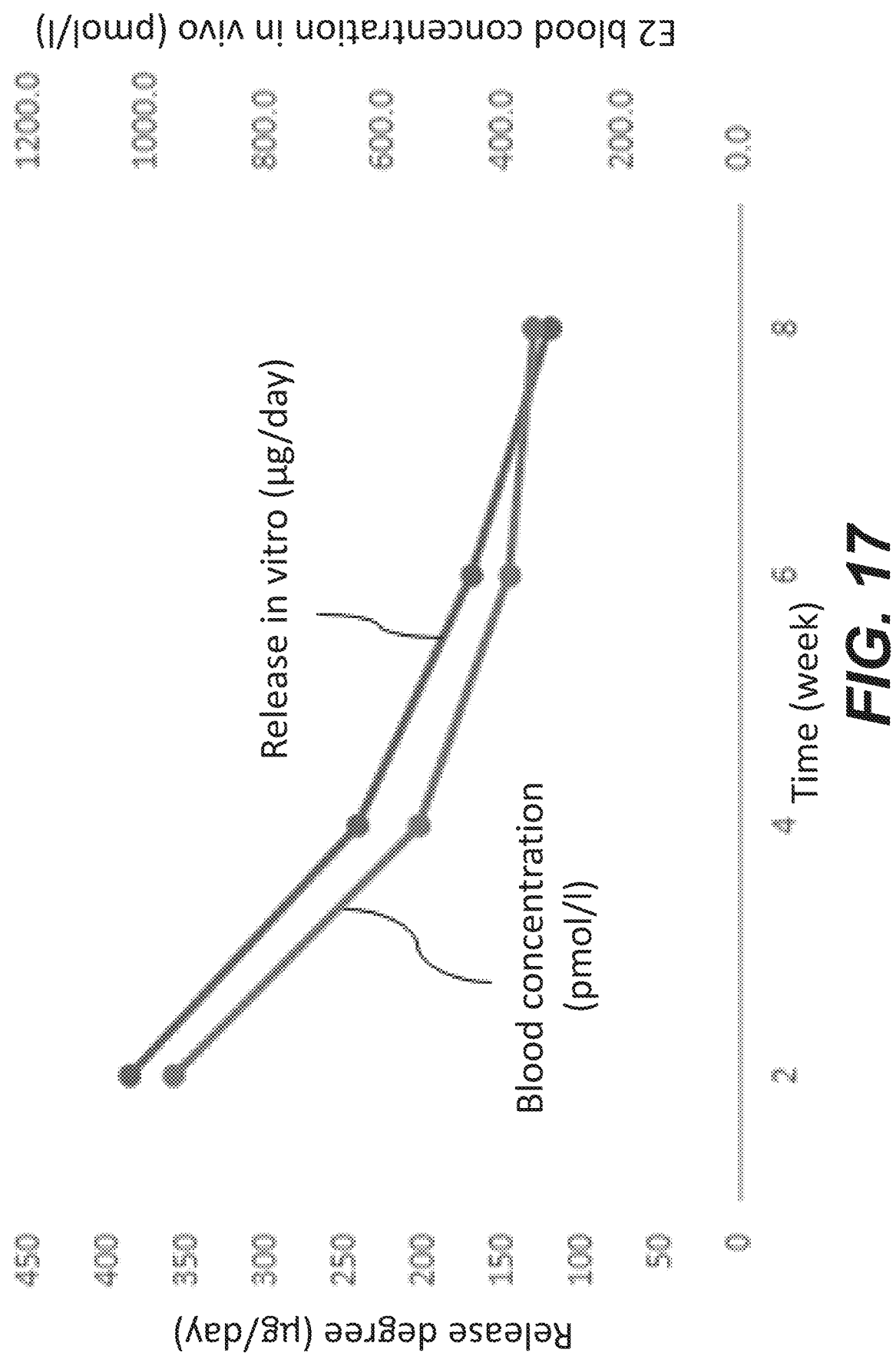
FIG. 17 shows the comparison of the release amount in vitro and the blood concentration in vivo after the implantation of the matrix-type elastic sheet formed by a kneading sample containing 100 mg of estradiol.

FIG. 17 shows the comparison of the release amount in vitro and the blood concentration in vivo after the implantation of the matrix-type elastic sheet 1″ formed by a kneading sample containing 100 mg of estradiol. It can be seen from the FIG. that the blood concentration in vivo is consistent with the release in vitro trend, thus the treatment in vivo can be adjusted by the release in vitro.

The following table gives a comparison of a relationship between the oral dose and the blood concentration in vivo and another relationship between the released drug of the elastic sheet and the blood concentration in vivo:

TABLE 3

| Elastic sheet 1″ | Release amount in vitro (µg/d) | 387 | 243 | 171 | 121 |
|---|---|---|---|---|---|
| | Blood concentration (pmol/l) | 957.7 | 544.8 | 392.1 | 349.6 |
| Oral | Oral dose (µg/d) | 4000 | 3000 | 2000 | 1000 |
| | Blood concentration (pmol/l) | 989.3 | 498.5 | 255.8 | 111.2 |

Obviously, the blood concentration is 989.3 pmol/l by oral administration of 4000 micrograms. The blood concentration can also be 957.7 pmol/l by the elastic sheet of the present disclosure with daily release of 387 micrograms. It shows that 90% of oral drugs have been intercepted by the liver. The elastic sheet can achieve the same effect with less than 1/10 intake drug, in order to prevent the side effects. And drugs can be released steadily in a long-term without drug peaks and troughs, which are very common for the oral daily administration.

Figure 18:
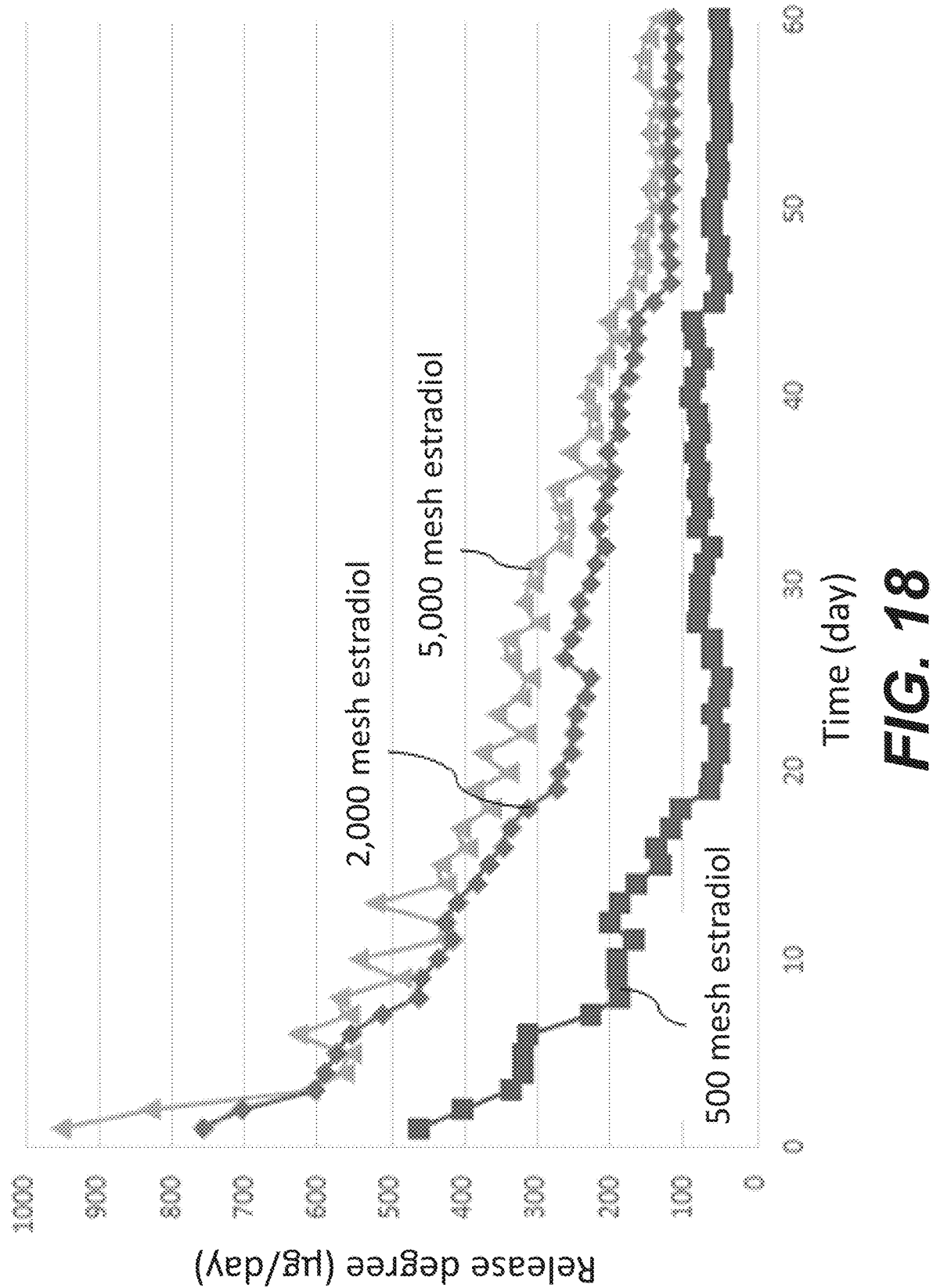
FIG. 18 shows the trend and comparison of release degree in vitro of the matrix-type elastic sheet formed by a kneading sample containing 100 mg of estradiol with different diameters.

FIG. 18 shows the trend and comparison of release degree in vitro of the matrix-type elastic sheet 1″ formed by a kneading sample containing 100 mg of estradiol with different diameters. It can be seen that the big particle is not easy to be released, and the small particle is easier to be released.

Further, drug micronization can be used to control the drug release. The drug with a bigger mesh number and a bigger specific surface area is less likely to be released, and vice versa. For the matrix-type elastic sheet, the mesh number of the drug should be above 500. For the reservoir-type elastic sheet, the mesh number of the drug should be above 1000. For the coating-type elastic sheet, since the drug is loaded on the outside, the range of which can be wider, thus the mesh number of the drug only needs to be above 60.

Figure 19:
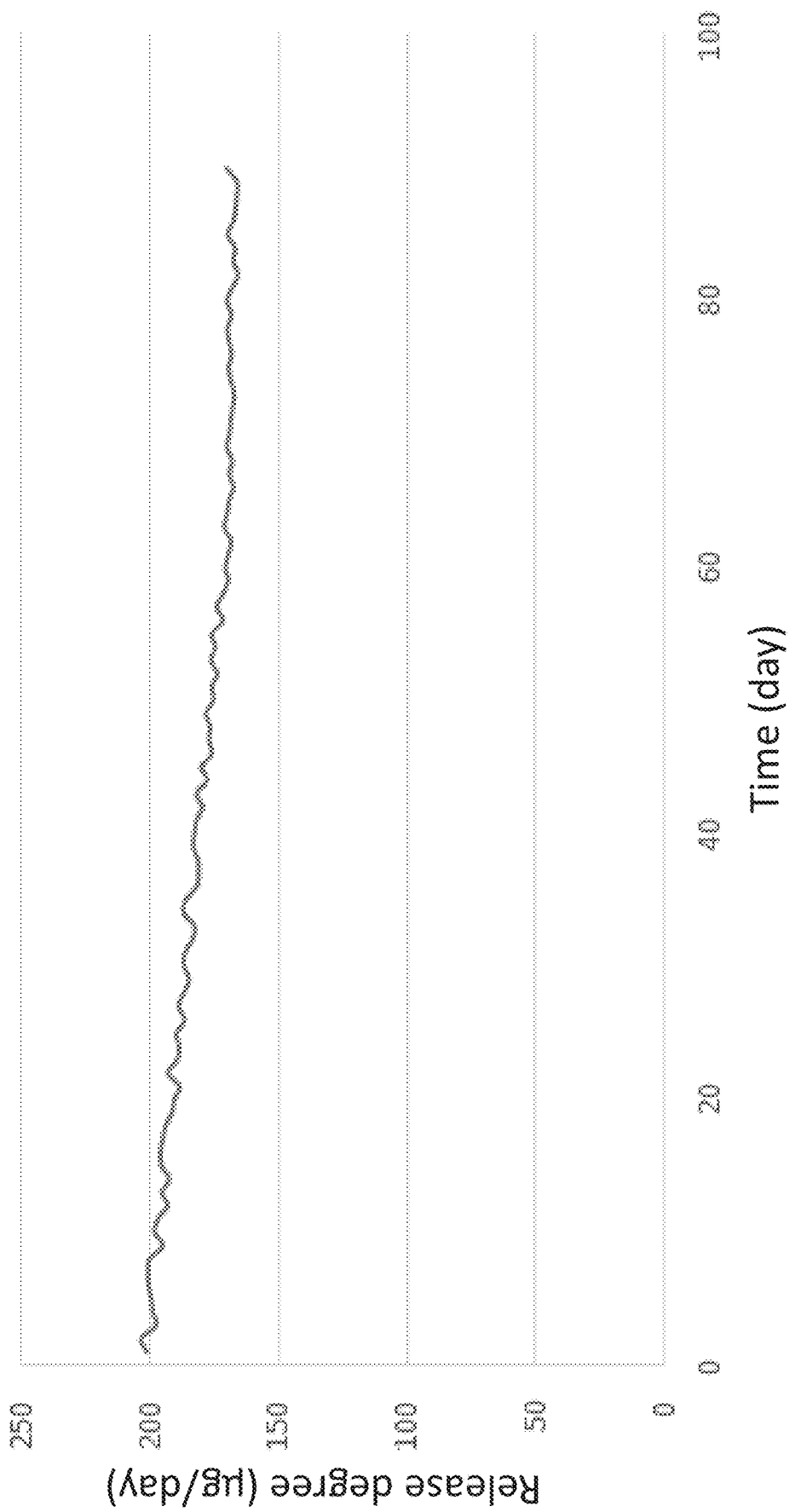
FIG. 19 shows the trend of release in vitro of the reservoir-type elastic sheet formed by a kneading sample containing 100 mg of estradiol.

A reservoir-type elastic sheet 1‴ formed by a kneading sample containing 100 mg of estradiol can be obtained according to the above Example 10. FIG. 19 shows the trend of release in vitro of the reservoir-type elastic sheet 1‴ formed by a kneading sample containing 100 mg of estradiol. It can be seen that compared with the matrix-type elastic sheet, an additional filter is added on the outside of the reservoir-type elastic sheet, so that the release amount is smaller, and the daily drug release is gentle without the sudden release in the early stage of the matrix-type elastic sheet. It is beneficial for long-term drug release in a small dose.

Figure 20:
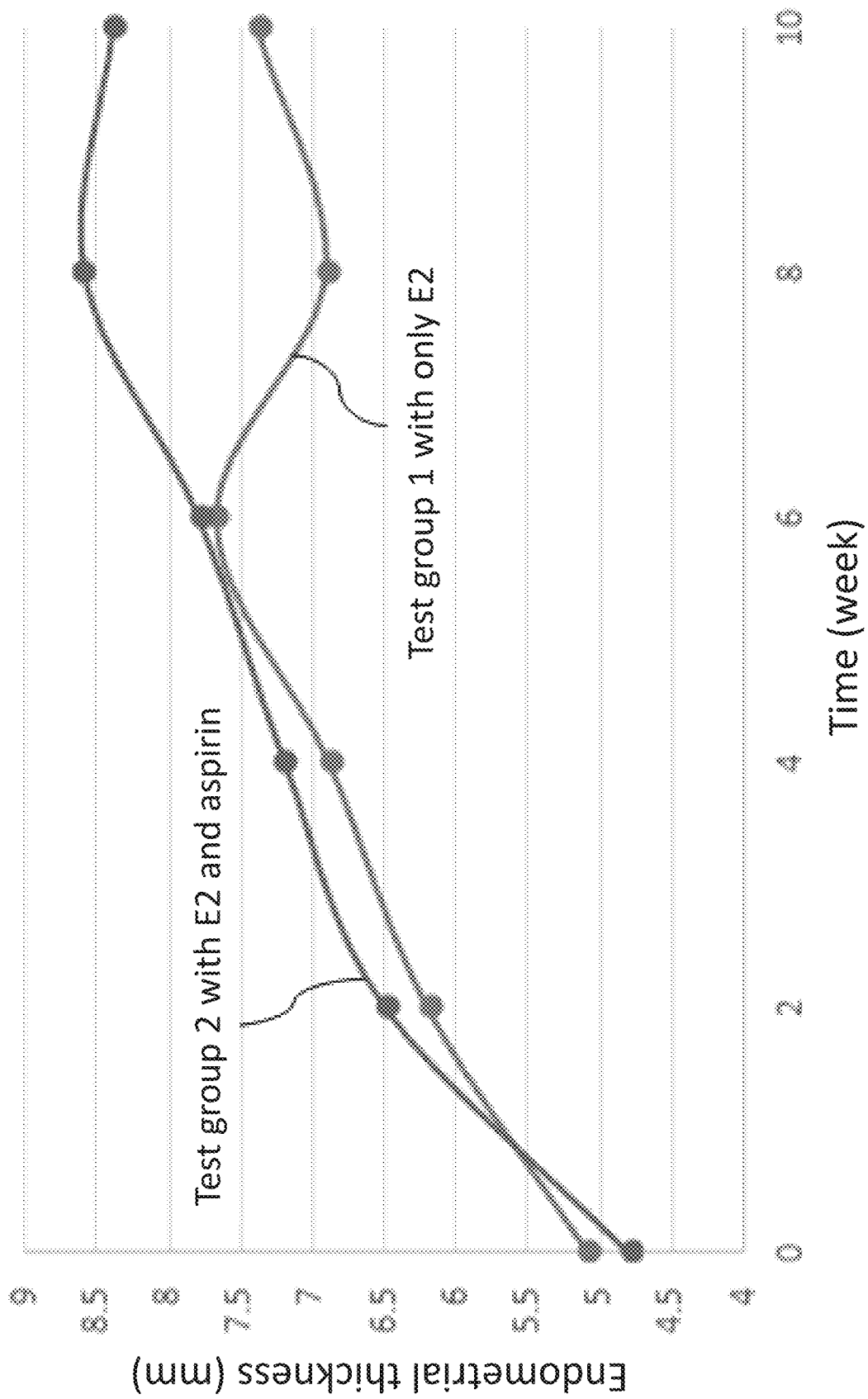
FIG. 20 shows the endometrial thickness change with estradiol alone and with estradiol in the combination with aspirin.

FIG. 20 shows the endometrial thickness change with estradiol alone and with estradiol in the combination with aspirin. There is only E2 in test group 1, and there are E2 and aspirin in test group 2, each group with 6 subjects. The average endometrial growth of the subjects was listed in following table:

TABLE 4

| Drug amount (mg) | | Average release degree in the first 60 days (µg/d) | | Average endometrial thickness within 10 weeks | | | | | |
|---|---|---|---|---|---|---|---|---|---|
| E2 | Aspirin | E2 | Aspirin | 0 | 2 | 4 | 6 | 8 | 10 |
| Test group 1 | | | | | | | | | |
| 50 | 0 | 166 | 0 | 5.1 | 6.2 | 6.9 | 7.7 | 6.9 | 7.4 |
| Test group 1 | | | | | | | | | |
| 50 | 10 | 152 | 42 | 4.8 | 6.5 | 7.2 | 7.8 | 8.6 | 8.4 |

Obviously, at the same dose, by the drug (aspirin) for increasing the blood circulation, the endometrial growth was accelerated, and the endometrium was thicker. That is to say, the estradiol and the drug (aspirin) for increasing the blood circulation provide a synergistic effect.

An elastic sheet is provided. The elastic sheet comprises a silicone film having connecting through-holes, an intervening wire passing though the connecting through-holes of the silicone film, and a thin tube sheathed on the wire. According to one aspect, the cutting force acting on the silicone film from the wire is dispersed by the connecting through-holes and the thin tube sheathed on the wire when the wire passing through the connecting through-holes is pulled. In addition, the edge of the connecting through-hole is provided with a reinforcing portion to further reduce the damage to the silicone film caused by the wire. According to another aspect, the cross section of the elastic sheet after contraction is reduced by the force when the wire is pulled, in order to facilitate the removal from the uterine cavity through the vagina. In addition, the elastic sheet and the placing device are fixed by the wire passing through fixing through-holes of the elastic sheet. Thus, the cross section of the elastic sheet can be reduced when the wire is pulled, which is beneficial to the implantation into the uterus by the placing device, with less damage to the vagina and the uterus.

The present disclosure also provides an elastic sheet. According to one aspect, the cutting force acting on the silicone film from the wire is dispersed by the connecting through-holes and the thin tube sheathed on the wire when the wire passing through the connecting through-holes is pulled. In addition, the edge of the connecting through-hole is provided with a reinforcing portion to further reduce the damage to the silicone film caused by the wire. According to another aspect, the cross section of the elastic sheet is reduced by the force when the wire is pulled, in order to facilitate the removal from the uterine cavity through the vagina. In addition, the elastic sheet and the placing device are fixed by the wire passing through fixing through-holes of the elastic sheet. Thus, the cross section of the elastic sheet can be reduced when the wire is pulled, which is beneficial to the implantation into the uterus by the placing device, with less damage to the vagina and the uterus.

According to some embodiments, the electric sheet comprises a silicone film having connecting through-holes, an intervening wire passing though the connecting through-holes of the silicone film, and a thin tube sheathed on the wire. According to some embodiments, the cutting force acting on the silicone film from the wire is dispersed by the connecting through-holes and the thin tube sheathed on the wire, and thus the damage to the silicone film caused by the wire is reduced. In addition, the silicone film can be removed out the uterus through the vagina by pulling the wire passing through the connecting through-holes.

In some embodiments, the thin tube is sheathed on the wire to reduce the contact between the wire and the silicone film, thereby to reduce the cutting damage to the silicone film caused by the wire. Specifically, the cutting pressure on the elastic sheet is transferred to the thin tube from the wire, in order to avoid excessive shear stress between the connecting through-holes and the crack of the elastic sheet, thus to prevent the removal difficulty.

In some embodiments, there are n connecting through-holes, n≥2, and any two of the connecting through-holes of the silicone film are passed through by two free ends of the wire, which are finally merged to be fixed. The merged and fixed ends of the wire provide a tail wire as a removal wire. The elastic sheet can be removed by the removal wire after the release period or according to the doctor's follow-up evaluation. In some embodiments, an outer contour of the silicone film is bypassed by the free ends of the wire.

In other embodiments, any two of the connecting through-holes of the silicone film are passed through, and an outer contour of the silicone film is bypassed, by the free ends of the wire, which are finally merged into a common connecting through-hole to be fixed. The outer contour here may be any boundary contour of the silicone film. In some embodiments, the outer contour is the trapezoidal waist when the silicone film is or similarly is trapezoidal.

According to some embodiments, any two of the connecting through-holes of the silicone film are passed through by the free ends of the wire, and the cross section of the silicone film can be reduced by the force when the wire is pulled. In some embodiments, an outer contour of the silicone film is bypassed by the free ends of the wire, it could be understood that the connecting through-holes are passed through from the front of the silicone film by the wire, and the lateral side of the silicone film is bypassed back to the front of the silicone film by the wire. On one hand, the cutting force acting on the silicone film from the wire can be shared by the outer contour. On the other hand, the cross section of the silicone film after contraction can be reduced by the force, in order to facilitate the removal through the vagina and out of the uterus.

In some embodiments, there are three connecting through-holes of a first connecting through-hole, a second connecting through-hole and a third connecting through-hole, wherein the first connecting through-hole and the second connecting through-hole are located above the third connecting through-hole. In some embodiments, the three connecting through-holes are arranged in an inverted triangle. In some embodiments, the inverted triangle is an inverted isosceles triangle, and further preferably an inverted equilateral triangle.

In some embodiments, the first connecting through-hole and the second connecting through-hole are passed through from the front of the silicone film by two free ends of the wire, which are finally merged into the third connecting through-hole from the rear of the silicone film to be fixed; or, the first connecting through-hole and the second connecting through-hole are passed through from the front of the silicone film, and an outer contour of the silicone film is bypassed, by two free ends of the wire, which are finally merged into the third connecting through-hole from the front of the silicone film to be fixed.

In some embodiments, the connecting through-holes of the silicone film sheet are triangularly distributed, with good stability and preferable force dispersion. The damage to the silicone film caused by the wire is reduced. The connection force between the wire and the silicone film is increased by the specific intervening manner. Thus, the cross section of the silicone film is reduced by the force when the tail wire is pulled, in order to facilitate the removal through the vagina and out of the uterus.

In some embodiments, the number of the connecting through-holes is ≥2, and the shape formed by the connecting through-holes is not limited to the inverted triangle. The specific shape can be adjusted as desired. In some embodiments, the shape formed by the connecting through-holes is an inverted equilateral triangle. It should be understood that too many holes would generate an excessive tangential stress on the silicone film causing damage to the silicone film when the connecting through-holes are passed through by the wire. In addition, the inverted equilateral triangle structure is stable and is also beneficial to the force dispersion. In some embodiments, the elastic sheet has a thickness of 0.1-4 mm, such as 0.1 mm, 0.5 mm, 1 mm, 1.5 mm, 2 mm, 2.5 mm, 3 mm, 3.5 mm, 4 mm, etc., preferably 0.2-1 mm.

In some embodiments, the elastic sheet has a shape of an inverted trapezoid. In some embodiments, the inverted trapezoid has a height of 25-35 mm (such as 25 mm, 26 mm, 27 mm, 28 mm, 29 mm, 30 mm, 31 mm, 32 mm, 33 mm, 34 mm, 35 mm, etc.), an upper bottom of 20-40 mm (such as 20 mm, 22 mm, 25 mm, 28 mm, 30 mm, 32 mm, 35 mm, 37 mm, 40 mm, etc.), and a lower bottom of 5-15 mm (such as 5 mm, 6 mm, 7 mm, 8 mm, 9 mm, 10 mm, 11 mm, 12 mm, 13 mm, 14 mm, 15 mm, etc.).

In some embodiments, the elastic sheet has a shape with a big upper end and a small lower end, preferably an inverted trapezoid. After the implantation, the upper end corresponds to the uterine fundus, and the lower end corresponds to the uterine cervix at an intrauterine opening. The shape of the elastic sheet is adapted to the physiological shape and size of the uterus to isolate the anterior and posterior walls of the uterus as completely as possible, so that the contact between the anterior and posterior walls of the uterus is minimized.

In some embodiments, an edge of the connecting through-hole is provided with a reinforcing portion. In some embodiments, the reinforcing portion is a thickened portion. In some embodiments, the thickened portion has a thickness of 0.2-2 mm. The thickness of the thickened portion in some embodiments means the thickness without the elastic sheet.

In some embodiments, the reinforcing portion arranged at the edge of the connecting through-hole is also to reduce the cutting damage to the silicone film caused by the wire to prevent the too large cutting stress between the connecting through-holes, in order to prevent the crack of the silicone film at the connecting through-holes by the wire, and thus to avoid the removal difficulty.

In some embodiments, the connecting through-hole has a circular shape. In some embodiments, connecting through-hole has a diameter of 0.3-1.2 mm (such as 0.3 mm, 0.4 mm, 0.5 mm, 0.6 mm, 0.7 mm, 08 mm, 0.9 mm, 1.0 mm, 1.1 mm, 1.2 mm, etc.), and the diameter of the connecting through-hole is larger than a diameter of the wire. In some embodiments, the diameter of the wire is 0.1-1 mm, preferably 0.2-0.5 mm.

In some embodiments, the thin tube is an elastic tube. In some embodiments, the thin tube is a silicone tube. In other embodiments, the thin tube may be coated or mixed with a drug that is the same as the drug loaded on the silicone film for drug sustained release in the uterine cavity. In some embodiments, the thin tube is sheathed on the wire between any two connecting through-holes. In some embodiments, the thin tube has a diameter larger than a diameter of the connecting through-hole.

In some embodiments, the wire is formed of any one or at least two of following materials: polypropylene, polyethylene, polyester and polyamide. In some embodiments, the wire is a yarn with a good biocompatibility, preferably a non-degradable sewing thread.

In some embodiments, a minimum vertical distance between the connecting through-hole and a lower bottom of the silicone film is 0.5-4 mm, such as 0.5 mm, 1 mm, 2 mm, 3 mm, 4 mm, etc. In some embodiments, a maximum vertical distance between the connecting through-hole and the lower bottom of the silicone film is 1-8 mm, such as 1 mm, 2 mm, 3 mm, 4 mm, 5 mm, 6 mm, 7 mm, 8 mm, etc. In some embodiments, a line connecting any two of the connecting through-holes has a maximum horizontal distance of 2-10 mm on a lower bottom of the silicone film, such as 2 mm, 3 mm, 4 mm, 5 mm, 6 mm, 7 mm, 8 mm, 9 mm, 10 mm, etc., preferably 3-6 mm. In some embodiments, the horizontal distance means that the oblique distance is converted into a horizontal distance parallel to the lower bottom of the silicone film. If the line connecting the two connecting through-holes is parallel to the lower bottom of the silicone film, the distance between the connecting through-holes is the horizontal distance. If the line connecting the two connecting through-holes is not parallel to the lower bottom of the silicone film, the line connecting the two connecting through-holes is deems as a hypotenuse which is mapped on the lower bottom of the silicone film, and the mapped distance on the lower bottom is the horizontal distance.

In some embodiments, the elastic sheet can be pulled out of the uterus if necessary after the release period, wherein the connecting through-holes may be as close as possible to the end of the cervix opening, in order to facilitate the removal of the elastic sheet.

In some embodiments, the silicone film further includes two fixing through-holes, wherein the elastic sheet is fixed to the placing device by a wire passing through the fixing through-holes. In some embodiments, the elastic sheet is implanted into the uterine cavity with the assistance of a placing device.

In some embodiments, the elastic sheet can be contracted into a cylindrical shape if necessary. The contracted elastic sheet can be delivery through the cervical canal into the uterus by a tube, and then be stretched after the implantation. Since the silicone rubber has glutinousness which prevents the contracted elastic sheet from being pushed out, the medical silicone oil can be applied at an end of the contracted elastic sheet to increase the lubrication between the sheet and the tube.

In some embodiments, an edge of the fixing through-hole is provided with a reinforcing portion. In some embodiments, the reinforcing portion is a thickened portion. In some embodiments, the thickened portion has a thickness of 0.2-2 mm, such as 0.2 mm, 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm, 1.5 mm, 1.6 mm, 1.7 mm, 1.8 mm, 1.9 mm, 2.0 mm, etc.

In some embodiments, the reinforcing portion arranged at the edge of the fixing connecting through-hole is also to reduce the cutting damage to the silicone film caused by the wire to prevent the two large cutting stress between the fixing through-holes, in order to prevent the crack of the silicone film at the fixing through-holes by the wire and the fixing failure between the silicone film and the placing device, and thus to avoid the implantation difficulty. In some embodiments, the fixing through-hole has a circular shape. In some embodiments, the fixing through-hole has a diameter of 0.3-1.5 mm, such as 0.2 mm, 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm, 1.5 mm, etc., and the diameter of the fixing through-hole is larger than a diameter of the wire.

In some embodiments, the placing device is in a shape of a rod, and a maximum distance between any two points of a periphery of a cross section of the rod is 3-7 mm, such as 3 mm, 4 mm, 5 mm, 6 mm, 7 mm, etc., preferably 4-6 mm. In some embodiments, the distance between two fixing through-holes is not less than the maximum distance between any two points of a periphery of a cross section of the rod of the placing device. In some embodiments, a vertical distance between the fixing through-hole and an upper bottom of the silicone film is 2-8 mm, such as 2 mm, 3 mm, 4 mm, 5 mm, 6 mm, 7 mm, 8 mm, etc. In some embodiments, the vertical distances between the two fixing through-holes and the upper bottom of the silicone film are the same.

Compared with the prior art, the elastic sheet of the present disclosure provides several beneficial effects. According to one aspect, the cutting force acting on the silicone film from the wire is dispersed by the connecting through-holes and the thin tube sheathed on the wire when the wire passing through the connecting through-holes is pulled. In addition, the edge of the connecting through-hole is provided with a reinforcing portion to further reduce the damage to the silicone film caused by the wire. According to another aspect, the cross section of the elastic sheet after contraction is reduced by the force when the wire is pulled, in order to facilitate the removal from the uterine cavity through the vagina. In addition, the elastic sheet and the placing device are fixed by the wire passing through fixing through-holes of the elastic sheet. Thus, the cross section of the elastic sheet can be reduced when the wire is pulled, which is beneficial to the implantation into the uterus by the placing device, with less damage to the vagina and the uterus.

Figure 32:
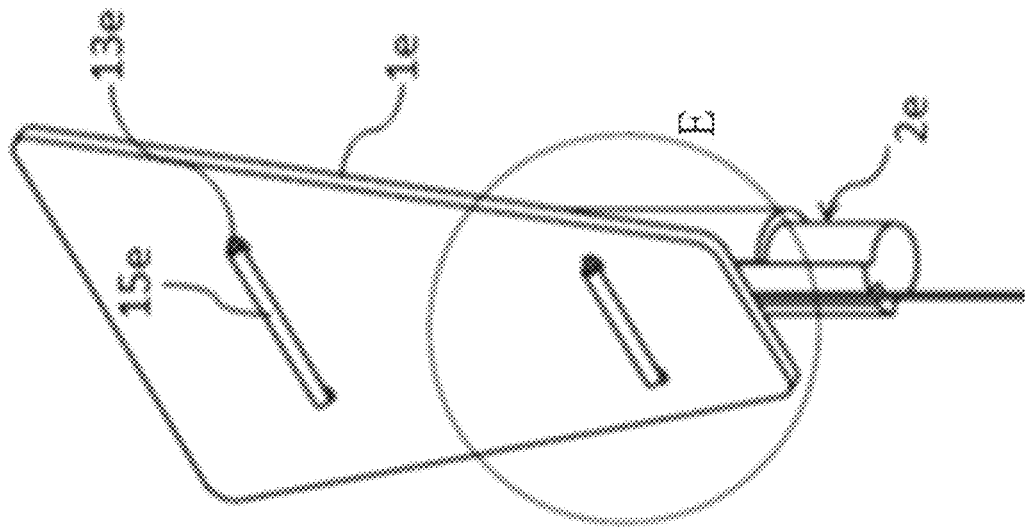
FIG. 32 is a schematic view of an elastic sheet according to an Embodiment 7.
Figure 34:
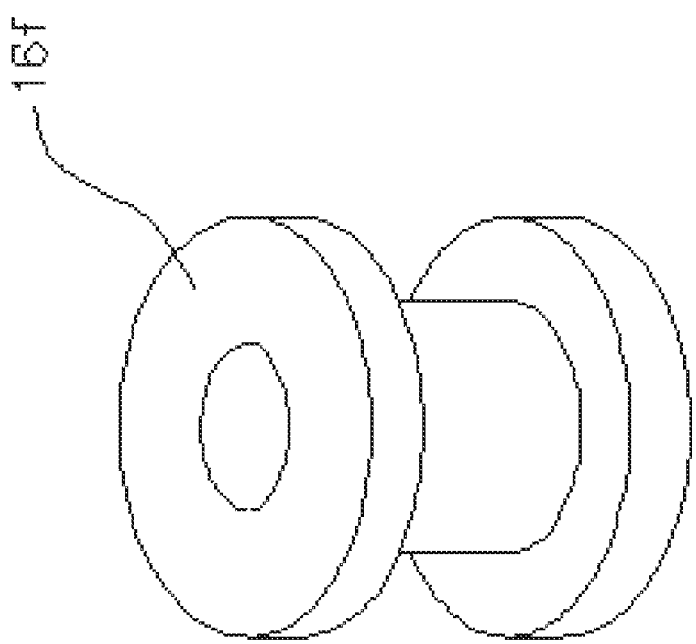
FIG. 34 is a schematic view of a reinforcing portion in the Embodiment 7.
Figure 33:
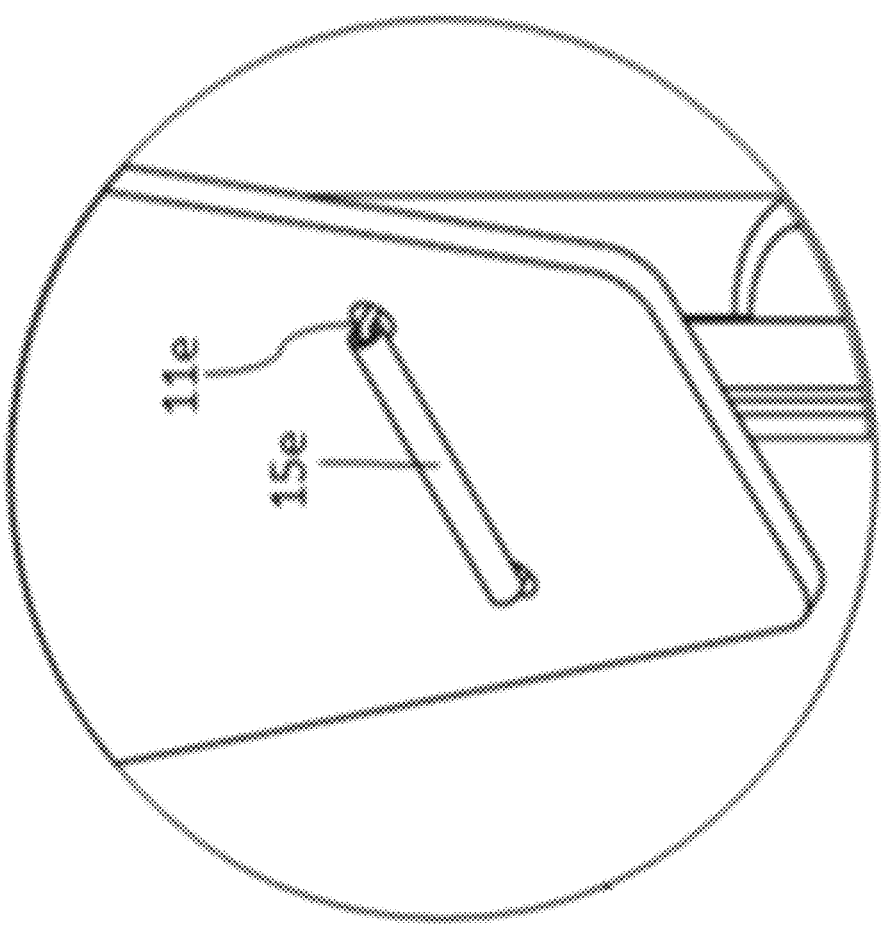
FIG. 33 is an enlarged view of an area E of FIG. 32.

FIGS. 21-31 show various embodiments in which 1 indicates a first connecting through-hole, 2 indicates a second connecting through-hole, 3 indicates a third connecting through-hole, 4 indicates a silicone film, 5 indicates a wire, and 6 indicates a thin tube. FIGS. 32-33 show various embodiments in which 1*e* indicates a silicone film, 2*e* indicates a delivery device, 11*e* indicates a removal wire, 13*e* indicates an implant wire, 15*e* indicates a thin tube. FIG. 34 shows an embodiment in which 16*f* indicates a reinforcing portion of a rivet structure. FIGS. 35-40 show various embodiments in which 1 indicates a first connecting through-hole, 2 indicates a second connecting through-hole, 3 indicates a third connecting through-hole, 4 indicates a silicone film, 5 indicates a wire, and 6 indicates a thin tube.

Embodiment 1

The present embodiment provides an elastic sheet, including: a silicone film having connecting through-holes (also referred to as tail wire holes), an intervening wire (also referred to as a removal wire) passing though the connecting through-holes of the silicone film, and a thin tube sheathed on the wire.

Figure 22:
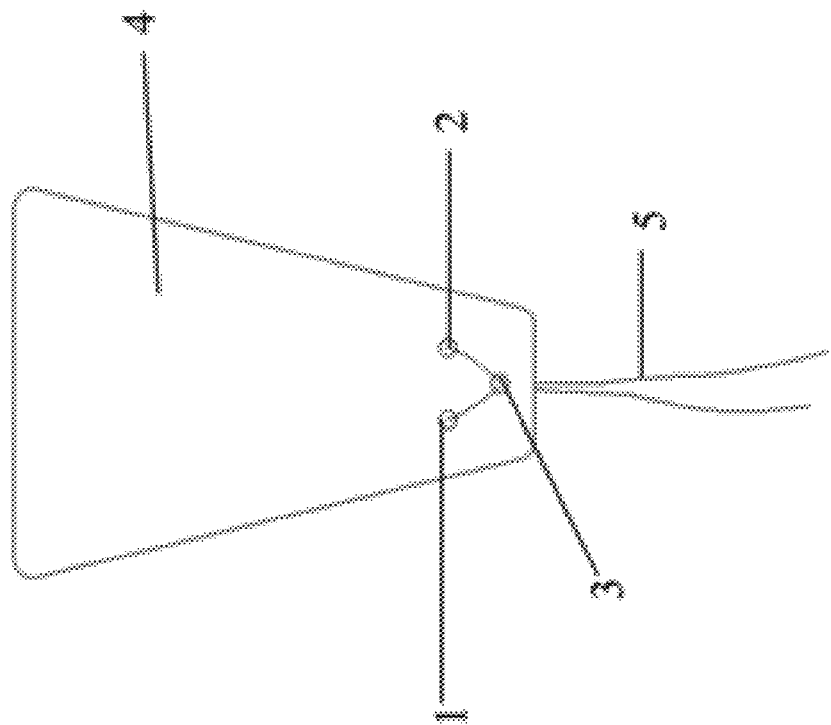
FIG. 22 is a rear view of the Embodiment 1 elastic sheet.
Figure 21:
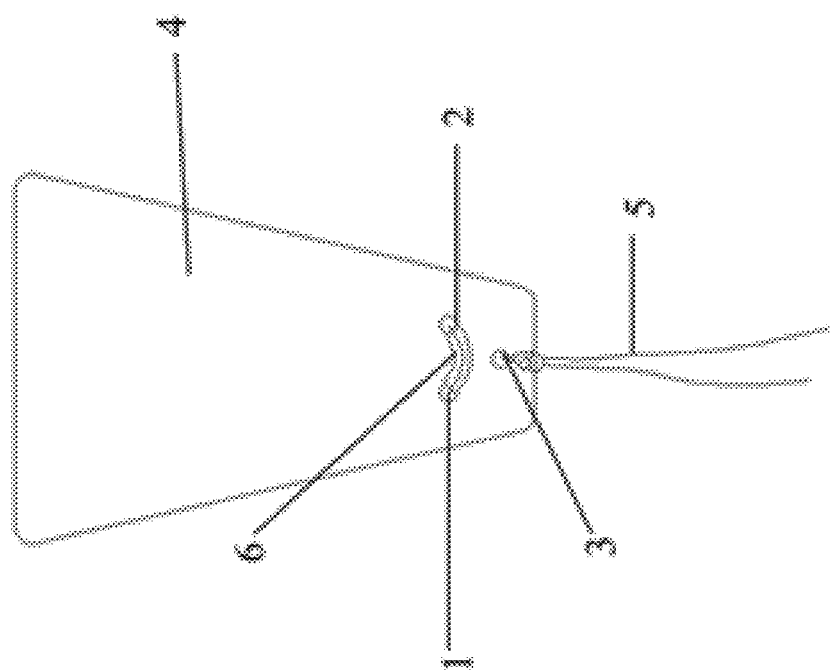
FIG. 21 is a front view of an elastic sheet according to an Embodiment 1.

As shown in FIG. 21 and FIG. 22, there are three connecting through-holes, namely a first connecting through-hole 1, a second connecting through-hole 2 and a third connecting through-hole 3, which are distributed in an inverted equilateral triangle shape, wherein the first connecting through-hole 1 and the second connecting through-hole 2 are located above the third connecting through-hole 3. The silicone film 4 is an inverted trapezoid shape, with the height of 25 mm, an upper bottom length of 20 mm, and a lower bottom length of 15 mm. A vertical distance between the first connecting through-hole 1 (or the second connecting through-hole 2) and the lower bottom of the silicone film 4 is 5 mm. A vertical distance between the third connecting through-hole 3 and the lower bottom of the silicone film 4 is 2 mm. Each of the connecting through-holes 1, 2, 3 is circular, with the diameter of 1.2 mm. The diameter of the connecting through-hole is larger than 1 mm, which is the diameter of the wire 5. The wire 5 is a monofilament single-strand sewing thread. The thin tube 6 sheathed on the wire 5 between the first connecting through-hole 1 and the second connecting through-hole 2 is a silicone tube. The diameter of the silicone tube is larger than the connecting through-hole. The first connecting through-hole 1 and the second connecting through-hole 2 are passed through from the front of the silicone film 4 by two free ends of the wire 5, which are finally merged into the third connecting through-hole 3 from the rear of the silicone film 4 to be fixed.

A smaller cross section of the elastic sheet of the present embodiment can be obtained by pulling the fixed end of the wire 5, wherein the wire 5 between the first connecting through-hole 1 and the second connecting through-hole 2 is stressed by continuously tightening the wire 5 by virtue of the third connecting through-hole 3. The contact area with the silicone film 4 is increased by the elastic silicone thin tube 6 sheathed on the wire 5 between the first connecting through-hole 1 and the second connecting through-hole 2, and thus the cutting force acting on the silicone film 4 from the wire 5 is reduced and the connection force between the wire 5 and the silicone film 4 is increased. The connection force was measured four times in succession (i.e., the silicone film 4 and the wire 5 were fixed to a stretching machine used to measure the force values required for the crack of the silicone film). The force values were 4.2 N, 5.2 N, 4.8 N, and 4.1 N, with the average value of 4.6 N. It shows that the connection force between the wire 5 and the silicone film 4 of the elastic sheet can be increased, and the cross section of the silicone film 4 can be reduced to facilitate the implantation into the uterus.

Embodiment 2

The present embodiment provides an elastic sheet, including: a silicone film having connecting through-holes, an intervening removal wire passing though the connecting through-holes of the silicone film, and a thin tube sheathed on the removal wire between the connecting through-holes.

Figure 23:
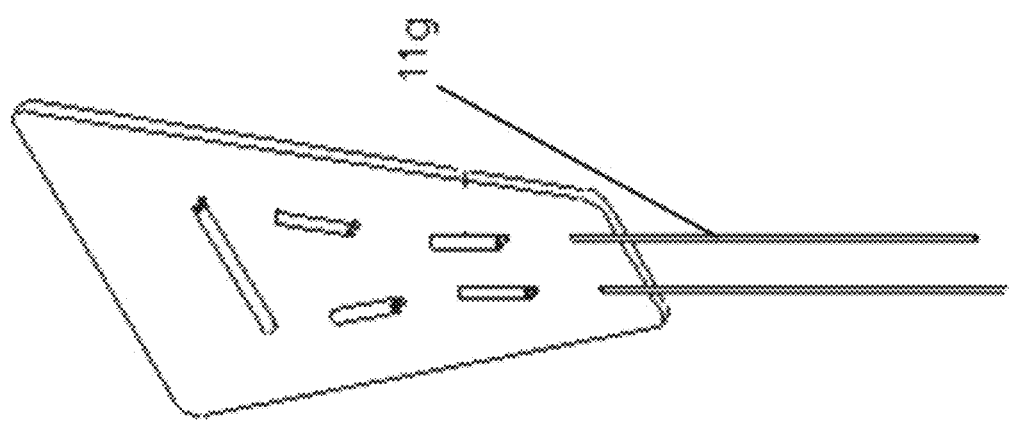
FIG. 23 is a front view of an elastic sheet according to an Embodiment 2.

As shown in FIG. 23, there are twelve connecting through-holes. The twelve connecting through-holes of the silicone film are passed through by two free ends of the removal wire 11g. A thin tube is sheathed on the removal wire 11g between any two of the connecting through-holes.

In the elastic sheet of the present embodiment, the removal wire 11g between the two connecting through-holes is stressed by pulling the fixed end of the removal wire 11g and continuously tightening the removal wire 11g. The contact area with the silicone film is increased by the elastic silicone tube sheathed on the removal wire 11g between the two connecting through-holes, and thus the cutting force acting on the silicone film from the removal wire 11g is reduced. The connection force was measured four times in succession. The force values were 6.0N, 5.8N, 6.2N, and 5.5N, with the average value of 5.9N. It shows that a plurality of connecting through-holes is beneficial to the force dispersion to provide a bigger connection force. However, the overall shearing stress on the silicone film would be affected by the plurality of connecting through-holes, and the reduction of the cross section of the silicone film is limited, thus the delivery of the elastic sheet is a bit poor.

Embodiment 3

The present embodiment provides an elastic sheet, including: a silicone film having connecting through-holes, an intervening wire passing though the connecting through-holes of the silicone film, and a thin tube sheathed on the wire.

Figure 24:
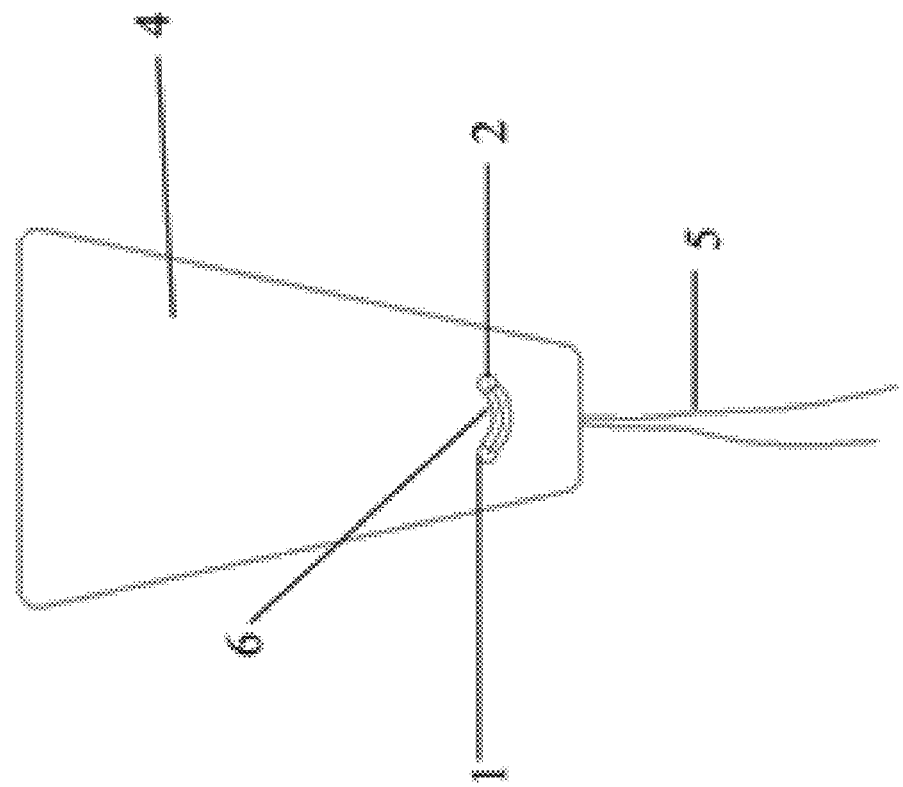
FIG. 24 is a front view of an elastic sheet according to an Embodiment 3.
Figure 25:
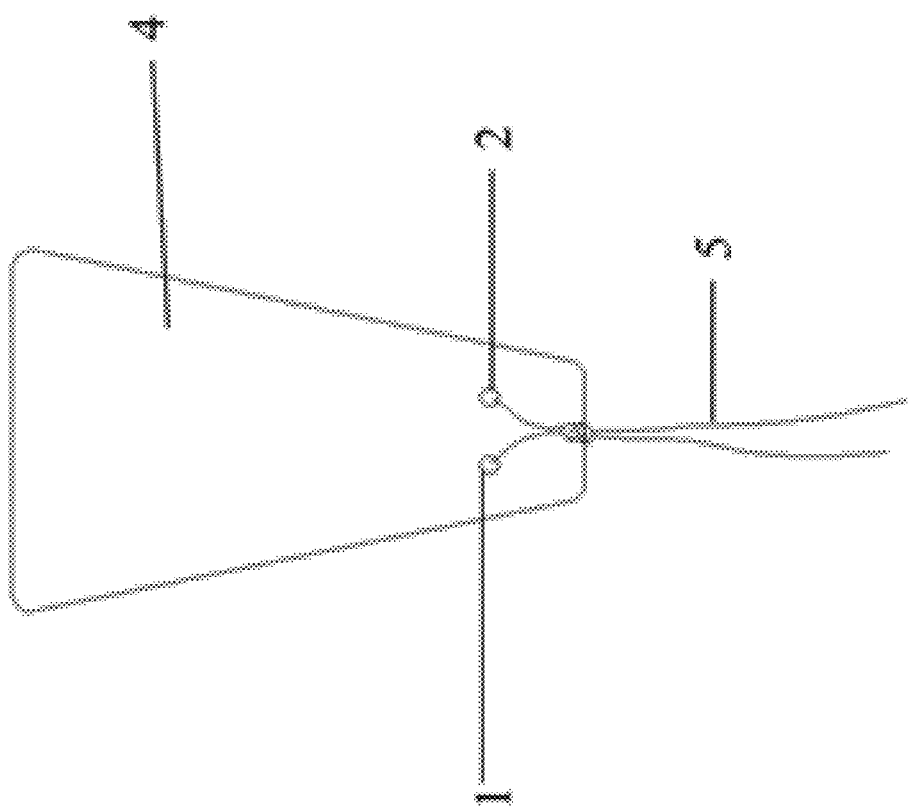
FIG. 25 is a rear view of the Embodiment 3 elastic sheet.

As shown in FIG. 24 and FIG. 25, there are two connecting through-holes, namely a first connecting through-hole 1 and a second connecting through-hole 2, wherein the line connecting first connecting through-hole 1 to the second connecting through-hole 2 is parallel to the bottom of the silicone film 4. The silicone film 4 is an inverted trapezoid shape, with the height of 25 mm, an upper bottom length of 20 mm, and a lower bottom length of 15 mm. A vertical distance between the first connecting through-hole 1 (or the second connecting through-hole 2) and the lower bottom of the silicone film 4 is 6 mm. Each of the connecting through-holes 1, 2 is circular, with the diameter of 1.0 mm. The diameter of the connecting through-hole is larger than 0.8 mm, which is the diameter of the wire 5. The wire 5 is a monofilament single-strand sewing thread. The thin tube 6 sheathed on the wire between the first connecting through-hole 1 and the second connecting through-hole 2 is a silicone tube. The diameter of the silicone tube is larger than the connecting through-hole. The first connecting through-hole 1 and the second connecting through-hole 2 are passed by two free ends of the wire 5, which are finally merged to be fixed.

A smaller cross section of the elastic sheet of the present embodiment can be obtained by pulling the fixed end of the wire 5, wherein the wire 5 between the first connecting through-hole 1 and the second connecting through-hole 2 is stressed by continuously tightening the wire 5. The contact area with the silicone film 4 is increased by the elastic silicone tube 6 sheathed on the wire 5 between the first connecting through-hole 1 and the second connecting through-hole 2, and thus the cutting force acting on the silicone film 4 from the wire 5 is reduced. The connection force was measured four times in succession. The force values were 4.1 N, 4.4 N, 3.7 N, and 4.1 N, with the average value of 4.1 N. It shows that the two connecting through-holes 1, 2 are beneficial to the force dispersion to provide a bigger connection force. In addition, the cross section of the silicone film can be reduced by the force, thus the delivery of the elastic sheet is preferable.

Embodiment 4

The present embodiment provides an elastic sheet, including: a silicone film having connecting through-holes, an intervening wire passing though the connecting through-holes of the silicone film, and a thin tube sheathed on the wire.

Figure 26:
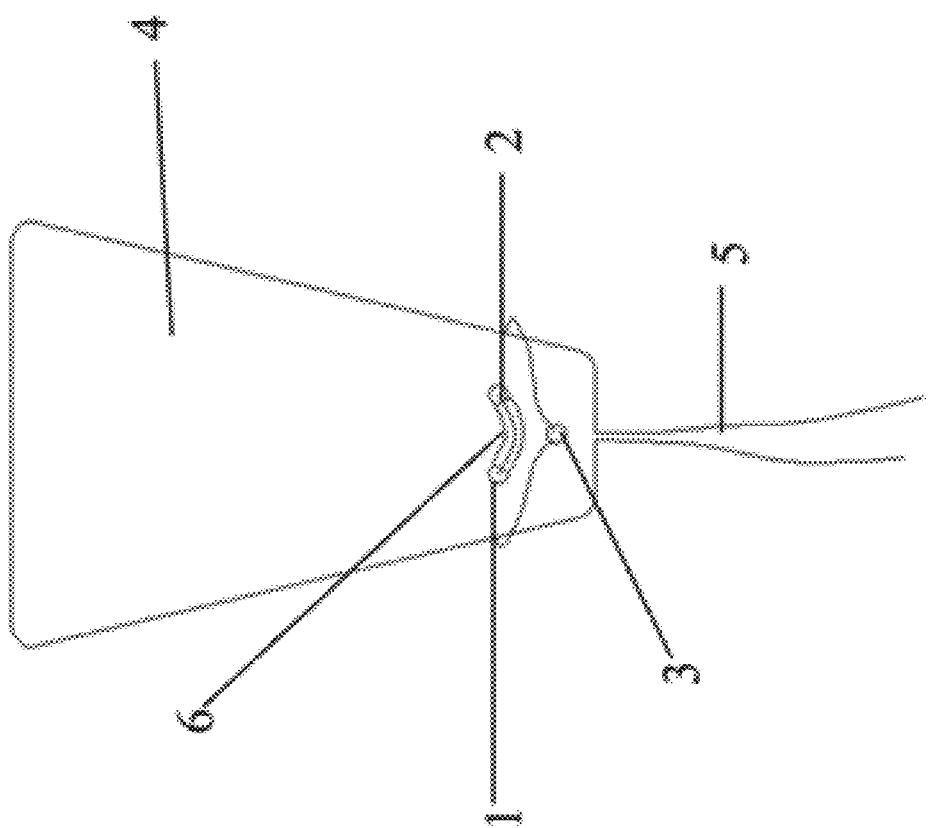
FIG. 26 is a front view of an elastic sheet according to an Embodiment 4.
Figure 27:
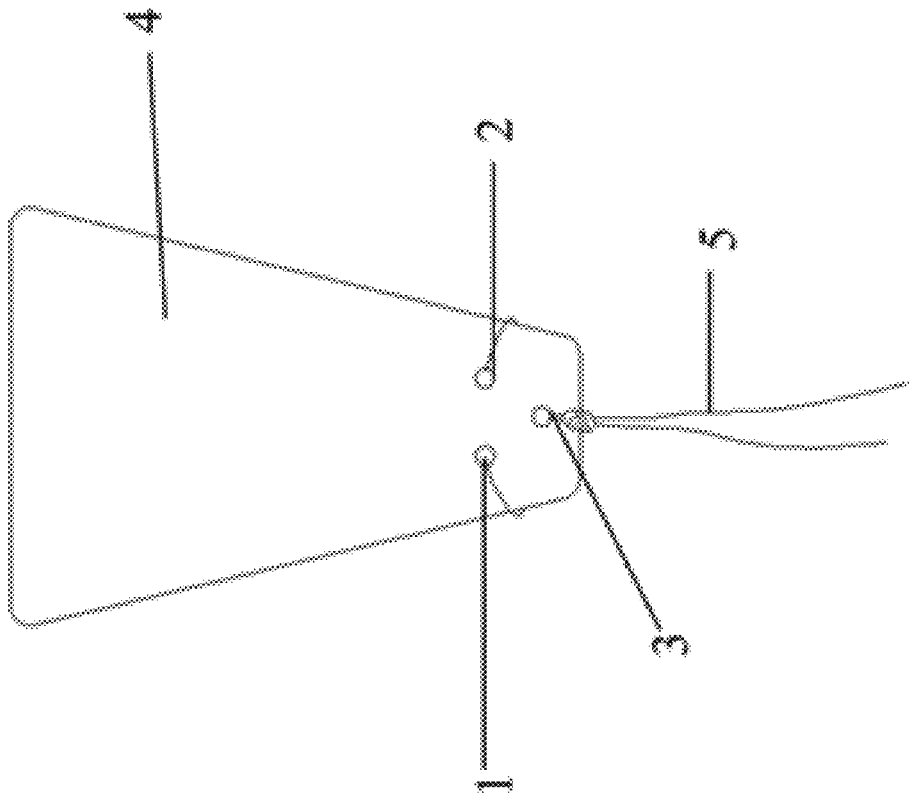
FIG. 27 is a rear view of the Embodiment 4 elastic sheet.

As shown in FIG. 26 and FIG. 27, there are three connecting through-holes, namely a first connecting through-hole 1, a second connecting through-hole 2 and a third connecting through-hole 3, which are distributed in an inverted equilateral triangle shape, wherein the first connecting through-hole 1 and the second connecting through-hole 2 are located above the third connecting through-hole 3. The silicone film 4 is an inverted trapezoid shape, with the height of 30 mm, an upper bottom length of 30 mm, and a lower bottom length of 10 mm. A vertical distance between the first connecting through-hole 1 (or the second connecting through-hole 2) and the lower bottom of the silicone film 4 is 5 mm. A vertical distance between the third connecting through-hole 3 and the lower bottom of the silicone film 4 is 2 mm. Each of the connecting through-holes 1, 2, 3 is circular, with the diameter of 0.6 mm. The diameter of the connecting through-hole is larger than 0.5 mm, which is the diameter of the wire 5. The wire 5 is a monofilament single-strand sewing thread. The thin tube 6 sheathed on the wire between the first connecting through-hole 1 and the second connecting through-hole 2 is a silicone tube. The diameter of the silicone tube is larger than the diameter of the connecting through-hole. The first connecting through-hole 1 and the second connecting through-hole 2 are passed through from the front of the silicone film 4, and an outer contour of the silicone film 4 is bypassed, by two free ends of the wire 5, which are finally merged into the third connecting through-hole 3 from the front of the silicone film 4 to be fixed.

A smaller cross section of the elastic sheet of the present embodiment can be obtained by pulling the fixed end of the wire 5, wherein the outer contour of lateral sides of the silicone film 4 are pressed by the wire 5 and the wire 5 between the first connecting through-hole 1 and the second connecting through-hole 2 is stressed by continuously tightening the wire 5 by virtue of the third connecting through-hole 3. The contact area with the silicone film 4 is increased by the elastic silicone tube 6 sheathed on the wire 5 between the first connecting through-hole 1 and the second connecting through-hole 2, and thus the cutting force acting on the silicone film 4 from the wire 5 is reduced. The connection force was measured four times in succession. The force values were 6.2 N, 5.9 N, 6.9 N, and 6.0 N, with the average value of 6.3 N. It shows that the connection force between the wire 5 and the silicone film 4 is increased, and the cutting damage to the silicone film 4 caused by the wire 5 is reduced. In addition, the pressure on the outer contour of lateral sides of the silicone film 4 caused by tightening the wire 5 can reduce the cross section of the silicone film 4 to facilitate the implantation into the uterus.

Embodiment 5

The present embodiment provides an elastic sheet, including: a silicone film having connecting through-holes, an intervening wire passing though the connecting through-holes of the silicone film, and a thin tube sheathed on the wire.

Figure 28:
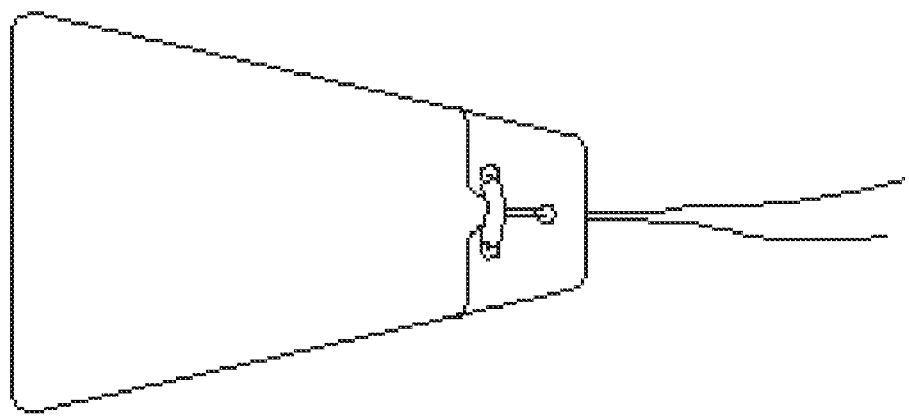
FIG. 28 is a front view of an elastic sheet according to an Embodiment 5.
Figure 29:
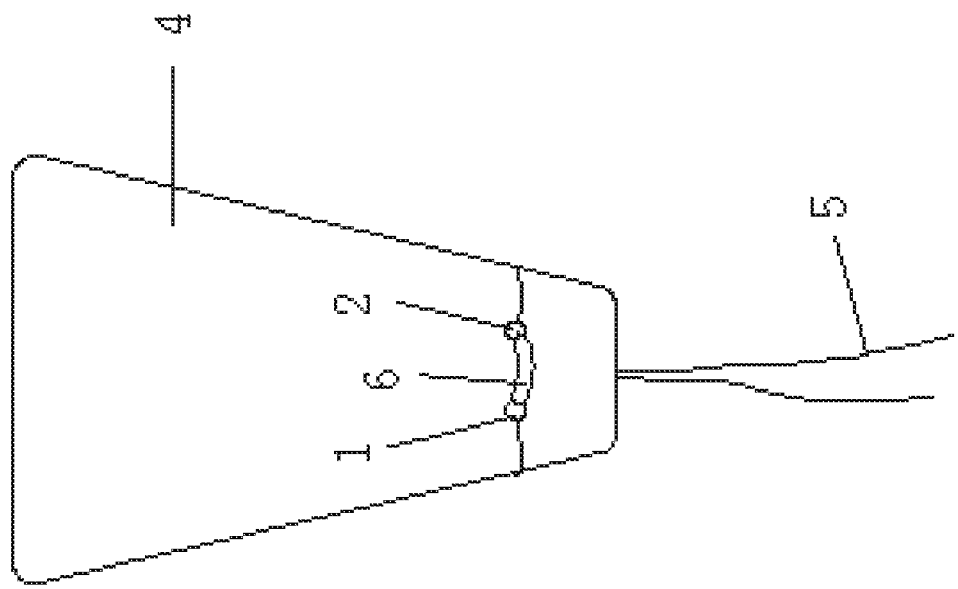
FIG. 29 is a rear view of the Embodiment 5 elastic sheet.

As shown in FIG. 28 and FIG. 29, the difference from the Embodiment 4 lies in the intervening manner of the wire passing though the connecting through-holes. Specifically, two free ends of the wire 5 respectively pass through the first connecting through-hole 1 and the second connecting through-hole 2 from the front of the silicone film 4, respectively bypass the outer contour of lateral sides of the silicone film 4, merge to downwardly pass the space between the first connecting through-hole 1 and the second connecting through-hole 2 and between the wire 5 and the front of silicone film 4, and pass through the third connecting through-hole 3 also from the front of the silicone film 4, then finally are fixed on the rear of the silicone film 4.

A smaller cross section of the elastic sheet of the present embodiment can be obtained by pulling the fixed end of the wire 5, wherein the outer contour of lateral sides of the silicone film 4 are pressed by the wire 5 and the wire 5 between the first connecting through-hole 1 and the second connecting through-hole 2 is stressed by continuously tightening the wire 5 by virtue of the third connecting through-hole 3. The cutting force acting on the silicone film 4 from the wire 5 is dispersed since the wire 5 downwardly passes the space between the first connecting through-hole 1 and the second connecting through-hole 2 and between the wire 5 and the front of silicone film 4. The contact area with the silicone film 4 is increased by the elastic silicone tube 6 sheathed on the wire 5 between the first connecting through-hole 1 and the second connecting through-hole 2. Thus the cutting force acting on the silicone film 4 from the wire 5 is reduced, and the connection force between the wire 5 and the silicone film 4 is increased. The connection force was measured four times in succession. The force values were 6.2 N, 5.2 N, 5.7 N, and 5.1 N, with the average value of 5.6 N. It shows that the force is dispersed, the connection force between the wire 5 and the silicone film 4 is increased, and the cutting damage to the silicone film 4 caused by the wire 5 is reduced. In addition, the pressure on the outer contour of lateral sides of the silicone film 4 caused by tightening the wire 5 can reduce the cross section of the silicone film 4 to facilitate the implantation into the uterus.

Embodiment 6

Figure 30:
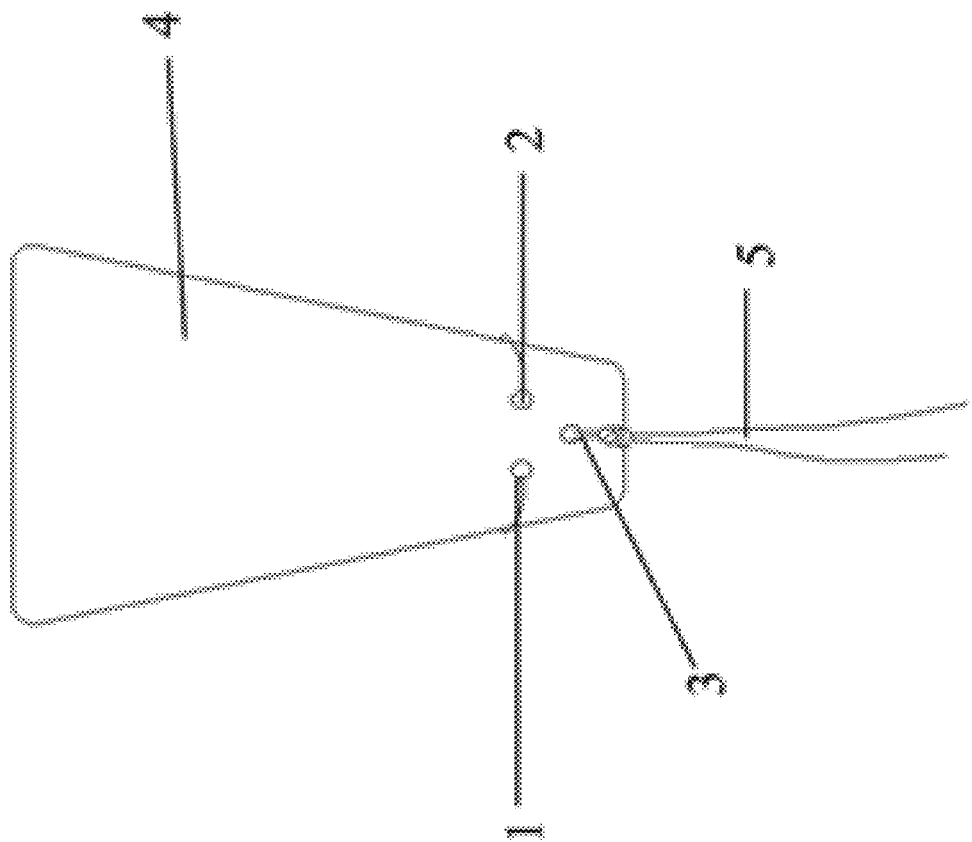
FIG. 30 is a front view of an elastic sheet according to an Embodiment 6.
Figure 31:
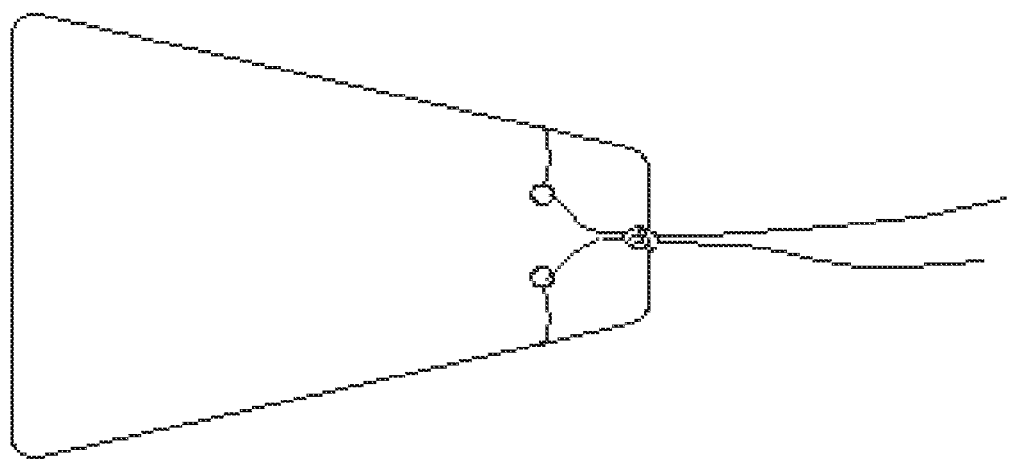
FIG. 31 is a rear view of the Embodiment 6 elastic sheet.

As shown in FIG. 30 and FIG. 31, the difference from the Embodiment 3 lies in the intervening manner of the wire passing though the connecting through-holes. Specifically, the two free ends of the wire 5 respectively pass through the first connecting through-hole 1 and the second connecting through-hole 2 from the front of the silicone film 4, respectively bypass the outer contour of lateral sides of the silicone film 4, and respectively pass through the first connecting through-hole 1 and the second connecting through-hole 2 also from the front of the silicone film 4, then merge to be fixed on the rear of the silicone film 4.

A smaller cross section of the elastic sheet of the present embodiment can be obtained by pulling the fixed end of the wire 5, wherein the outer contour of lateral sides of the silicone film 4 are pressed by the wire 5 and the wire 5 between the first connecting through-hole 1 and the second connecting through-hole 2 is stressed by continuously tightening the wire 5. The contact area with the silicone film 4 is increased by the elastic silicone tube 6 sheathed on the wire 5 between the first connecting through-hole 1 and the second connecting through-hole 2, and thus the cutting force acting on the silicone film 4 from the wire 5 is reduced. The connection force was measured four times in succession. The force values were 3.2 N, 3.8 N, 3.1 N, and 3.7 N, with the average value of 3.5 N. It shows that the connection force between the wire 5 and the silicone film 4 is increased, and the cutting damage to the silicone film 4 caused by the wire 5 is reduced. In addition, the pressure on the outer contour of lateral sides of the silicone film 4 caused by tightening the wire 5 can reduce the cross section of the silicone film 4 to facilitate the implantation into the uterus.

Embodiment 7

The present embodiment provides an elastic sheet, including: a silicone film having tail wire holes, an intervening removal wire passing though the tail wire holes of the silicone film, and a thin tube sheathed on the removal wire.

As shown in FIG. 32 and FIG. 33, there are two tail wire holes, wherein the line connecting the two tail wire holes is parallel to the bottom of the silicone film 1e. The silicone film 1e is an inverted trapezoid shape, with the height of 30 mm, an upper bottom length of 30 mm, and a lower bottom length of 10 mm. A vertical distance between the tail wire hole and the lower bottom of the silicone film 1e is 5 mm. The edge of the tail wire hole is reinforced by a rivet structure 16f (referring to FIG. 34) with a thickness of 1 mm. Each of the tail wire holes is circular, with the diameter of 0.6 mm. The diameter of the tail wire hole is larger than 0.5 mm, which is the diameter of the removal wire 11e. The removal wire 11e is a monofilament single-strand sewing thread. The thin tube 15e sheathed on the removal wire 11e between the two tail wire holes is a silicone tube. The diameter of the thin tube 15e is larger than the removal wire 11e. The thin tube 15e has an inner diameter of 0.5 mm and an outer diameter of 0.8 mm. The length of the thin tube 15c should be greater than the straight length between the centers of the two tail wire holes, and shorter than the longest distance between the edges of the two tail wire holes. The two tail wire holes are passed through from the front of the silicone film 1e by two free ends of the removal wire 11e, which are finally merged to be fixed. The elastic sheet also comprises two implant wire holes (i.e., fixing through-holes). The elastic sheet is fixed to a delivery device 2e (i.e., placing device) by an implant wire 13e passing through the implant wire holes. The edge of the implant wire hole is reinforced by a rivet structure 16f (referring to FIG. 34) with a thickness of 1 mm. Each of the implant wire holes is circular, with the diameter of 0.6 mm. The two implant wire holes are passed through from the front of the silicone film 1e by two free ends of the implant wire 13e, which are finally merged to pass the delivery device 2e.

In the present embodiment, coils of the removal wire 11e and implant wire 13e facing away from the delivery device 2e are sheathed each with a thin tube 15e, in order to reinforce the removal wire 11e and the implant wire 13e, so that the cracking force is transferred to the thin tubes 15e from the removal wire 11e and the implant wire 13e. It should be understood that only the side facing away from the delivery device 2e of the coils is sheathed with thin tubes, namely the side facing the delivery device 2e of the coils is not sheathed to facilitate the stretch during the delivery. As shown in FIG. 34, the rivet structure 16f is a prefabricated tubular with two large ends. Since the rivet structure 16f caught in each of the tail wire holes and the implant wire holes is passed through by the removal wire 11e or the implant wire 13e, the region of the elastic sheet with holes is reinforced in order to prevent the crack.

In the elastic sheet of the present embodiment, the removal wire 11e between the two tail wire holes is stressed by pulling the fixed end of the removal wire 11e and continuously tightening the removal wire 11e. The contact area with the silicone film 1e is increased by the elastic silicone tube 15e sheathed on the removal wire 11e between the two tail wire holes, and thus the cutting force acting on the silicone film 1e from the removal wire 11e is reduced. The connection force was measured four times in succession. The force values were 4.5N, 4.9N, 4.1N, and 4.4N, with the average value of 4.8N. It shows that the two tail wire holes are beneficial to the force dispersion to provide a bigger connection force. The cross section of the silicone film can be reduced by pulling the removal wire 11e. In addition, the damage to the silicone film 1e caused by the removal wire 11e is further reduced by the reinforcing portion at the edge of the tail wire hole.

Comparative Example 1

Figure 36:
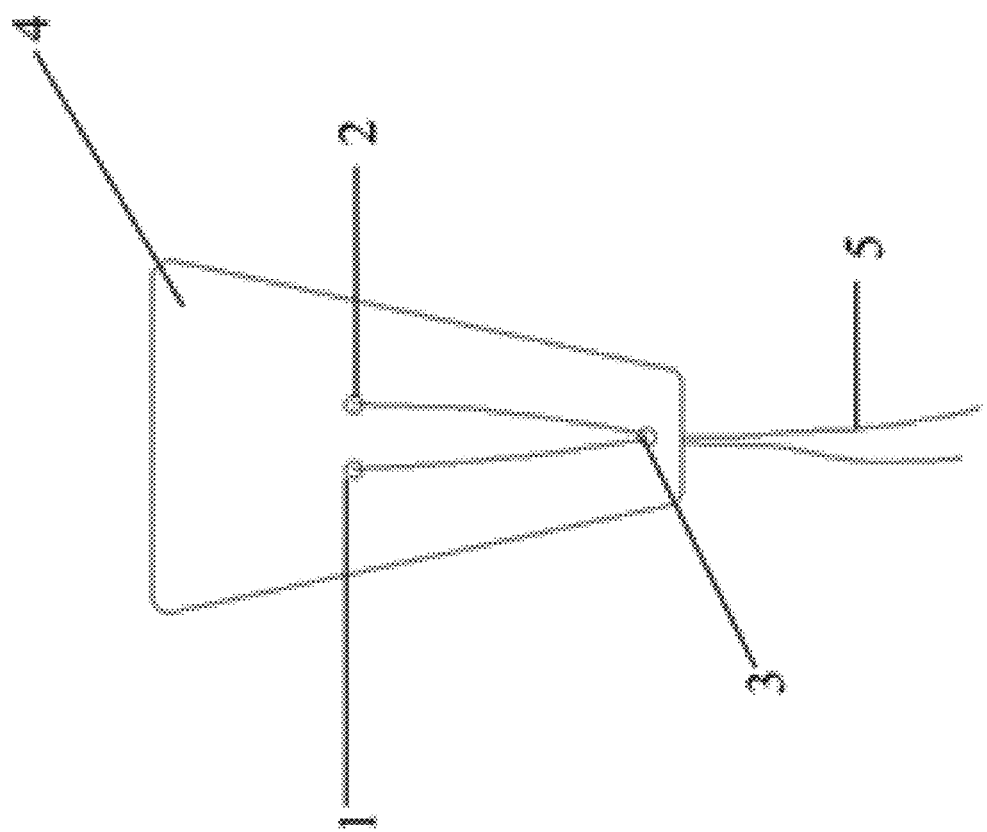
FIG. 36 is a rear view of the Comparative Example 1 elastic sheet.
Figure 35:
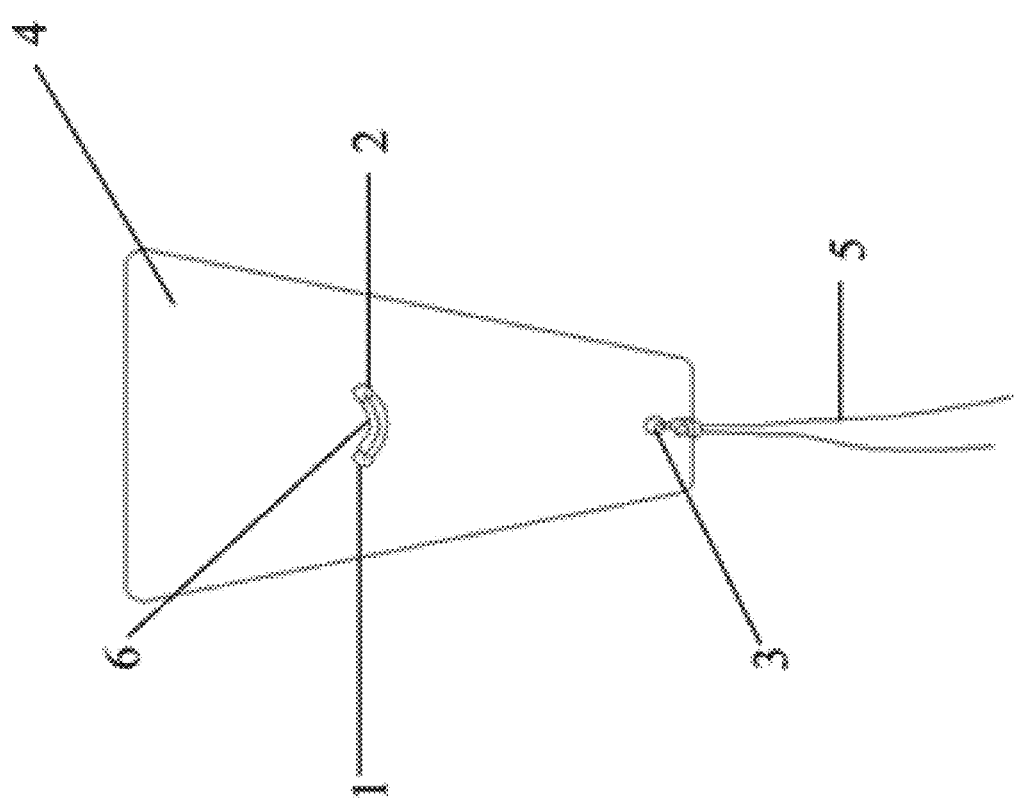
FIG. 35 is a front view of an elastic sheet according to a Comparative Example 1.

As shown in FIG. 35 and FIG. 36, the difference between the present example and Embodiment 1 only lies in that a vertical distance between the first connecting through-hole 1 (or the second connecting through-hole 2) and the lower bottom of the silicone film 4 is 12.5 mm.

In the elastic sheet of this example, due to the long distance between the first connecting through-hole 1 (or the second connecting through-hole 2) and the lower bottom of the silicone film, the elastic sheet may be folded in half by pulling the fixed end of the wire 5. Therefore, the cross section of the elastic sheet would be oversize to provide poor delivery. The wire 5 between the first connecting through-hole 1 and the second connecting through-hole 2 is stressed by continuously tightening the wire 5. The contact area with the silicone film 4 is increased by the elastic silicone tube 6 sheathed on the wire 5 between the first connecting through-hole 1 and the second connecting through-hole 2, and thus the cutting force acting on the silicone film 4 from the wire 5 is reduced and the connection force between the wire 5 and the silicone film 4 is increased. The connection force was measured four times in succession. The force values were 4.3 N, 4.7 N, 5.1 N, and 4.3 N, with the average value of 4.6 N. obviously, the distance between the first connecting through-hole 1 (or the second connecting through-hole 2) and the lower bottom of the silicone film 4 has little effect on the connection force between the wire 5 and the silicone film 4. However, if the distance between the first connecting through-hole 1 and the second connecting through-hole 2 is too small relative to the width of the silicone film 4, the elastic sheet may be folded in half by pulling the fixed end of the wire 5, and thus the cross section of the elastic sheet would be oversize to provide poor delivery.

Comparative Example 2

Figure 37:
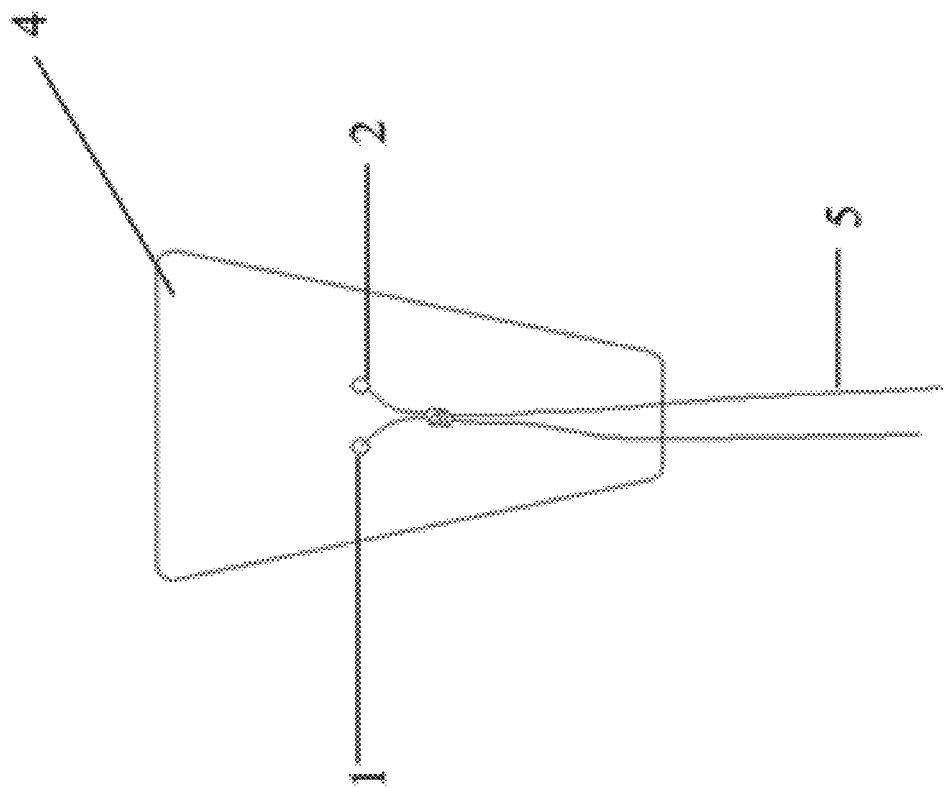
FIG. 37 is a front view of an elastic sheet according to a Comparative Example 2.
Figure 38:
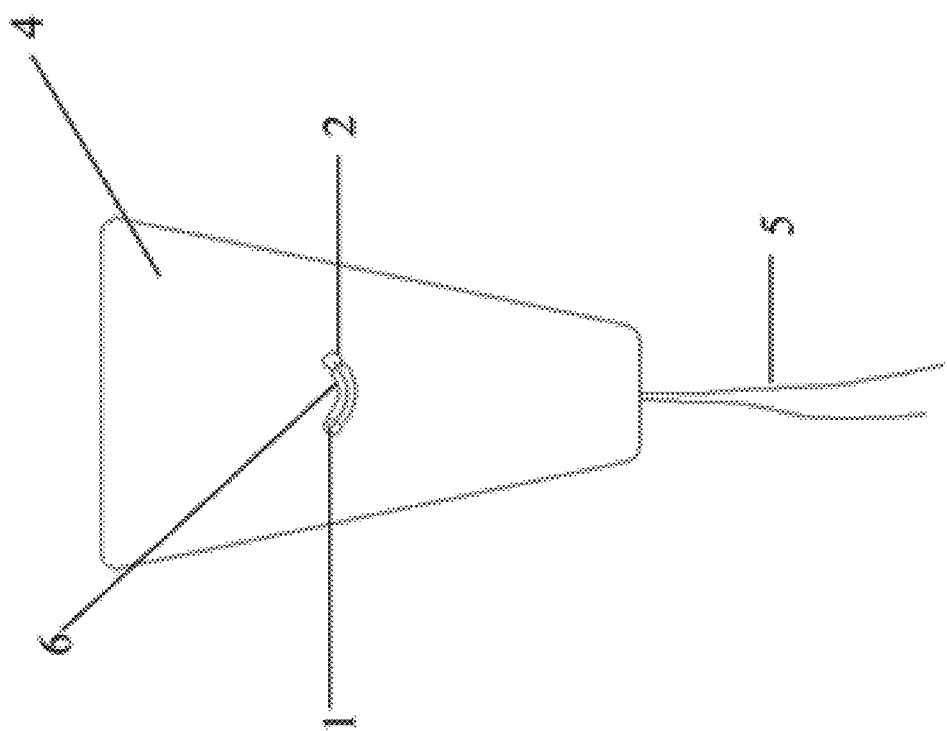
FIG. 38 is a rear view of the Comparative Example 2 elastic sheet.
Figure 40:
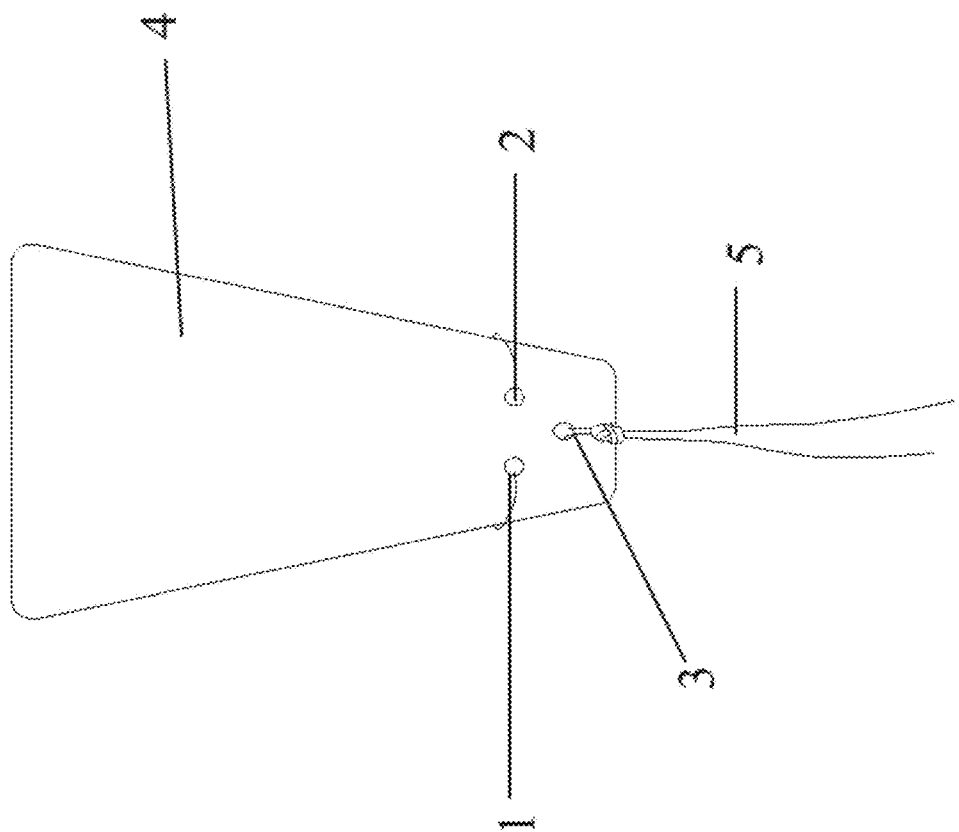
FIG. 40 is a rear view of the Comparative Example 3 elastic sheet.
Figure 39:
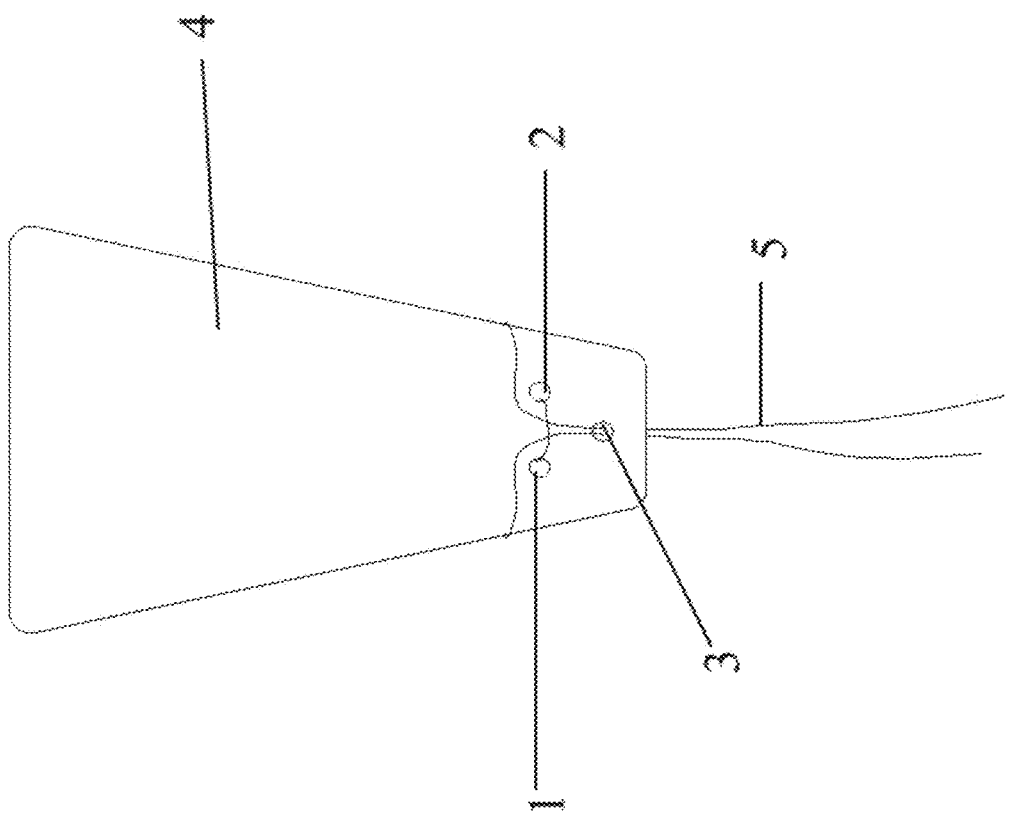
FIG. 39 is a front view of an elastic sheet according to a Comparative Example 3.

As shown in FIG. 37 and FIG. 38, the difference between the present example and Embodiment 3 only lies in that a vertical distance between the first connecting through-hole 1 (or the second connecting through-hole 2) and the lower bottom of the silicone film 4 is 12.5 mm.

In the elastic sheet of this example, due to the long distance between the first connecting through-hole 1 (or the second connecting through-hole 2) and the lower bottom of the silicone film, the elastic sheet may be folded in half by pulling the fixed end of the wire 5. Therefore, the cross section of the elastic sheet would be oversize to provide poor delivery. The contact area with the silicone film 4 is increased by the elastic silicone tube 6 sheathed on the wire 5 between the first connecting through-hole 1 and the second connecting through-hole 2, and thus the cutting force acting on the silicone film 4 from the wire 5 is reduced. The connection force was measured four times in succession. The force values were 3.9 N, 4.5N, 4.1 N, and 4.8 N, with the average value of 4.3 N. obviously, compared with three connecting through-holes of Embodiment 4, the two connecting through-holes is not good for the force dispersion to provide a smaller connection force. The outer contour of lateral sides of the silicone film 4 is not pressed since the outer contour of lateral sides is not bypassed by the wire 5. In addition, the distance between the first connecting through-hole 1 and the second connecting through-hole 2 is too small relative to the width of the silicone film 4 at the same height, which is not good for applying force to the elastic sheet. Thus, the reduction of the cross section of the elastic sheet is limited when the wire 5 is pulled.

Comparative Example 3

The difference between the present example and Embodiment 5 only lies in that there is no thin tube sheathed on the wire between the connecting through-holes.

The connection force was measured four times in succession. The force values were 2.9 N, 3.8 N, 3.2 N, and 3.3N, with the average value of 3.3N. Obviously, the thin tube can effectively reduce the cutting force acting on the silicone film from the wire, in order to avoid the excessive cutting force and the removal difficulty.

1. An elastic sheet comprising: a silicone film having connecting through-holes, an intervening wire passing though the connecting through-holes of the silicone film, and a thin tube sheathed on the wire.
2. The elastic sheet according to the claim 1, wherein there are n connecting through-holes, n≥2, and any two of the connecting through-holes of the silicone film are passed through by two free ends of the wire, which are finally merged to be fixed; preferably, an outer contour of the silicone film is bypassed by the free ends of the wire; preferably, any two of the connecting through-holes of the silicone film are passed through, and an outer contour of the silicone film is bypassed, by the free ends of the wire, which are finally merged into a common connecting through-hole to be fixed.
3. The elastic sheet according to the claim 1, wherein there are three connecting through-holes of a first connecting through-hole, a second connecting through-hole and a third connecting through-hole, wherein the first connecting through-hole and the second connecting through-hole are located above the third connecting through-hole; preferably, the three connecting through-holes are arranged in an inverted triangle; preferably, the inverted triangle is an inverted isosceles triangle, and further preferably an inverted equilateral triangle.
4. The elastic sheet according to the claim 1, wherein the first connecting through-hole and the second connecting through-hole are passed through from the front of the silicone film by two free ends of the wire, which are finally merged into the third connecting through-hole from the rear of the silicone film to be fixed; or, the first connecting through-hole and the second connecting through-hole are passed through from the front of the silicone film, and an outer contour of the silicone film is bypassed, by two free ends of the wire, which are finally merged into the third connecting through-hole from the front of the silicone film to be fixed.
5. The elastic sheet according to the claim 1, wherein the elastic sheet has a thickness of 0.1-4 mm, preferably 0.2-1 mm; preferably, the elastic sheet has a shape of an inverted trapezoid; preferably, the inverted trapezoid has a height of 25-35 mm, an upper bottom of 20-40 mm, and a lower bottom of 5-15 mm.
6. The elastic sheet according to the claim 1, wherein an edge of the connecting through-hole is provided with a reinforcing portion; preferably, the reinforcing portion is a thickened portion; preferably, the thickened portion has a thickness of 0.2-2 mm; preferably, the connecting through-hole has a circular shape; preferably, the connecting through-hole has a diameter of 0.3-1.2 mm, and the diameter of the connecting through-hole is larger than a diameter of the wire.
7. The elastic sheet according to the claim 1, wherein the thin tube is an elastic tube; preferably, the thin tube is a silicone tube; preferably, the thin tube is sheathed on the wire between any two connecting through-holes; preferably, the thin tube has a diameter larger than a diameter of the connecting through-hole; preferably, the wire is formed of any one or at least two of following materials: polypropylene, polyethylene, polyester and polyamide.
8. The elastic sheet according to the claim 1, wherein a minimum vertical distance between the connecting through-hole and a lower bottom of the silicone film is 0.5-4 mm; preferably, a maximum vertical distance between the connecting through-hole and the lower bottom of the silicone film is 1-8 mm.
9. The elastic sheet according to the claim 1, wherein a line connecting any two of the connecting through-holes has a maximum horizontal distance of 2-10 mm on a lower bottom of the silicone film.
10. The elastic sheet according to the claim 1, wherein the silicone film further includes two fixing through-holes, wherein the elastic sheet is fixed to the placing device by a wire passing through the fixing through-holes; preferably, an edge of the fixing through-hole is provided with a reinforcing portion; preferably, the reinforcing portion is a thickened portion; preferably, the thickened portion has a thickness of 0.2-2 mm preferably, the fixing through-hole has a circular shape; preferably, the fixing through-hole has a diameter of 0.3-1.5 mm, and the diameter of the fixing through-hole is larger than a diameter of the wire; preferably, a vertical distance between the fixing through-hole and an upper bottom of the silicone film is 2-8 mm; preferably, the vertical distances between the two fixing through-holes and the upper bottom of the silicone film are the same.

An elastic sheet and a forming method thereof are provided. The elastic sheet comprises a silicone rubber and a drug, wherein the drug is uniformly dispersed inside the silicone rubber, and the drug comprises an estrogen. The elastic sheet provides a preferable therapeutic effect and a longer release period, wherein the drug can be controlled into a steady release by the arrangement of the drug. In addition, the efficient therapeutic effect can be obtained by the drug in a small dose. Further, the drug can be dissolved out and released expediently, since the silicone rubber has high stability and porosity. The method for forming the matrix-type elastic sheet is simple from readily available materials. The easy-to-implement method is convenient for industrial large-scale production.

An elastic sheet and a forming method thereof are provided. The elastic sheet according the present disclosure has a longer release period, wherein the drug can be controlled into a steady release by the arrangement of the drug. In addition, the efficient therapeutic effect can be obtained by the drug in a small dose. The method for forming the matrix-type elastic sheet is simple from readily available materials. The easy-to-implement method provides the matrix-type elastic sheet having a preferable effect in treating the damage to uterus, and is convenient for industrial large-scale production. The elastic sheet is implanted into the uterus, in order to provide a preferable therapeutic effect In addition, the adhesion of the elastic sheet itself is effectively prevented, and a preferable fit with the uterus can be provided.

An object of the present disclosure is to provide an elastic sheet, comprising a silicone rubber and a drug, wherein the drug is uniformly dispersed inside the silicone rubber, and the drug comprises an estrogen.

The elastic sheet in which the drug is uniformly dispersed inside the silicone rubber is called a matrix-type elastic sheet. In some embodiments, the estrogen has a mesh number of 800-10000, e.g. 800, 1000, 2000, 3000, 4000, 5000, 6000, 7000, 8000, 9000, 10000, etc., preferably 3000-8000. In some embodiments, the matrix-type elastic sheet provides an efficient therapeutic effect on a low dose. In addition, the matrix-type elastic sheet has longer release period and preferable sustained release ability, which is suitable for the treatment of uterine cavity damage. In some embodiments, the elastic sheet has estrogen of 2 mg-500 mg. In some embodiments, the estrogen of the elastic sheet has a daily release of 10 μg-4 mg, such as 10 μg, 100 μg, 500 μg, 800 μg, 1 mg, 2 mg, 3 mg, 4 mg, etc.

Usually, when the basal layer of the uterus is damaged, the damaged part does not change with the change of hormones. Therefore, after the adhesion is separated by a known method, since the adhesive portion still cannot produce the functional layer, adhesion is likely to occur again. Surprisingly, according to some embodiments, the estrogen is loaded on the silicone rubber, and thus the endometrial basal layer is continuously activated through drug stimulation, allowing for the endometrial basal layer to re-proliferate the functional layers, thereby restoring the normal endometrial structure and completely preventing adhesions. In particular, in patients with scarred uterus or uterine fibrosis, it is only necessary to surgically separate the fibrotic endometrial basal layer or scar to create a wound surface, so that the regeneration ability of endometrial functional layers can be activated through continuous estrogen stimulation. In some embodiments, the estrogen has a daily release of 10 μg-4 mg to a threshold of action for at least one week to provide a sustained release system with a controlled release rate and a release period. In some embodiments, the estrogen has a daily release of estrogen of 20 μg-1 mg, and the estrogenic amount per elastic sheet is 10 mg-200 mg.

In some embodiments, the matrix-type elastic sheet comprises a silicone rubber and a drug located inside the silicone rubber. Since the silicone rubber has high stability and porosity, the drug can be dissolved out expediently. Since the silicone rubber has good penetration and permeability, the drug release can be controlled expediently. The drug dissolution rate can be controlled by the mesh number of the drug, and thus the drug efficacy and drug release period can be controlled.

In some embodiments, the estrogen comprises any one or at least two of 17β estradiol, estrone, estriol, and estradiol derivatives. In some embodiments, the estrogen comprises any one or at least two of estradiol benzoate, estradiol valerate, ethinyl estradiol, ethinyl estradiol, conjugated estrogens, diethylstilbestrol, nylestriol and promestriene.

In some embodiments, the drug further comprises a drug for improving endometrial blood flow. In some embodiments, drug for improving endometrial blood flow has a mesh number of 500-5000, such as 500, 1000, 1500, 2000, 2500, 3000, 3500, 4000, 4500, 5000, etc., preferably 500-2000. In some embodiments, a weight ratio of the estrogen to the drug for improving endometrial blood flow is 1:(0.1-1), such as 1:0.1, 1:0.2, 1:0.3, 1:0.4, 1:0.5, 1:0.6, 1:0.7, 1:0.8, 1:0.9, 1:1, etc., preferably 1:(0.3-0.6).

In some embodiments, the drug comprises estrogen with a mesh number of 800-10000 and drug for improving endometrial blood flow with a mesh number of 500-5000. The estrogen with a larger mesh number can be easily dissolved out from the pores of silicone rubber, and thus the drug release rate is higher and the drug release amount is more. The drug for improving endometrial blood flow with a smaller mesh number cannot be easily dissolved out from the pores of silicone rubber, and thus the drug release rate is lower and the drug release amount is less. The invention can effectively control the sustained release of the drug by controlling the mesh number of estrogen and drug for improving endometrial blood flow. Thus, the preferable therapeutic effect and longer drug release period can be obtained. The therapeutic effect would be affected by the control failure of the drug release of two drugs and the synergy after the dissolution such as if the mesh number is not within the scope of the present disclosure.

In some embodiments, the estrogen and drug for improving endometrial blood flow work together, in particular with proper mesh number and weight ratio, which can increase capillary blood supply, promote local targeted release of the drug, and promote endometrial hyperplasia. The efficient therapeutic effect can be obtained in a low dose without side effects such as hormonal disturbance caused by a large dose. The therapeutic effect would be affected by the control failure of the synergy of the two drugs such as if the weight ratio is not within the scope of the present disclosure.

In some embodiments, the drug for improving endometrial blood flow comprises any one or at least two of aspirin, sildenafil citrate, pentoxifylline (PTX) and vitamin E, L-arginine, and low molecular weight heparin. In some embodiments, the daily release amount of the drug for improving endometrial blood flow is 200 μg-20 mg, such as 200 μg, 500 μg, 1 mg, 5 mg, 10 mg, 15 mg, 20 mg, etc. In some embodiments, the drug further comprises a colony stimulating factor. In some embodiments, the colony stimulating factor includes granulocyte colony stimulating factor (G-CSF), and/or granulocyte-macrophage colony stimulating factor (GM-CSF). In some embodiments, a weight ratio of the colony stimulating factor to the estrogen is (0.05-0.5):1, such as 0.05:1, 0.1:1, 0.15:1, 0.2:1, 0.25:1, 0.3:1, 0.35:1, 0.4:1, 0.45:1, 0.5:1, etc. In some embodiments, the colony stimulating factor is for modulating local immunity of the uterine cavity, which is capable of promoting endometrial basal cell proliferation.

In some embodiments, the elastic sheet has a thickness of 0.1-4 mm, such as 0.1 mm, 0.5 mm, 0.8 mm, 1 mm, 1.2 mm, 1.5 mm, 1.8 mm, 2 mm, 2.2 mm, 2.5 mm, 2.8 mm, 3 mm, 3.2 mm, 3.5 mm, 3.8 mm, 4 mm, etc., preferably 0.2-1 mm. In some embodiments, the elastic sheet has a shape of an inverted trapezoid. In some embodiments, the elastic sheet has a shape with a big upper end and a small lower end. After the implantation, the upper end corresponds to the uterine fundus, and the lower end corresponds to the uterine cervix at an intrauterine opening, which is beneficial for the fit to the uterus. In some embodiments, the inverted trapezoid has a height of 25-35 mm (such as 25 mm, 26 mm, 27 mm, 28 mm, 29 mm, 30 mm, 31 mm, 32 mm, 33 mm, 34 mm, 35 mm, etc.), an upper bottom of 20-40 mm (such as 20 mm, 22 mm, 25 mm, 27 mm, 30 mm, 32 mm, 35 mm, 37 mm, 40 mm, etc.), and a lower bottom of 5-15 mm (such as 5 mm, 6 mm, 7 mm, 8 mm, 9 mm, 10 mm, 11 mm, 12 mm, 13 mm, 14 mm, 15 mm, etc.).

In some embodiments, the silicone rubber has a crosslink density of 3000-8000 g/mol, such as 3000 g/mol, 3500 g/mol, 4000 g/mol, 4500 g/mol, 5000 g/mol, 5500 g/mol, 6000 g/mol, 6500 g/mol, 7000 g/mol, 7500 g/mol, 8000 g/mol, etc., preferably 4000-6000 g/mol. The crosslink density refers to the number of effective crosslink contained in a unit volume of a thermosetting elastomer, which is used to be the characteristic of the cross-linking degree of the elastomer. In some embodiments, it is found that the drug with a higher crosslink density is released in a smaller amount under the same condition. However, the crosslink density affects the properties of the silicone rubber, such as an elastic modulus, a breaking strength, and an elongation at break, etc., so that the crosslink density has the best elasticity and sustained release effect in the above range. In some embodiments, the elastic sheet has an elastic modulus of 0.5-3 MPa, such as 0.9 MPa, 1.0 MPa, 1.1 MPa, 1.3 MPa, 1.5 MPa, 1.8 MPa, 2.5 MPa, etc., preferably 1-2 MPa.

It should be understood that the elastic sheet has an inverted trapezoidal shape. After the implantation, the trapezoidal long bottom is located at the uterine fundus, and the trapezoidal short bottom is located at the cervix opening. In the stretched state after the implantation, the shape of the elastic sheet is adapted to the physiological shape and size of the uterus to isolate the anterior and posterior walls of the uterus as completely as possible, so that the contact between the anterior and posterior walls of the uterus is minimized. During the implantation, a conventional device is enough for the doctor to put the elastic sheet into the uterus. It should be understood that the elastic sheet can be contracted into a cylindrical shape by the doctor if necessary. The contracted elastic sheet can be delivery through the cervical canal into the uterus by a tube, and then be stretched after the implantation. In particular, the silicone rubber with an elastic modulus within above range is beneficial to the contraction to provide the curled state of the elastic sheet during the delivery. In addition, the elastic characteristic of the silicone rubber provides the automatic stretch in the uterine cavity to the maximum extent, and the re-curl or re-contraction caused by the movement of the uterine cavity is prevented, the isolation of the anterior wall from the posterior wall of the uterus is maximized.

In some embodiments, the silicone rubber comprises any one or at least two of heat vulcanized silicone rubber (HTV), room temperature vulcanized silicone rubber (RTV), low temperature vulcanized silicone rubber (LTV), DOW-CORNING Silastic-382 medical silicone rubber, and DOW-CORNING Q7 medical silicone rubber series and implantable MDX series. In some embodiments, the silicone rubber comprises any one or at least two of a self-modifying HTV, RTV solid silicone rubber, LTV solid silicone rubber, RTV liquid silicone rubber or LTV liquid silicone rubber. In some embodiments, the self-modifying HTV comprises 40-80 wt % of HTV silicone rubber, 10-50 wt % of silica, 5-15 wt % of hydroxy silicone oil, 5-30 wt % of medical barium sulfate, 0.1-2 wt % of iron oxide red, and 0.5-1.5 wt % of benzoyl peroxide. In some embodiments, the RTV solid silicone rubber or LTV solid silicone rubber comprises 40-80 wt % of silicone rubber, 20-60 wt % of silica, 5-15 wt % of hydroxy silicone oil, 5-30 wt % of medical barium sulfate, 0.1-2 wt % of iron oxide red. In some embodiments, the RTV liquid silicone rubber or LTV liquid silicone rubber comprises 40-80 wt % of silicone rubber, 20-60 wt % of silica, 5-20 wt % of vinyl silicone oil, 0.02-1 wt % of ethynyl cyclohexanol.

In some embodiments, the weight ratio of the silicone rubber to the drug is (50%-99%):(50%-1%), such as 50%: 50%, 55%:45%, 60%:40%, 65%:35%, 70%:30%, 75%: 25%, 80%:20%, 85%:15%, 90%:10%, 95%:5%, 99%:1%, etc., preferably (60%-90%):(40%-10%). In some embodiments, the elastic sheet has a sustained release period of 3-90 days, such as 3 days, 10 days, 20 days, 30 days, 40 days, 50 days, 60 days, 70 days, 80 days, 90 days, etc. In some embodiments, the drug is uniformly dispersed inside a plurality of zones of the silicone rubber. In some embodiments, the drug can be uniformly dispersed inside all zones of the silicone rubber, and can be uniformly dispersed in some zones of the silicone rubber. Thus, the elastic sheet can be used for the treatment of the overall uterine cavity trauma, and can also be used for the treatment of the local uterine cavity trauma. Namely, the uterine cavity can be treated locally according to the local trauma.

Another object of the present disclosure is to provide a method forming the elastic sheet. The method comprises of crosslinking and solidifying a silicone rubber with a drug to form the elastic sheet. The method forming the elastic sheet is simple from readily available materials. The easy-to-implement method is convenient for industrial large-scale application. In some embodiments, the crosslinking is realized by vulcanization. In some embodiments, the silicone rubber is a self-modifying HTV silicone rubber, and the method forming the elastic sheet comprises: mixing, vulcanizing, crosslinking and solidifying the self-modifying HTV silicone rubber with a drug according to a weight ratio into a mixed sheet from the silicone rubber and drug to form the elastic sheet.

In some embodiments, the silicone rubber is a RTV solid silicone rubber and/or LTV solid silicone rubber, and the method forming the elastic sheet comprises: the RTV solid silicone rubber and/or LTV solid silicone rubber are divided into two groups, wherein the group A and the drug is kneaded with 0.1-1% platinum catalyst in a rubber mixer to form a uniform, the group B and the drug is kneaded with 1-10% active hydrogen cross-linking agent in a rubber mixer to form a uniform and cut into small pieces, and then the products obtained from the two groups are mixed and extruded, and then vulcanized and crosslinked, and solidified into a mixed sheet from the silicone rubber and drug to form the elastic sheet.

In some embodiments, the silicone rubber is a RTV liquid silicone rubber and/or LTV liquid silicone rubber, and the method forming the elastic sheet comprises: the RTV liquid silicone rubber and/or LTV liquid silicone rubber are divided into two groups, wherein the group A and the drug is kneaded with 0.1-2% hydrogen-containing silicone oil in a rubber mixer to form a uniform, the group B and the drug is kneaded with 0.05-2% platinum catalyst in a rubber mixer to form a uniform, and then the products obtained from the two groups are mixed and extruded, and then vulcanized and crosslinked, and solidified into a mixed sheet from the silicone rubber and drug to form the elastic sheet.

Yet another object of the present disclosure is to provide a composite elastic sheet, wherein the composite elastic sheet comprises a plurality of the layers of the elastic sheet. In some embodiments, the plurality of the layers can be understood as two layers or at least two layers, wherein the drug dispersed in each layer may be the same or different. Yet another object of the present disclosure is to provide an application method for the elastic sheet in a drug sustained release system. In some embodiments, the drug sustained release system refers to a device made of a drug and a carrier or a medium, which enables the drug to be released in a designed dose and in a controlled manner, in order to treat a certain disease or improve the immunity of the body.

The elastic sheet of the present disclosure has the following beneficial effects compared with the prior art. The elastic sheet of the present disclosure provides a preferable therapeutic effect and a longer release period, wherein the drug can be controlled into a steady release by the arrangement of the drug, in particular based on the mesh number and weight of the drug. In addition, the efficient therapeutic effect can be obtained by the drug in a small dose. Further, the drug can be dissolved out and released expediently, since the silicone rubber has high stability and porosity, in order to provide the preferable therapeutic effect to the damage of uterus. The method for forming the matrix-type elastic sheet is simple from readily available materials. The easy-to-implement method is convenient for industrial large-scale production.

Embodiment 1

The present embodiment provides an elastic sheet comprising a silicone rubber and a drug uniformly dispersed inside the silicone rubber, wherein the silicone rubber has a crosslink density of 5000 g/mol. The drug is 17β estradiol, with a mesh number of 5000, wherein the content of 17β estradiol per elastic sheet is 25 mg. The thickness of the elastic sheet is 0.5 mm. The shape of the elastic sheet is an inverted trapezoid, with a height of 30 mm, an upper bottom of 30 mm and a lower bottom of 10 mm.

The embodiment further provides a method for forming an elastic sheet, which comprises following steps.

g of 17β estradiol (average particle size 5,000 mesh), 30 g of HTV medical silicone rubber (molecular weight 20-100 million), 10 g of silica, 5 g of hydroxy silicone oil, 6 g of medical barium sulfate, 0.5 g of iron oxide red, and 2 g of benzoyl peroxide were kneaded to a uniform on a rubber mixer, and hot pressed on a flat vulcanizer to form a sheet having a thickness of 0.5 mm, and then cut into a desired shape to obtain a matrix-type elastic sheet.

The content of the drug per elastic sheet was calculated according to the volume of the elastic sheet, wherein the content of 17β estradiol per elastic sheet=(the mass of 17β estradiol×the volume of a matrix-type elastic sheet)/the total volume of the matrix-type elastic sheets. The sample was dissolved in PBS solution at 37° C. on a drug dissolution tester, and the dissolution content was measured by HPLC. The result showed that within 30 days, the maximum amount of drug dissolution was 400 μg/d in the first 3 days, and then the drug dissolution was gradually stabilized, wherein the average drug release in 30 days was 178 μg/d.

The New Zealand rabbits were tested. Before the implantation, 6 trauma models were obtained by surgical curettage and divided into two groups A and B. The group A was given the same dose per weight of estradiol by oral, and the group B was implanted the suitable size of the elastic sheet of the present embodiment without oral estradiol. After 30 days, different degrees of adhesions happened in the uteri of the test animals in group A, but there was no adhesion happened in the uteri of the test animals in group B, wherein the endometrial in group B grew well with mild and visible surgical trace.

The physical properties of the elastic sheet in the present embodiment were tested according to the test method of the standard GB/T528.1-2009. The result comprised a tensile strength of 8.5 MPa, a breaking strength of 37 kN/m, an elongation at break of 1138%, and an elastic modulus of 1.62 MPa.

Embodiment 2

The present embodiment provides an elastic sheet comprising a silicone rubber and a drug uniformly dispersed inside the silicone rubber, wherein the silicone rubber has a crosslink density of 4000 g/mol. The drug is 17β estradiol, with a mesh number of 2000, wherein the content of 17β estradiol per elastic sheet is 50 mg. The thickness of the elastic sheet is 0.1 mm. The shape of the elastic sheet is an inverted trapezoid, with a height of 25 mm, an upper bottom of 20 mm and a lower bottom of 5 mm.

The embodiment further provides a method for forming an elastic sheet, which comprises following steps.

3 g of 17β estradiol (average particle size 2,000 mesh) and 30 g of RTV-2 medical silicone rubber were kneaded to a uniform on a rubber mixer, and hot pressed on a flat vulcanizer to form a sheet having a thickness of 0.2 mm, and then cut into a desired shape to obtain a matrix-type elastic sheet.

The content of 17β estradiol per elastic sheet was calculated to 50 mg according to the volume of the elastic sheet. The sample was dissolved in PBS solution at 37° C. on a drug dissolution tester, and the dissolution content was measured by HPLC. The result showed that within 90 days, the maximum amount of drug dissolution was 530 μg/d in the first 3 days, and then the drug dissolution was gradually stabilized, wherein the average drug release in 90 days was 215 μg/d.

The New Zealand rabbits were tested. Before the implantation, 6 trauma models were obtained by surgical curettage and divided into two groups A and B. The group A was given the same dose per weight of estradiol by oral, and the group B was implanted the suitable size of the elastic sheet of the present embodiment without oral estradiol. After 30 days, different degrees of adhesions happened in the uteri of the test animals in group A, but there was no adhesion happened in the uteri of the test animals in group B.

Figure 41:
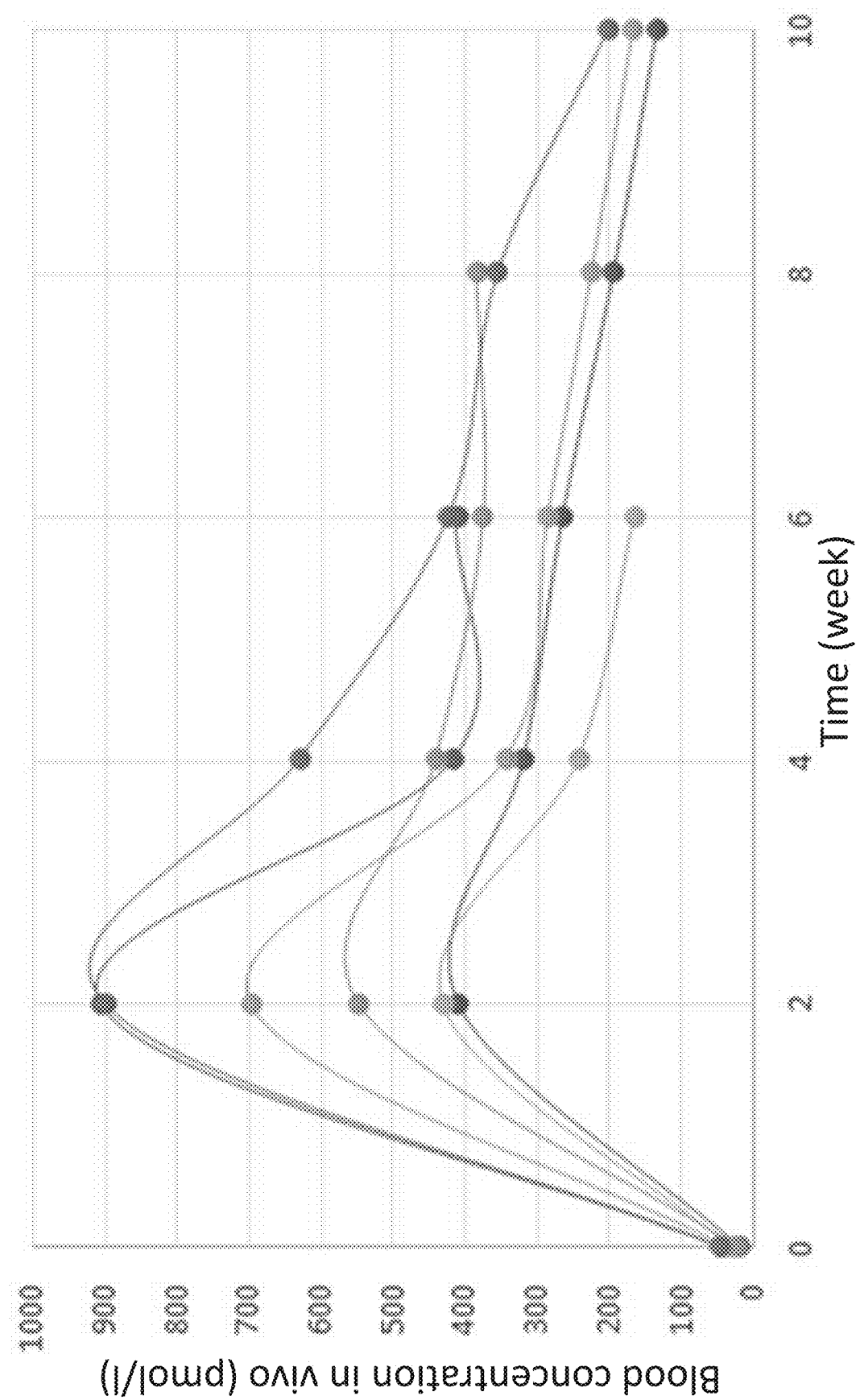
FIG. 41 shows the trend of the blood concentration change in vivo of 6. New Zealand rabbits within 10 weeks after the implantation of the elastic sheet of Embodiment 2.

FIG. 41 shows the trend of the blood concentration change in vivo of 6. New Zealand rabbits within 10 weeks after the implantation. It can be seen from the FIG. that the blood concentration in the early stage of the implantation is higher, and the later stage is slowed down. The blood concentrations of subjects were measured per 2 weeks, and the trend in vivo matched the release in vitro despite the few of data points.

Figure 42:
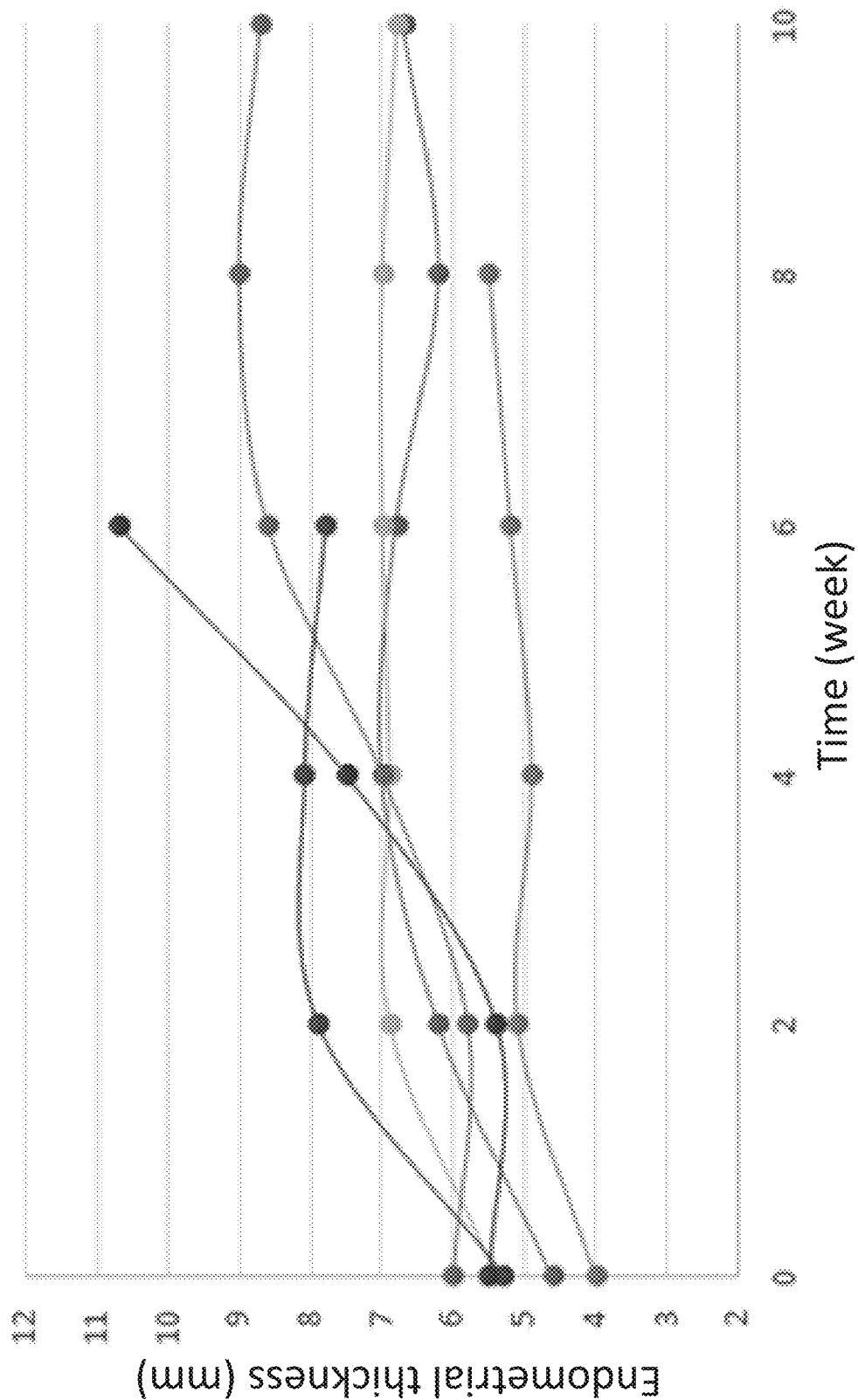
FIG. 42 shows the endometrial thickness change of 6. New Zealand rabbits within 10 weeks after the implantation of the elastic sheet of Embodiment 2.

FIG. 42 shows the endometrial thickness change of 6. New Zealand rabbits within 10 weeks after the implantation, and the relevant data are shown in the following table:

TABLE 5

| | Week | | | | | | |
|---|---|---|---|---|---|---|---|
| | 0 | 2 | 4 | 6 | 8 | 10 | Improvement |
| A1 | 4.6 | 6.2 | 7 | 6.8 | 6.2 | 6.7 | Active |
| A2 | 5.3 | 7.9 | 8.1 | 7.8 | | | Active |
| A3 | 5.5 | 5.4 | 7.5 | 10.7 | | | Active |
| A4 | 4 | 5.1 | 4.9 | 5.2 | 5.5 | | Inactive |
| A5 | 5.4 | 6.9 | 6.9 | 7 | 7 | 6.8 | Active |
| A6 | 6 | 5.8 | 7 | 8.6 | 9 | 8.7 | Active |

Obviously, the endometrium of the subject was gradually increased, namely the elastic sheet had a significant effect. In fact, the matrix-type elastic sheet is mainly used for patients with moderate adhesion.

The physical properties of the elastic sheet in the present embodiment were tested according to the test method of the standard GB/T528.1-2009. The result comprised a tensile strength of 8.3 MPa, a breaking strength of 35 kN/m, an elongation at break of 1076%, and an elastic modulus of 1.4 MPa.

Embodiment 3

The present embodiment provides an elastic sheet comprising a silicone rubber and a drug uniformly dispersed inside the silicone rubber, wherein the silicone rubber has a crosslink density of 6000 g/mol. The drug is 17β estradiol, with a mesh number of 2000, wherein the content of 17β estradiol per elastic sheet is 100 mg. The thickness of the elastic sheet is 0.2 mm. The shape of the elastic sheet is an inverted trapezoid, with a height of 35 mm, an upper bottom of 40 mm and a lower bottom of 15 mm.

The embodiment further provides a method for forming an elastic sheet, which comprises following steps.

5 g of 17β estradiol (average particle size 2,000 mesh), 30 g of HTV medical silicone rubber (molecular weight 20-100 million), 10 g of silica, 5 g of hydroxy silicone oil, 6 g of medical barium sulfate, 0.5 g of iron oxide red, and 2 g of benzoyl peroxide were kneaded to a uniform on a rubber mixer, and hot pressed on a flat vulcanizer to form a sheet having a thickness of 0.2 mm, and then cut into a desired shape to obtain a matrix-type elastic sheet.

The content of 17β estradiol per elastic sheet was calculated to 100 mg according to the volume of the elastic sheet. The sample was dissolved in PBS solution at 37° C. on a drug dissolution tester, and the dissolution content was measured by HPLC. The result showed that within 60 days, the maximum amount of drug dissolution was 760 μg/d in the first 3 days, and then the drug dissolution was gradually stabilized, wherein the average drug release in 60 days was 274 μg/d.

The New Zealand rabbits were tested. Before the implantation, 6 trauma models were obtained by surgical curettage and divided into two groups A and B. The group A was given the same dose per weight of estradiol by oral, and the group B was implanted the suitable size of the elastic sheet of the present embodiment without oral estradiol. After 60 days, different degrees of adhesions happened in the uteri of the test animals in group A, but there was no adhesion happened in the uteri of the test animals in group B, wherein the endometrium in group B grew well.

The physical properties of the elastic sheet in the present embodiment were tested according to the test method of the standard GB/T528.1-2009. The result comprised a tensile strength of 8.8 MPa, a breaking strength of 39 kN/m, an elongation at break of 1146%, and an elastic modulus of 1.76 MPa.

Figure 43:
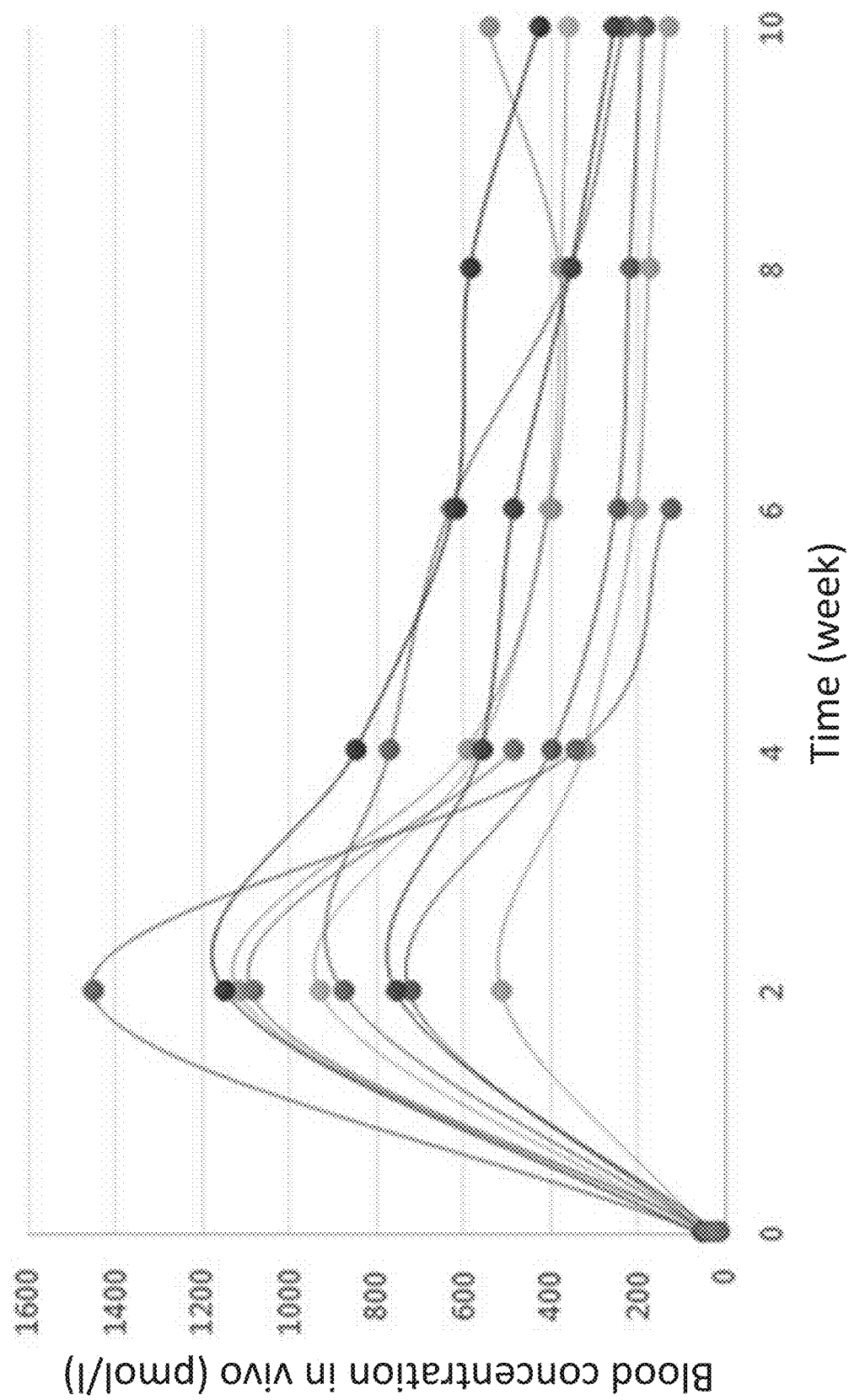
FIG. 43 shows the trend of the blood concentration change in vivo of 9. New Zealand rabbits within 10 weeks after the implantation of the elastic sheet of Embodiment 3.

FIG. 43 shows the trend of the blood concentration change in vivo of 9. New Zealand rabbits within 10 weeks after the implantation. It can be seen from the FIG. that the blood concentration in the early stage of the implantation is higher, and the later stage is slowed down. The blood concentrations of subjects were measured per 2 weeks, and the trend in vivo matched the release in vitro despite the few of data points.

Figure 44:
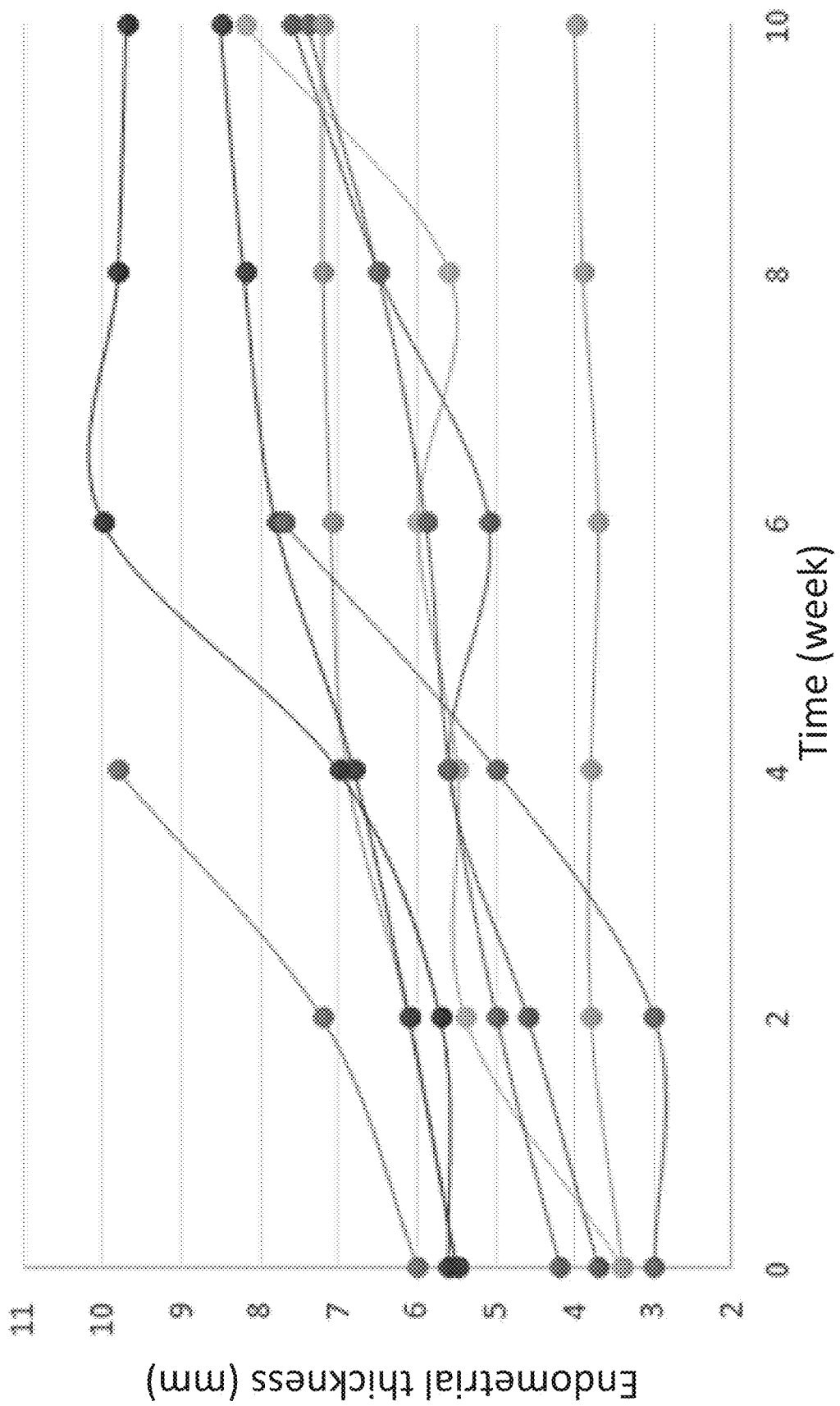
FIG. 44 shows the endometrial thickness change of 9. New Zealand rabbits within 10 weeks after the implantation of the elastic sheet of Embodiment 3.

FIG. 44 shows the endometrial thickness change of 9. New Zealand rabbits within 10 weeks after the implantation, and the relevant data are shown in the following table:

TABLE 6

| | \multicolumn{6}{c}{Week} | |
| | 0 | 2 | 4 | 6 | 8 | 10 | Improvement |
| --- | --- | --- | --- | --- | --- | --- | --- |
| B1 | 3.7 | 4.6 | 5.6 | 5.1 | 6.5 | 7.6 | Active |
| B2 | 3.4 | 5.4 | 5.5 | 6 | 5.6 | 8.2 | Active |
| B3 | 4.2 | 5 | 5.6 | 5.9 | 6.5 | 7.4 | Active |
| B4 | 5.5 | 6.1 | 6.9 | 7.1 | 7.2 | 7.2 | Active |
| B5 | 3 | 3 | 5 | 7.7 | | | Active |
| B6 | 3.4 | 3.8 | 3.8 | 3.7 | 3.9 | 4 | Inactive |
| B7 | 6 | 7.2 | 9.8 | | | | Active |
| B8 | 5.5 | 6.1 | 6.8 | 7.8 | 8.2 | 8.5 | Active |
| B9 | 5.6 | 5.7 | 7 | 10 | 9.8 | 9.7 | Active |

Obviously, the endometrium of the subject was gradually increased, namely the elastic sheet had a significant effect. In fact, the matrix-type elastic sheet is mainly used for patients with moderate adhesion.

Figure 45:
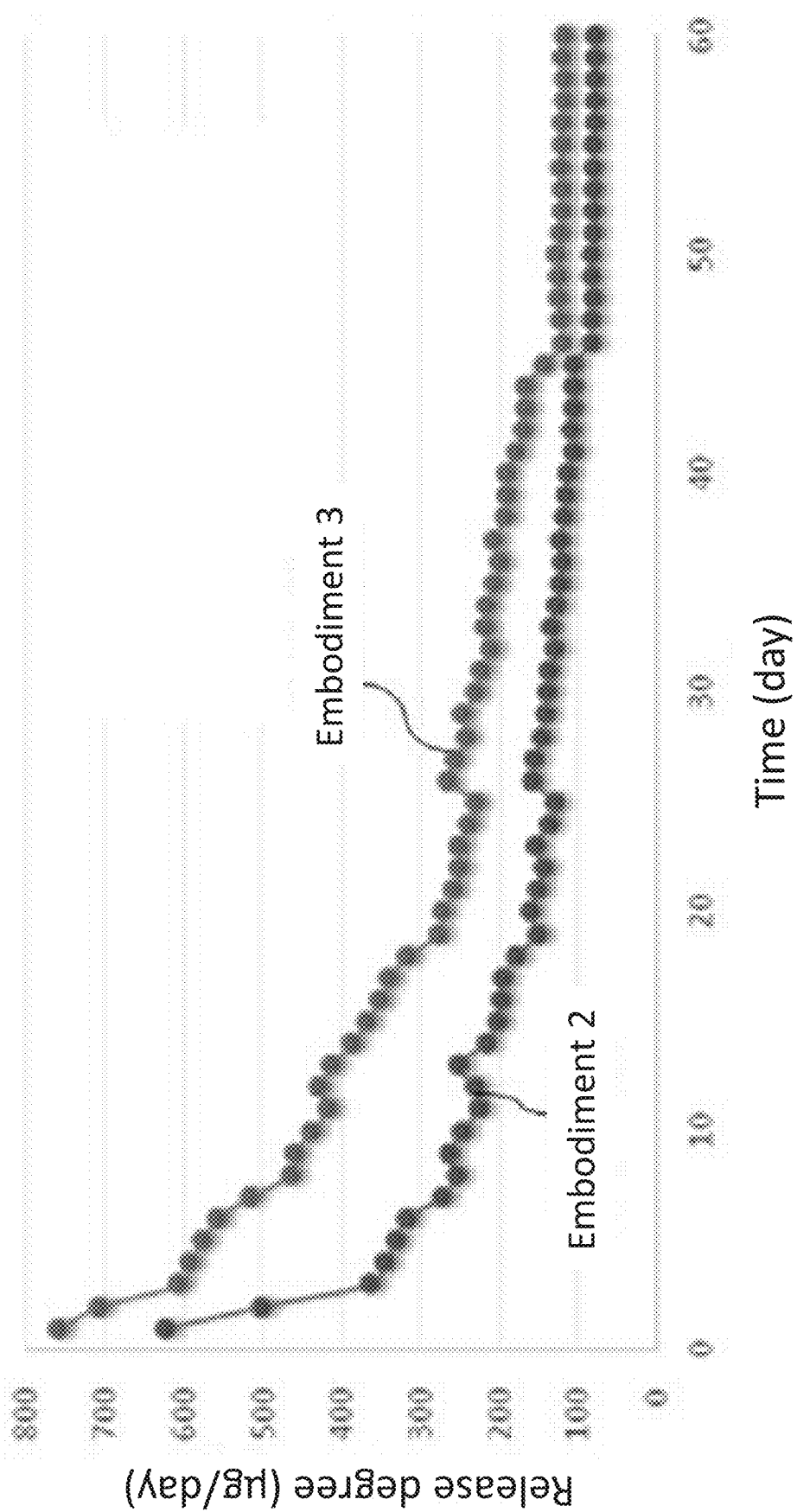
FIG. 45 shows the comparison of 60-day release curve in vitro of the elastic sheets of Embodiment 2 and the Embodiment 3.

FIG. 45 shows the comparison of 60-day release curve of the elastic sheets according to Embodiment 2 and Embodiment 3. It can be seen from the FIG. that the daily release amount of the elastic sheet containing 100 mg of estradiol is larger than that of the elastic sheet containing 50 mg of estradiol, but they are not in a multiple relationship. That is to say, the daily release can be increased by the total drug amount loaded on the elastic sheet, which is the key to activate the endometrium. Moreover, not all drugs can be released, and only 20% of the total drug amount is released in 60 days, which is limited by the fact that the silicone rubber is a non-degradable material, and most drugs cannot be completely released. Therefore, the controlled release of the matrix-type elastic sheet is slower with a longer release period of 60-90 days, and even longer.

Figure 46:
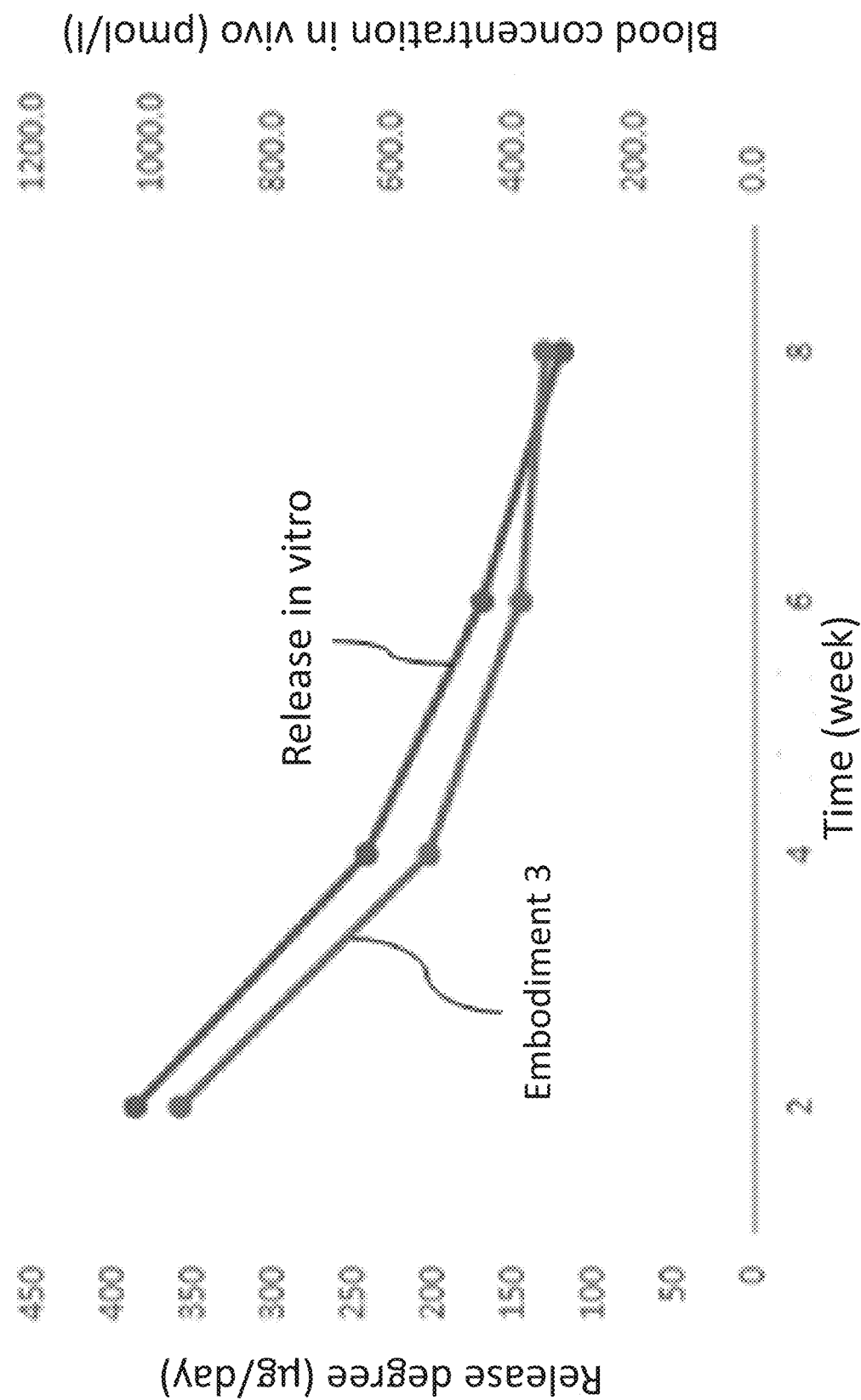
FIG. 46 shows the comparison of the release amount in vitro and the blood concentration in vivo after the implantation of the elastic sheet of Embodiment 3.

FIG. 46 shows the comparison of the release amount in vitro and the blood concentration in vivo after the implantation. It can be seen from the FIG. that the blood concentration in vivo is consistent with the release in vitro trend, thus the treatment in vivo can be adjusted by the release in vitro.

The following table gives a comparison of a relationship between the oral dose and the blood concentration in vivo and another relationship between the released drug of the elastic sheet and the blood concentration in vivo:

TABLE 7

| Embodiment 3 | Release amount in vitro (μg/d) | 387 | 243 | 171 | 121 |
| --- | --- | --- | --- | --- | --- |
| | Blood concentration (pmol/l) | 957.7 | 544.8 | 392.1 | 349.6 |
| Oral | Oral dose (μg/d) | 4000 | 3000 | 2000 | 1000 |
| | Blood concentration (pmol/l) | 989.3 | 498.5 | 255.8 | 111.2 |

Obviously, the blood concentration is 989.3 pmol/l by oral administration of 4000 micrograms. The blood concentration can also be 957.7 pmol/l by the elastic sheet of the present embodiment with daily release of 387 micrograms. It shows that 90% of oral drugs have been intercepted by the liver. The elastic sheet can achieve the same effect with less than 1/10 intake drug, in order to prevent the side effects. And drugs can be released steadily in a long-term without drug peaks and troughs, which are very common for the oral daily administration.

Embodiment 4

The present embodiment provides an elastic sheet comprising a silicone rubber and a drug uniformly dispersed inside the silicone rubber, wherein the silicone rubber has a crosslink density of 3000 g/mol. The drug is 17β estradiol, with a mesh number of 2000, wherein the content of 17β estradiol per elastic sheet is 75 mg. The thickness of the elastic sheet is 0.2 mm. The shape of the elastic sheet is an inverted trapezoid, with a height of 35 mm, an upper bottom of 40 mm and a lower bottom of 15 mm.

The embodiment further provides a method for forming an elastic sheet, which comprises following steps.

Under the condition that the sum of the components was 100 wt %, 60 g of silicone rubber, 25 g of silica, 7 g of hydroxy silicone oil, 7.5 g of medical barium sulfate, and 0.5 g of iron oxide red were kneaded on a rubber mixer and divided into two groups according to the weight, each group being 50 g.

12.5 g of estradiol (average particle size 2,000 mesh) and 50 g of the group A, 0.1-1% of platinum catalyst were kneaded to a uniform on a rubber mixer. 12.5 g of estradiol (average particle size 2,000 mesh) and 50 g of the group B, and 1-10% active hydrogen cross-linking agent were kneaded to a uniform on a rubber mixer. Then the products obtained from the two groups were mixed and extruded, then vulcanized and crosslinked, and solidified into a mixed sheet having a thickness of 0.2 mm from the silicone rubber and drug to form a matrix-type elastic sheet.

The content of 17β estradiol per elastic sheet was calculated to 75 mg according to the volume of the elastic sheet. The sample was dissolved in PBS solution at 37° C. on a drug dissolution tester, and the dissolution content was measured by HPLC. The result showed that within 60 days, the maximum amount of drug dissolution was 652 μg/d in the first 3 days, and then the drug dissolution was gradually stabilized, wherein the average drug release in 60 days was 243 μg/d.

The New Zealand rabbits were tested. Before the implantation, 6 trauma models were obtained by surgical curettage and divided into two groups A and B. The group A was given the same dose per weight of estradiol by oral, and the group B was implanted the suitable size of the elastic sheet of the present embodiment without oral estradiol. After 60 days, different degrees of adhesions happened in the uteri of the test animals in group A, but there was no adhesion happened in the uteri of the test animals in group B, wherein the endometrial in group B grew well.

The physical properties of the elastic sheet in the present embodiment were tested according to the test method of the standard GB/T528.1-2009. The result comprised a tensile strength of 7.9 MPa, a breaking strength of 31 kN/m, an elongation at break of 997%, and an elastic modulus of 1.08 MPa.

Embodiment 5

The present embodiment provides an elastic sheet comprising a silicone rubber and a drug uniformly dispersed inside the silicone rubber, wherein the drug comprises an estrogen and a drug for improving endometrial blood flow, and wherein the silicone rubber has a crosslink density of 5000 g/mol. The estrogen is an estradiol, with a mesh number of 2000. The drug for improving endometrial blood flow is an aspirin, with a mesh number of 500. The content of estradiol per elastic sheet is 10 mg. The content of aspirin per elastic sheet is 2 mg. The thickness of the elastic sheet is 0.5 mm. The shape of the elastic sheet is an inverted trapezoid, with a height of 30 mm, an upper bottom of 30 mm and a lower bottom of 10 mm.

The embodiment further provides a method for forming an elastic sheet, which comprises following steps.

Under the condition that the sum of the components was 100 wt %, 70 g of silicone rubber, 15 g of silica, 8 g of hydroxy silicone oil, 6 g of medical barium sulfate, and 1 g of iron oxide red were kneaded on a rubber mixer and divided into two groups according to the weight, each group being 50 g.

2.5 g of estradiol (average particle size 2,000 mesh) and 50 g of the group A, 0.1-1% of platinum catalyst were kneaded to a uniform on a rubber mixer. 0.5 g of aspirin (average particle size 500 mesh) and 50 g of the group B, and 1-10% active hydrogen cross-linking agent were kneaded to a uniform on a rubber mixer. Then the products obtained from the two groups were mixed and extruded, then vulcanized and crosslinked, and solidified into a mixed sheet having a thickness of 0.5 mm from the silicone rubber and drug to form a matrix-type elastic sheet.

The content of estradiol per elastic sheet was calculated to 10 mg, and the content of aspirin per elastic sheet was calculated to 2 mg according to the volume of the elastic sheet. The sample was dissolved in PBS solution at 37° C. on a drug dissolution tester, and the dissolution content was measured by HPLC. The result showed that within 60 days, the maximum amount of estradiol dissolution was 157 μg/d and the maximum amount of aspirin dissolution was 62 μg/d in the first 3 days, and then the drug dissolutions were gradually stabilized, wherein the average released estradiol was 94 μg/d and the average released aspirin was 42 μg/d in 60 days.

The New Zealand rabbits were tested. Before the implantation, 6 trauma models were obtained by surgical curettage and divided into two groups A and B. The group A was given the same dose per weight of estradiol by oral, and the group B was implanted the suitable size of the elastic sheet of the present embodiment without oral estradiol. After 60 days, different degrees of adhesions happened in the uteri of the test animals in group A, but there was no adhesion happened in the uteri of the test animals in group B, wherein the endometrial in group B grew well.

Figure 47:
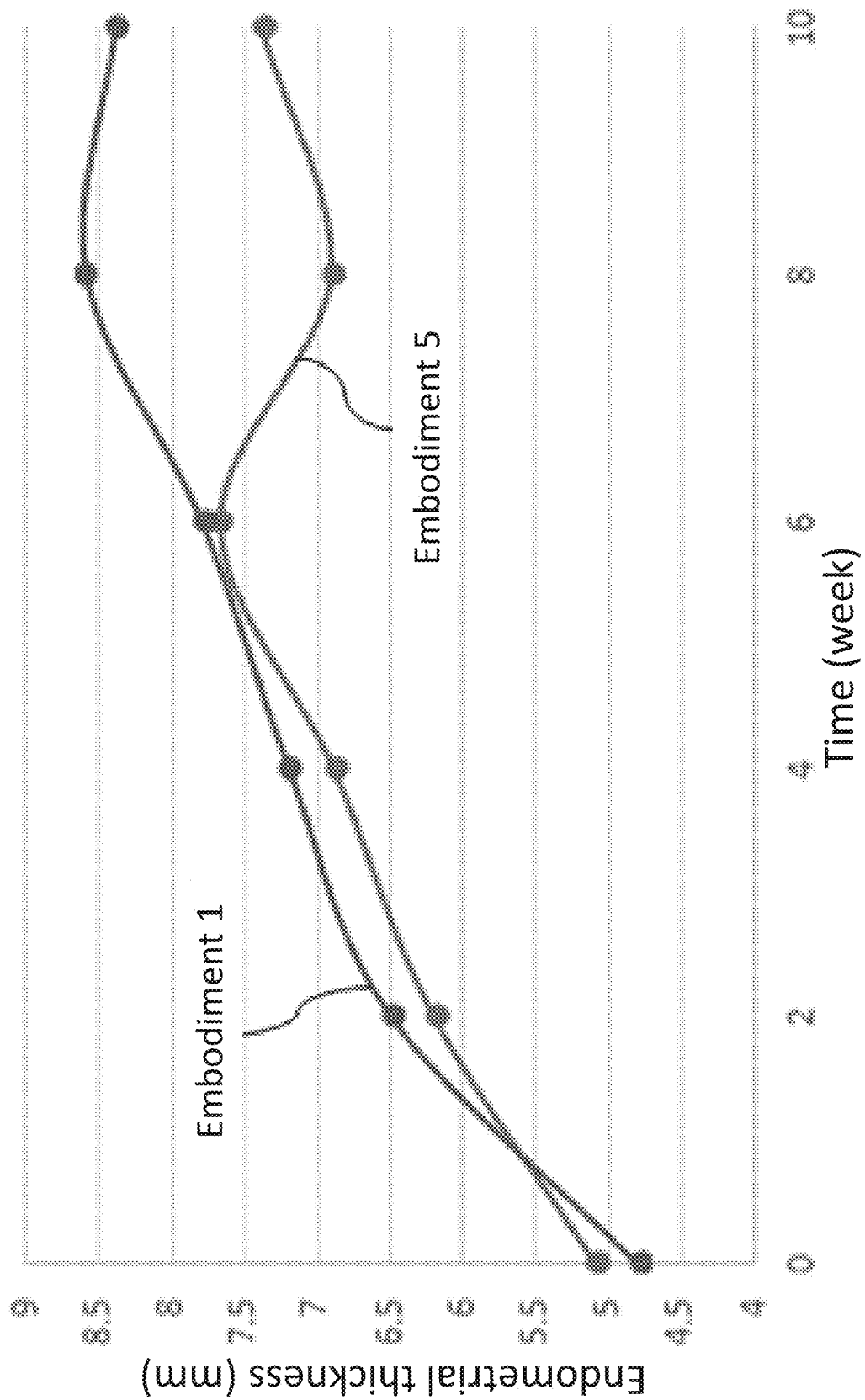
FIG. 47 shows the endometrial thickness change after the implantation of the elastic sheets of Embodiment 1 and Embodiment 5.

FIG. 47 shows the endometrial thickness change after the implantation of the elastic sheet with estradiol alone according to Embodiment 1 and after the implantation of the elastic sheet with estradiol in the combination with aspirin according to Embodiment 5. The average endometrial growth of the subjects was listed in following table:

TABLE 8

| | Drug amount (mg) | | Average release degree in the first 60 days (μg/d) | | Average endometrial thickness within 10 weeks | | | | | |
|---|---|---|---|---|---|---|---|---|---|---|
| | Estradiol | Aspirin | Estradiol | Aspirin | 0 | 2 | 4 | 6 | 8 | 10 |
| Embodiment 1 | 50 | 0 | 166 | 0 | 5.1 | 6.2 | 6.9 | 7.7 | 6.9 | 7.4 |
| Embodiment 5 | 50 | 10 | 152 | 42 | 4.8 | 6.5 | 7.2 | 7.8 | 8.6 | 8.4 |

Obviously, at the same dose, by the drug (aspirin) for increasing the blood circulation, the endometrial growth was accelerated, and the endometrium was thicker. That is to say, the estradiol and the drug (aspirin) for increasing the blood circulation provide a synergistic effect.

Embodiment 6

The present embodiment provides an elastic sheet comprising a silicone rubber and a drug uniformly dispersed inside the silicone rubber, wherein the drug comprises an estrogen and a drug for improving endometrial blood flow, and wherein the silicone rubber has a crosslink density of 8000 g/mol. The estrogen is an estradiol, with a mesh number of 2000. The drug for improving endometrial blood flow is an aspirin, with a mesh number of 500. The content of estradiol per elastic sheet is 50 mg. The content of aspirin per elastic sheet is 20 mg. The thickness of the elastic sheet is 0.5 mm. The shape of the elastic sheet is an inverted trapezoid, with a height of 30 mm, an upper bottom of 20 mm and a lower bottom of 5 mm.

The embodiment further provides a method for forming an elastic sheet, which comprises following steps.

Under the condition that the sum of the components was 100 wt %, 70 g of silicone rubber, 15 g of silica, 8 g of hydroxy silicone oil, 6 g of medical barium sulfate, and 1 g of iron oxide red were kneaded on a rubber mixer and divided into two groups according to the weight, each group being 50 g.

12.5 g of estradiol (average particle size 2,000 mesh) and 50 g of the group A, 0.1-1% of platinum catalyst were kneaded to a uniform on a rubber mixer. 5 g of aspirin (average particle size 500 mesh) and 50 g of the group B, and 1-10% active hydrogen cross-linking agent were kneaded to a uniform on a rubber mixer. Then the products obtained from the two groups were mixed and extruded, then vulcanized and crosslinked, and solidified into a mixed sheet having a thickness of 0.5 mm from the silicone rubber and drug to form a matrix-type elastic sheet.

The content of estradiol per elastic sheet was calculated to 50 mg, and the content of aspirin per elastic sheet was calculated to 20 mg according to the volume of the elastic sheet. The sample was dissolved in PBS solution at 37° C. on a drug dissolution tester, and the dissolution content was measured by HPLC. The result showed that within 90 days, the maximum amount of estradiol dissolution was 543 µg/d and the maximum amount of aspirin dissolution was 489 µg/d in the first 3 days, and then the drug dissolutions were gradually stabilized, wherein the average released estradiol was 213 µg/d and the average released aspirin was 142 µg/d in 90 days.

The New Zealand rabbits were tested. Before the implantation, 6 trauma models were obtained by surgical curettage and divided into two groups A and B. The group A was given the same dose per weight of estradiol by oral, and the group B was implanted the suitable size of the elastic sheet of the present embodiment without oral estradiol. After 90 days, different degrees of adhesions happened in the uteri of the test animals in group A, but there was no adhesion happened in the uteri of the test animals in group B, wherein the endometrial in group B grew well.

The physical properties of the elastic sheet in the present embodiment were tested according to the test method of the standard GB/T528.1-2009. The result comprised a tensile strength of 8.9 MPa, a breaking strength of 41 kN/m, an elongation at break of 1156%, and an elastic modulus of 1.87 MPa.

Embodiment 7

The present embodiment provides an elastic sheet comprising a silicone rubber and a drug uniformly dispersed inside the silicone rubber, wherein the drug comprises an estrogen and a drug for improving endometrial blood flow, and wherein the silicone rubber has a crosslink density of 5000 g/mol. The estrogen is an estradiol, with a mesh number of 2000. The drug for improving endometrial blood flow comprises a pentoxifylline (PTX) with a mesh number of 500 and a vitamin E with a mesh number of 800. The content of estradiol per elastic sheet is 10 mg. The content of PTX per elastic sheet is 5 mg. The content of vitamin E per elastic sheet is 5 mg. The thickness of the elastic sheet is 0.5 mm. The shape of the elastic sheet is an inverted trapezoid, with a height of 30 mm, an upper bottom of 20 mm and a lower bottom of 5 mm.

The embodiment further provides a method for forming an elastic sheet, which comprises following steps.

Under the condition that the sum of the components was 100 wt %, 50 g of silicone rubber, 35 g of silica, 7 g of hydroxy silicone oil, 7 g of medical barium sulfate, and 1 g of iron oxide red were kneaded on a rubber mixer and divided into two groups according to the weight, each group being 50 g.

2.5 g of estradiol (average particle size 2,000 mesh) and 50 g of the group A, 0.1-1% of platinum catalyst were kneaded to a uniform on a rubber mixer. 1.5 g of PTX (average particle size 500 mesh), 1.5 g of vitamin E (average particle size 800 mesh) and 50 g of the group B, and 1-10% active hydrogen cross-linking agent were kneaded to a uniform on a rubber mixer. Then the products obtained from the two groups were mixed and extruded, then vulcanized and crosslinked, and solidified into a mixed sheet having a thickness of 0.5 mm from the silicone rubber and drug to form a matrix-type elastic sheet.

The content of estradiol per elastic sheet was calculated to 10 mg, the content of PTX per elastic sheet was calculated to 5 mg, and the content of vitamin E per elastic sheet was calculated to 5 mg according to the volume of the elastic sheet. The sample was dissolved in PBS solution at 37° C. on a drug dissolution tester, and the dissolution content was measured by HPLC. The result showed that within 90 days, the maximum amount of estradiol dissolution was 145 µg/d, the maximum amount of PTX dissolution was 89 µg/d and the maximum amount of vitamin E dissolution was 99 µg/d in the first 3 days, and then the drug dissolutions were gradually stabilized, wherein the average released estradiol was 89 µg/d, the average released PTX was 63 µg/d and the average released vitamin E was 69 µg/d in 90 days.

The New Zealand rabbits were tested. Before the implantation, 6 trauma models were obtained by surgical curettage and divided into two groups A and B. The group A was given the same dose per weight of estradiol by oral, and the group B was implanted the suitable size of the elastic sheet of the present embodiment without oral estradiol. After 90 days, different degrees of adhesions happened in the uteri of the test animals in group A, but there was no adhesion happened in the uteri of the test animals in group B, wherein the endometrial in group B grew well.

Comparative Example 1

The difference from the Embodiment 1 only lies in the mesh number of 500 of the estrogen.

The content of the drug per elastic sheet was calculated according to the volume of the elastic sheet. The sample was dissolved in PBS solution at 37° C. on a drug dissolution tester, and the dissolution content was measured by HPLC. The result showed that within 30 days, the maximum amount of drug dissolution was 155 µg/d in the first 3 days, and then the drug dissolution was gradually stabilized, wherein the average drug release in 30 days was 53 µg/d.

The New Zealand rabbits were tested. Before the implantation, 6 trauma models were obtained by surgical curettage and divided into two groups A and B. The group A was given the same dose per weight of estradiol by oral, and the group B was implanted the suitable size of the elastic sheet of the present embodiment without oral estradiol. After 30 days, different degrees of adhesions happened in the uteri of the test animals in groups A and B.

Figure 48:
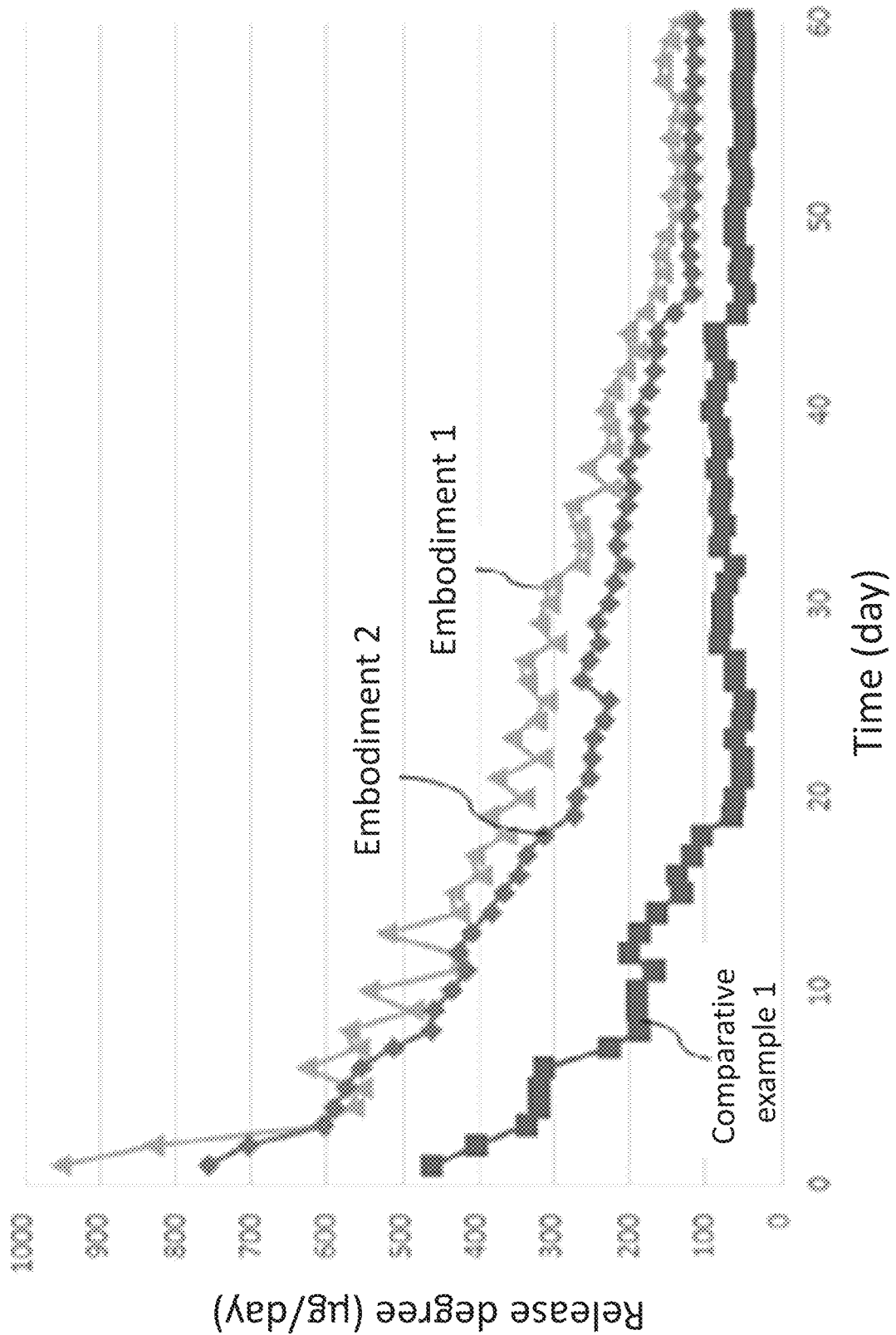
FIG. 48 shows the release degree in vitro of the elastic sheets containing estradiol with different mesh numbers of Embodiments 1-2 and Comparative example 1.

FIG. 48 shows the trend and comparison of release degree in vitro of the elastic sheet containing estradiol with different diameters according to Embodiments 1-2 and Comparative example 1. It can be seen that the drug micronization can be used to control the drug release. The drug with a bigger mesh number and a bigger specific surface area is less likely to be released, and vice versa. For the matrix-type elastic sheet, the mesh number of the drug should be above 500.

Comparative Example 2

The difference from the Embodiment 1 only lies in the mesh number of 10000 of the estrogen.

The content of the drug per elastic sheet was calculated according to the volume of the elastic sheet. The sample was dissolved in PBS solution at 37° C. on a drug dissolution tester, and the dissolution content was measured by HPLC. The result showed that within 30 days, the maximum amount of drug dissolution was 1625 μg/d in the first 3 days, and then the drug dissolution was gradually stabilized, wherein the average drug release in 30 days was 507 μg/d.

Following table 9 shows the endometrial thicknesses of 3 New Zealand rabbits within 10 weeks after the implantation, and the relevant data are shown in the following table:

TABLE 9

| | Week | | | | | | |
|---|---|---|---|---|---|---|---|
| | 0 | 2 | 4 | 6 | 8 | 10 | Improvement | Others |
| C1 | 3.9 | 4.0 | 4.3 | 4.5 | 4.7 | 4.9 | Active | vesicles |
| C2 | 4.6 | 4.2 | 4.3 | 4.8 | 5.0 | 5.1 | Active | |
| C3 | 4.5 | 4.3 | 4.7 | 4.9 | 5.2 | 5.3 | Active | vesicles |

Following table 10 gives a comparison of a relationship between the oral dose and the blood concentration in vivo and another relationship between the released drug of the elastic sheet and the blood concentration in vivo:

TABLE 10

| Comparative example 2 | Release amount in vitro (μg/d) | 527 | 503 | 492 |
|---|---|---|---|---|
| | Blood concentration (pmol/l) | 1521.1 | 1473.6 | 1467.8 |
| Oral | Oral dose (μg/d) | 4000 | 4000 | 4000 |
| | Blood concentration (pmol/l) | 989.3 | 998.5 | 955.8 |

Obviously, since the estrogen is with too big mesh number and too small diameter, the release is excessive and provides too high blood concentration. Thus, different degrees of vesicles appeared in spite of the effective drug treatment.

Comparative Example 3

The difference from the Embodiment 2 only lies in the crosslink density of 2000 g/mol of the silicone rubber.

The sample was dissolved in PBS solution at 37° C. on a drug dissolution tester, and the dissolution content was measured by HPLC. The result showed that within 90 days, the maximum amount of drug dissolution was 928 μg/d in the first 3 days, and then the drug dissolution was gradually stabilized, wherein the average drug release in 30 days was 406 μg/d.

The physical properties of the elastic sheet in the present embodiment were tested according to the test method of the standard GB/T528.1-2009. The result comprised a tensile strength of 4.7 MPa, a breaking strength of 23 kN/m, an elongation at break of 872%, and an elastic modulus of 0.4 MPa.

The New Zealand rabbits were tested. Before the implantation, 6 trauma models were obtained by surgical curettage. During the implantation, the elastic sheet was curled and then flattened with an auxiliary device. After 30 days, different degrees of adhesions happened in the uteri of the test animals of the present Comparative example.

Comparative Example 4

The difference from the Embodiment 2 only lies in the crosslink density of 10000 g/mol of the silicone rubber.

The sample was dissolved in PBS solution at 37° C. on a drug dissolution tester, and the dissolution content was measured by HPLC. The result showed that within 90 days, the maximum amount of drug dissolution was 321 μg/d in the first 3 days, and then the drug dissolution was gradually stabilized, wherein the average drug release in 30 days was 131 μg/d.

The physical properties of the elastic sheet in the present embodiment were tested according to the test method of the standard GB/T528.1-2009. The result comprised a tensile strength of 8.9 MPa, a breaking strength of 41 kN/m, an elongation at break of 977%, and an elastic modulus of 1.89 MPa.

The New Zealand rabbits were tested. Before the implantation, 6 trauma models were obtained by surgical curettage. During the implantation, the elastic sheet was not easily curled into the uterus, and finally curled with an auxiliary device. After 30 days, different degrees of adhesions happened in the uteri of the test animals of the present Comparative example.

Comparative Example 5

The difference from the Embodiment 5 only lies in the weight ratio of 1:1 of estradiol to aspirin.

The content of estradiol per elastic sheet was calculated to 6 mg, and the content of aspirin per elastic sheet was calculated to 6 mg according to the volume of the elastic sheet. The sample was dissolved in PBS solution at 37° C. on a drug dissolution tester, and the dissolution content was measured by HPLC. The result showed that within 60 days, the maximum amount of estradiol dissolution was 106 μg/d and the maximum amount of aspirin dissolution was 108 μg/d in the first 3 days, and then the drug dissolutions were gradually stabilized, wherein the average released estradiol was 68 μg/d and the average released aspirin was 66 μg/d in 60 days.

The New Zealand rabbits were tested. Before the implantation, 6 trauma models were obtained by surgical curettage. After 60 days, different degrees of endometrium growth and adhesions happened in the uteri of the test animals of the present Comparative example.

Following table 11 shows the endometrial thickness change after the implantation of the elastic sheet according to Embodiment 5 and after the implantation of the elastic sheet according to Comparative example 5. The average endometrial growth of the subjects was listed in following table:

TABLE 11

| | Average endometrial thickness within 10 weeks | | | | | |
|---|---|---|---|---|---|---|
| | 0 | 2 | 4 | 6 | 8 | 10 |
| Embodiment 5 | 4.8 | 5.1 | 5.3 | 5.1 | 5.2 | 5.4 |
| Comparative example 5 | 4.3 | 4.5 | 4.5 | 4.6 | 4.5 | 4.7 |

Since the estradiol content in the drug is too low, the therapeutic effect of the estradiol is not good. Thus, the synergistic effect plays a positive role in the case of proper drug weight ratio.

1. An elastic sheet, comprising: a silicone rubber; and a drug; wherein the drug is uniformly dispersed inside the silicone rubber, and the drug comprises an estrogen.
2. The elastic sheet according to the claim 1, wherein the estrogen has a mesh number of 800-10000; preferably, the mesh number of the estrogen is 3000-8000; preferably, the estrogen has a daily release of 10 μg-4 mg.
3. The elastic sheet according to the claim 1, wherein the estrogen comprises any one or at least two of 17β estradiol, estrone, estriol, and estradiol derivatives; preferably, the estrogen comprises any one or at least two of estradiol benzoate, estradiol valerate, ethinyl estradiol, ethinyl estradiol, conjugated estrogens, diethylstilbestrol, nylestriol and promestriene.
4. The elastic sheet according to the claim 1, wherein the drug further comprises a drug for improving endometrial blood flow; preferably, the drug for improving endometrial blood flow has a mesh number of 500-5000, preferably 500-2000; preferably, a weight ratio of the estrogen to the drug for improving endometrial blood flow is 1:(0.1-1), preferably 1:(0.3-0.6); preferably, the drug for improving endometrial blood flow has a daily release of 200 μg-20 mg.
5. The elastic sheet according to the claim 1, wherein the drug further comprises a colony stimulating factor; preferably, the colony stimulating factor includes granulocyte colony stimulating factor (G-CSF), and/or granulocyte-macrophage colony stimulating factor (GM-CSF); preferably, a weight ratio of the colony stimulating factor to the estrogen is (0.05-0.5):1.
6. The elastic sheet according to the claim 1, wherein the elastic sheet has a thickness of 0.1-4 mm, preferably 0.2-1 mm; preferably, the elastic sheet has a shape of an inverted trapezoid; preferably, the inverted trapezoid has a height of 25-35 mm, an upper bottom of 20-40 mm, and a lower bottom of 5-15 mm.
7. The elastic sheet according to the claim 1, wherein the silicone rubber has a crosslink density of 3000-8000 g/mol, preferably 4000-6000 g/mol; preferably, the elastic sheet has an elastic modulus of 0.5-3 MPa, preferably 1-2 MPa; preferably, the silicone rubber comprises any one or at least two of heat vulcanized silicone rubber (HTV), room temperature vulcanized silicone rubber (RTV), low temperature vulcanized silicone rubber (LTV), DOWCORNING Silastic-382 medical silicone rubber, and DOWCORNING Q7 medical silicone rubber series and implantable MDX series; preferably, the silicone rubber comprises any one or at least two of a self-modifying HTV, RTV solid silicone rubber, LTV solid silicone rubber, RTV liquid silicone rubber or LTV liquid silicone rubber; preferably, the weight ratio of the silicone rubber to the drug is (50%-99%):(50%-1%), preferably (60%-90%): (40%-10%); preferably, the drug is uniformly dispersed inside a plurality of zones of the silicone rubber; preferably, the sustained release period of the elastic sheet is 3-90 days.
8. A method for forming the elastic sheet according to claim 1, comprising: crosslinking and solidifying a silicone rubber with a drug to form the elastic sheet, preferably, the crosslinking is realized by vulcanization.
9. A composite elastic sheet, wherein the composite elastic sheet comprises a plurality of the layers of the elastic sheet according to claim 1.

An elastic sheet and a forming method thereof are provided. The elastic sheet comprises a silicone rubber and a drug, wherein the drug is encased inside the silicone rubber in the manner of a drug storage zone, and the drug comprises an estrogen. The elastic sheet provides a preferable therapeutic effect by a micro-release of the drug, wherein the drug can be controlled into a steady release, and thus the elastic sheet provides a longer release period and preferable sustained release ability, for the treatment of uterine cavity damage. The method for forming the elastic sheet is simple from readily available materials. The easy-to-implement method is convenient for industrial large-scale production.

It is an object of the present disclosure to provide an elastic sheet and a forming method thereof. The elastic sheet has a longer release period, wherein the drug can be controlled into a steady and uniform release. In addition, an efficient therapeutic effect can be obtained by the drug in a small dose. The elastic modulus of the outer silicone rubber (in silicone rubber film for a controlled release) and/or core silicone rubber (in drug core) can be controlled, thus the elastic sheet could provide a preferable elasticity and a low drug release, especially for a micro-release of the drug. The method for forming the elastic sheet is simple from readily available materials. The easy-to-implement method provides the elastic sheet having a preferable effect in treating the damage to uterus, and is convenient for industrial large-scale production. The elastic sheet is implanted into the uterus, in order to provide a preferable therapeutic effect. In addition, the adhesion of the elastic sheet itself is effectively prevented, and a preferable fit with the uterus can be provided.

An object of the present disclosure is to provide an elastic sheet, comprising a silicone rubber and a drug, wherein the drug is encased inside the silicone rubber in the manner of a drug storage zone, and the drug comprises an estrogen.

In some embodiments, the silicone rubber has a thickness of 0.02-1 mm, such as 0.02 mm, 0.05 mm, 0.08 mm, 0.1 mm, 0.3 mm, 0.5 mm, 0.8 mm, 1 mm, etc., preferably 0.02-0.3 mm. In some embodiments, the silicone rubber has an elastic modulus of 0.5-1.2 MPa, such as 0.5 MPa, 0.6 MPa, 0.7 MPa, 0.8 MPa, 0.9 MPa, 1.0 MPa, 1.1 MPa, 1.2 MPa, preferably 0.5-0.8 MPa.

In some embodiments, the silicone rubber has a crosslink density of 1000-5000 g/mol, such as 1000 g/mol, 1500 g/mol, 2000 g/mol, 2500 g/mol, 3000 g/mol, 3500 g/mol, 4000 g/mol, 4500 g/mol, 5000 g/mol, etc., preferably 1000-3000 g/mol. In some embodiments, the silicone rubber comprises any one or at least two of heat vulcanized silicone rubber (HTV), room temperature vulcanized silicone rubber (RTV), low temperature vulcanized silicone rubber (LTV), DOWCORNING Silastic-382 medical silicone rubber, and DOWCORNING Q7 medical silicone rubber series and implantable MDX series. In some embodiments, the silicone rubber comprises any one or at least two of a self-modifying HTV, RTV solid silicone rubber, LTV solid silicone rubber, RTV liquid silicone rubber or LTV liquid silicone rubber.

In some embodiments, the drug storage zone has a thickness of 0.2-1 mm, such as 0.2 mm, 0.3 mm, 0.4 mm, 0.5 mm, 0.6 mm, 0.7 mm, 0.8 mm, 0.9 mm, 1.0 mm, etc. In some embodiments, a minimum distance from an edge of the drug storage zone to an edge of the silicone rubber is 0.5-5 mm, such as 0.5 mm, 0.6 mm, 0.7 mm, 0.8 mm, 0.9 mm, 1.0 mm, 2 mm, 3 mm, 4 Mm, 5 mm, etc. In some embodiments, the drug storage zone comprises a reactive drug storage zone and a mixed drug storage zone. In some embodiments, the drug storage zone is the reactive drug storage zone, which includes a substrate and a drug. In some embodiments, a weight ratio of the substrate to the drug is (50-99%):(50%-1%), such as 50%:50%, 55%:45%, 60%:40%, 65%:35%, 70%:30%, 75%:25%, 80%:20%, 85%:15%, 90%:10%, 95%:5%, 99%:1%, etc.

In some embodiments, the substrate is a core silicone rubber. In some embodiments, the core silicone rubber has an elastic modulus of 0.9-1.5 MPa, such as 0.9 MPa, 1.0 MPa, 1.1 MPa, 1.2 MPa, 1.3 MPa, 1.4 MPa, 1.5 MPa, etc.

In some embodiments, the efficient therapeutic effect can be obtained by a micro-release of the drug. In addition, the elastic sheet has a longer release period and a preferable sustained release ability, wherein the drug can be controlled into a steady release, for the treatment of uterine cavity damage. In some embodiments, the silicone rubber is controlled to control the micro-release of the drug to achieve an efficient therapeutic effect. Under the circumstance that the drug storage zone is the reactive drug storage zone, the drug is subjected to a first-stage sustained release through the substrate (such as the core silicone rubber), and then is subjected to a second-stage sustained release through the outer silicone rubber, thereby the micro-release of the drug can be better controlled in a stable manner with a longer release period. The elastic modulus of the core silicone rubber is greater than that of the outer silicone rubber, thus the drug core can support the outer silicone rubber. Since the elastic modulus of the silicone rubber affects the crosslink degree, the drug release would be affected if the elastic modulus is too large.

In some embodiments, the mixed drug storage zone comprises a solid drug core and/or a liquid drug core. In some embodiments, the mixed drug storage zone comprises a drug. In some embodiments, the mixed drug storage zone comprises an auxiliary material and a surfactant. In some embodiments, the mixed drug storage zone is a solid drug core, and the mixed drug storage zone comprises 1-80 wt % of drug, 10-89 wt % of auxiliary material, and 0.05-10 wt % of surfactant. In some embodiments, the mixed drug storage zone is a solid drug core, and the mixed drug storage zone comprises 50-80 wt % of drug, 19-45 wt % of auxiliary material, and 1-5 wt % of surfactant. In some embodiments, the mixed drug storage zone is a solid core, and the auxiliary material comprises any one or at least two of cocoa butter, polyethylene glycol 400-2000, petrolatum, hydroxypropyl methylcellulose, methyl cellulose, ethyl cellulose, hydroxypropyl cellulose, talc, microcrystalline fiber powder, starch, silica, dextrin, β-cyclodextrin, γ-cyclodextrin, silicone rubber, stearic acid, barium sulfate, magnesium aluminum silicate, glyceryl monostearate and povidone. In some embodiments, the mixed drug storage zone is a liquid drug core, and the auxiliary material comprises any one or at least two of glycerin, paraffin oil, simethicone and liquid silicone rubber.

In some embodiments, the surfactant comprises any one or at least two of Span 20-80, Brij class 52-76, emulsifier polyoxyethylene alkylphenol ether, polyethylene glycol 400-2000, povidone, pluronic-124, pluronic-188, sodium lauryl sulfate, sodium tetradecyl sulfonate, sodium dodecyl sulfonate, lactose, diatomaceous earth and triethanolamine. In some embodiments, the estrogen comprises any one or at least two of 17β estradiol, estrone, estriol, and estradiol derivatives. In some embodiments, the estrogen comprises any one or at least two of estradiol benzoate, estradiol valerate, ethinyl estradiol, ethinyl estradiol, conjugated estrogens, diethylstilbestrol, nylestriol and promestriene. In some embodiments, the estrogen has a mesh number of 1000-10000, e.g. 1000, 2000, 3000, 4000, 5000, 6000, 7000, 8000, 9000, 10000, etc., preferably 3000-8000.

In some embodiments, the drug further comprises a drug for improving endometrial blood flow and/or a colony stimulating factor. In some embodiments, the drug for improving endometrial blood flow comprises any one or at least two of aspirin, sildenafil citrate, pentoxifylline (PTX) and vitamin E, L-arginine, and low molecular weight heparin. In some embodiments, the colony stimulating factor includes granulocyte colony stimulating factor (G-CSF), and/or granulocyte-macrophage colony stimulating factor (GM-CSF). In some embodiments, a weight ratio of the estrogen to the drug for improving endometrial blood flow is 1:(0.1-1), such as 1:0.1, 1:0.2, 1:0.3, 1:0.4, 1:0.5, 1:0.6, 1:0.7, 1:0.8, 1:0.9, 1:1, etc., preferably 1:(0.3-0.6). In some embodiments, a weight ratio of the colony stimulating factor to the estrogen is (0.05-0.5):1, such as 0.05:1, 0.1:1, 0.15:1, 0.2:1, 0.25:1, 0.3:1, 0.35:1, 0.4:1, 0.45:1, 0.5:1, etc.

In some embodiments, the elastic sheet has a thickness of 0.1-4 mm, such as 0.1 mm, 0.5 mm, 0.8 mm, 1 mm, 1.2 mm, 1.5 mm, 1.8 mm, 2 mm, 2.2 mm, 2.5 mm, 2.8 mm, 3 mm, 3.2 mm, 3.5 mm, 3.8 mm, 4 mm, etc., preferably 0.2-1 mm. In some embodiments, the elastic sheet has a sustained release period of 3-90 days, such as 3 days, 10 days, 20 days, 30 days, 40 days, 50 days, 60 days, 70 days, 80 days, 90 days, etc. In some embodiments, the elastic sheet has a shape of an inverted trapezoid. In some embodiments, the elastic sheet has a shape with a big upper end and a small lower end. After the implantation, the upper end corresponds to the uterine fundus, and the lower end corresponds to the uterine cervix at an intrauterine opening which is beneficial for the fit to the uterus. In some embodiments, the inverted trapezoid has a height of 25-35 mm (such as 25 mm, 26 mm, 27 mm, 28 mm, 29 mm, 30 mm, 31 mm, 32 mm, 33 mm, 34 mm, 35 mm, etc.), an upper bottom of 20-40 mm (such as 20 mm, 22 mm, 25 mm, 27 mm, 30 mm, 32 mm, 35 mm, 37 mm, 40 mm, etc.), and a lower bottom of 5-15 mm (such as 5 mm, 6 mm, 7 mm, 8 mm, 9 mm, 10 mm, 11 mm, 12 mm, 13 mm, 14 mm, 15 mm, etc.).

Another object of the present disclosure is to provide a method forming the elastic sheet. The method comprises of encasing a drug storage zone inside a silicone rubber to form the elastic sheet. The method forming the elastic sheet is simple from readily available materials. The easy-to-implement method is convenient for industrial large-scale application.

In some embodiments, the drug storage zone is the reactive drug storage zone, and the method for forming the drug storage zone comprises of mixing, crosslinking and solidifying a core silicone rubber and a drug to form the drug storage zone. In some embodiments, the crosslinking is realized by vulcanization. In some embodiments, a surfactant is added during the crosslinking.

In some embodiments, the drug storage zone is the reactive drug storage zone, and the method for forming the drug storage zone comprises of hot-pressing the silicone rubber, and placing the reactive drug storage zone on the hot-pressed silicone rubber leaving a 0.5-5 mm edge-sealing position to obtain a film; and hot-pressing two films or two folded portions of one film to obtain the elastic sheet. In some embodiments, the reactive drug storage zone is placed on the hot-pressed silicone rubber leaving a 3-5 mm edge-sealing position. In some embodiments, the drug storage zone is the mixed drug storage zone, and the method for forming the drug storage zone comprises of physically mixing a drug, an optional auxiliary material and a surfactant to obtain the mixed drug storage zone. In some embodiments, the mixed drug storage zone is a solid drug core, and water is added during the mixing.

In some embodiments, the mixed drug storage zone is a solid drug core, and the method for forming the drug storage zone comprises of hot-pressing the silicone rubber, and placing the mixed drug storage zone on the hot-pressed silicone rubber leaving a 0.5-5 mm edge-sealing position to obtain a film; and hot-pressing two films or two folded portions of one film to obtain the elastic sheet. In some embodiments, the mixed drug storage zone is placed on the hot-pressed silicone rubber leaving a 3-5 mm edge-sealing position.

In some embodiments, the mixed drug storage zone is a liquid drug core, and the method for forming the drug storage zone comprises of hot pressing the silicone rubber into a film, hot-pressing two films or two folded portions of one film to obtain a prefabricated silicone rubber capsule, and injecting a liquid drug core into the prefabricated silicone rubber capsule to obtain the elastic sheet.

The elastic sheet of the present disclosure provides several benefits compared with the prior art. In some embodiments, the efficient therapeutic effect can be obtained by a micro-release of the drug. In addition, the elastic sheet has a longer release period and a preferable sustained release ability, wherein the drug can be controlled into a steady release, for the treatment of uterine cavity damage. Since the elastic modulus of the core silicone rubber and the outer silicone rubber can be controlled, on one hand, the core silicone rubber can be used to support the outer silicone rubber, on the other hand, the outer silicone rubber can be used to control the micro-release of the drug in a stable manner to provide a longer release period to achieve a preferable therapeutic effect. The method for forming the elastic sheet is simple from readily available materials. The method is convenient for industrial large-scale production with a low cost.

Embodiment 1

The present embodiment provides an elastic sheet comprising a silicone rubber and a drug storage zone encased inside the silicone rubber, wherein the drug storage zone comprises a core silicone rubber and a drug. The silicone rubber has a thickness of 0.02 mm, an elastic modulus of 0.7 MPa, and a crosslink density of 2000 g/mol. The drug storage zone has a thickness of 0.2 mm, an elastic modulus of 1.3 MPa. The minimum distance from an edge of the drug storage zone to an edge of the silicone rubber is 3 mm. The drug is estradiol, with a mesh number of 2000. The content of estradiol per elastic sheet is 100 mg. The embodiment further provides a method for forming an elastic sheet, which comprises following steps:
  i. 5 g of 17β estradiol (average particle size 2,000 mesh), 30 g of HTV medical silicone rubber (molecular weight 20-100 million), 10 g of silica, 5 g of hydroxy silicone oil, 6 g of medical barium sulfate, 0.5 g of iron oxide red, and 2 g of benzoyl peroxide were kneaded to a uniform on a rubber mixer, and hot pressed on a flat vulcanizer to form a sheet having a thickness of 0.2 mm, and then cut into a desired shape to obtain a drug storage zone.
  ii. 30 g of HTV medical silicone rubber (molecular weight 20-100 million), 10 g of silica, 5 g of hydroxy silicone oil, 6 g of medical barium sulfate, 0.5 g of iron oxide red, and 2 g of benzoyl peroxide were kneaded to a uniform on a rubber mixer, and hot pressed on a flat vulcanizer to form a sheet having a thickness of 0.02 mm, and then cut into a desired shape to obtain an outer silicone rubber.
  iii. The drug storage zone of step i. was encased inside the outer silicone rubber of step ii and vulcanized by heating on a flat vulcanizer to form an elastic sheet.

The sample was dissolved in PBS solution at 37° C. on a drug dissolution tester, and the dissolution content was measured by HPLC.

Comparative Example 1

The difference from the Embodiment 1 only lies in the elastic sheet without an outer silicone rubber.

Figure 49:
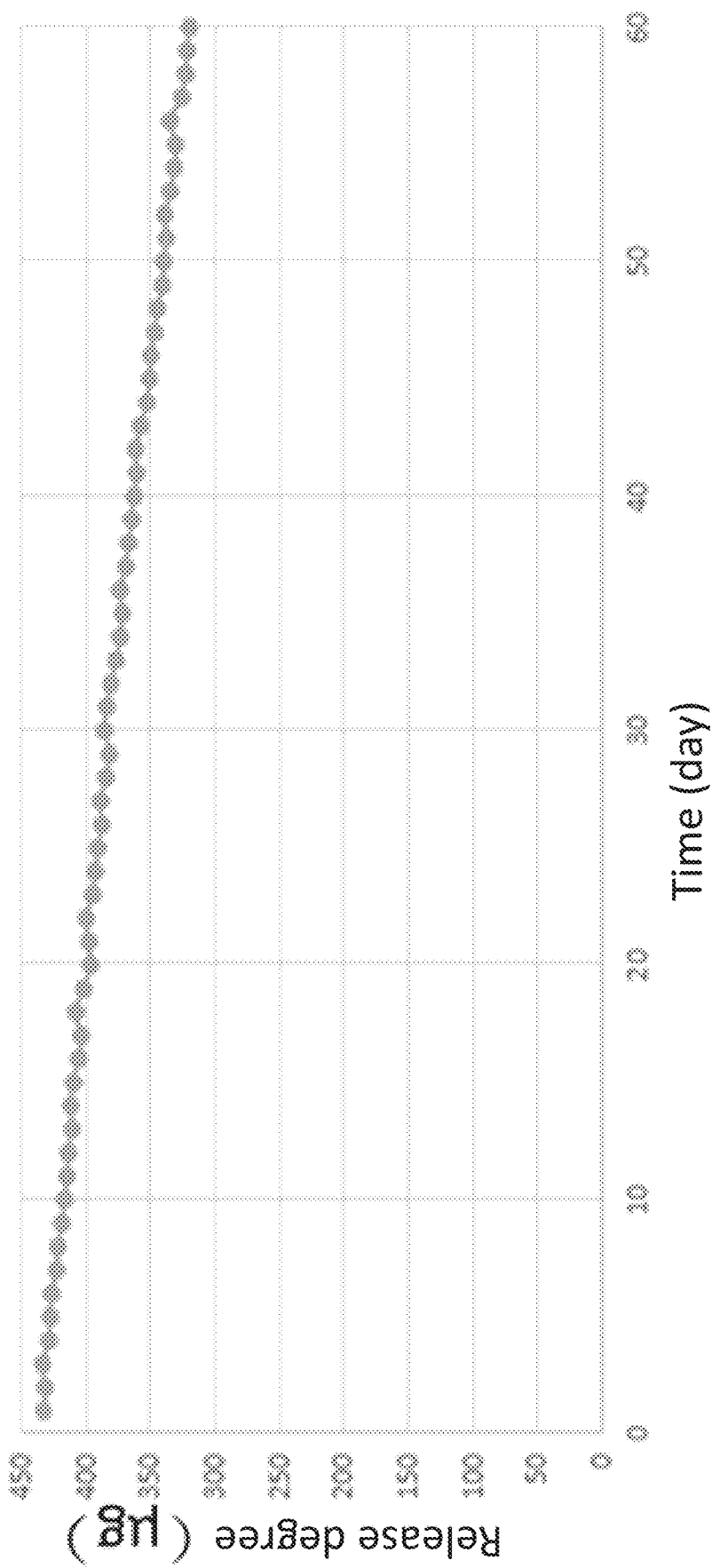
FIG. 49 shows the drug release curve of the elastic sheet of Embodiment 1.
Figure 50:
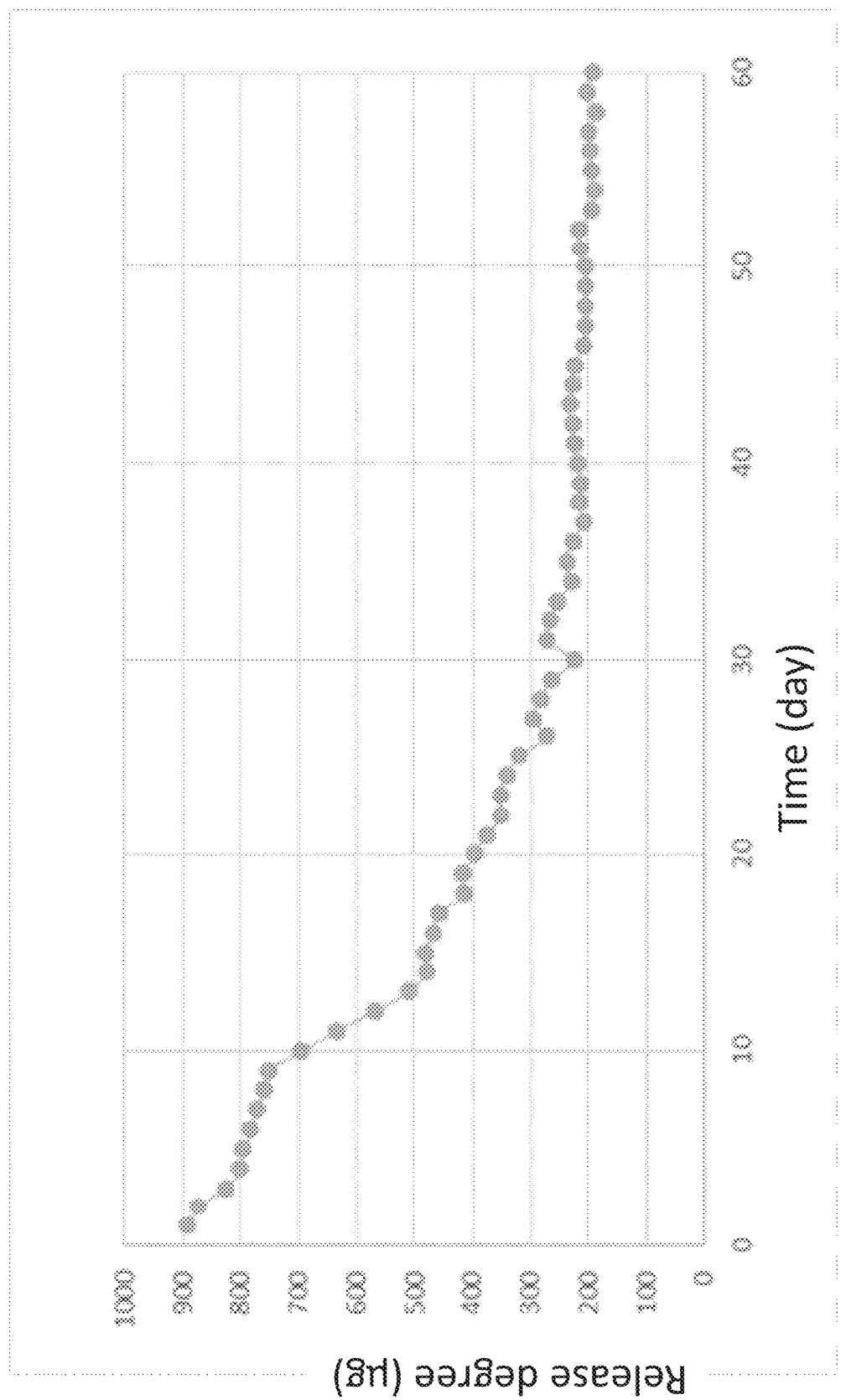
FIG. 50 shows the drug release curve of the elastic sheet of Comparative example 1.

FIG. 49 shows the drug release curve of the elastic sheet of Embodiment 1, and FIG. 50 shows the drug release curve of the elastic sheet of Comparative example 1. Compared with Comparative example 1, the Embodiment 1 provides a further silicone rubber film for a controlled-release outside of the drug storage zone to provide a smaller drug release. However, the daily drug release is gentle without the sudden release in the early stage of the matrix-type elastic sheet. It is beneficial for long-term drug release in a small dose.

Embodiment 2

The present embodiment provides an elastic sheet comprising a silicone rubber and a drug storage zone encased inside the silicone rubber, wherein the drug storage zone comprises a core silicone rubber and a drug. The silicone rubber has a thickness of 0.02 mm, an elastic modulus of 0.7 MPa, and a crosslink density of 2000 g/mol. The drug storage zone has a thickness of 0.2 mm, an elastic modulus of 1.3 MPa. The minimum distance from an edge of the drug storage zone to an edge of the silicone rubber is 5 mm. The drug is estradiol, with a mesh number of 2000. The content of estradiol per elastic sheet is 100 mg.

The embodiment further provides a method for forming an elastic sheet, which comprises following steps:
  i. 5 g of 17β estradiol (average particle size 2,000 mesh), 3 g Span 20, 30 g of HTV medical silicone rubber (molecular weight 20-100 million), 10 g of silica, 5 g of hydroxy silicone oil, 6 g of medical barium sulfate, 0.5 g of iron oxide red, and 2 g of benzoyl peroxide were kneaded to a uniform on a rubber mixer, and hot pressed on a flat vulcanizer to form a sheet having a thickness of 0.2 mm, and then cut into a desired shape to obtain a drug storage zone.
  ii. 30 g of HTV medical silicone rubber (molecular weight 20-100 million), 10 g of silica, 5 g of hydroxy silicone oil, 6 g of medical barium sulfate, 0.5 g of iron oxide red, and 2 g of benzoyl peroxide were kneaded to a uniform on a rubber mixer, and hot pressed on a flat vulcanizer to form a sheet having a thickness of 0.02 mm, and then cut into a desired shape to obtain an outer silicone rubber.
  iii. The drug storage zone of step i. was encased inside the outer silicone rubber of step ii by a medical glue to form an elastic sheet.

The sample was dissolved in PBS solution at 37° C. on a drug dissolution tester, and the dissolution content was measured by HPLC.

Figure 51:
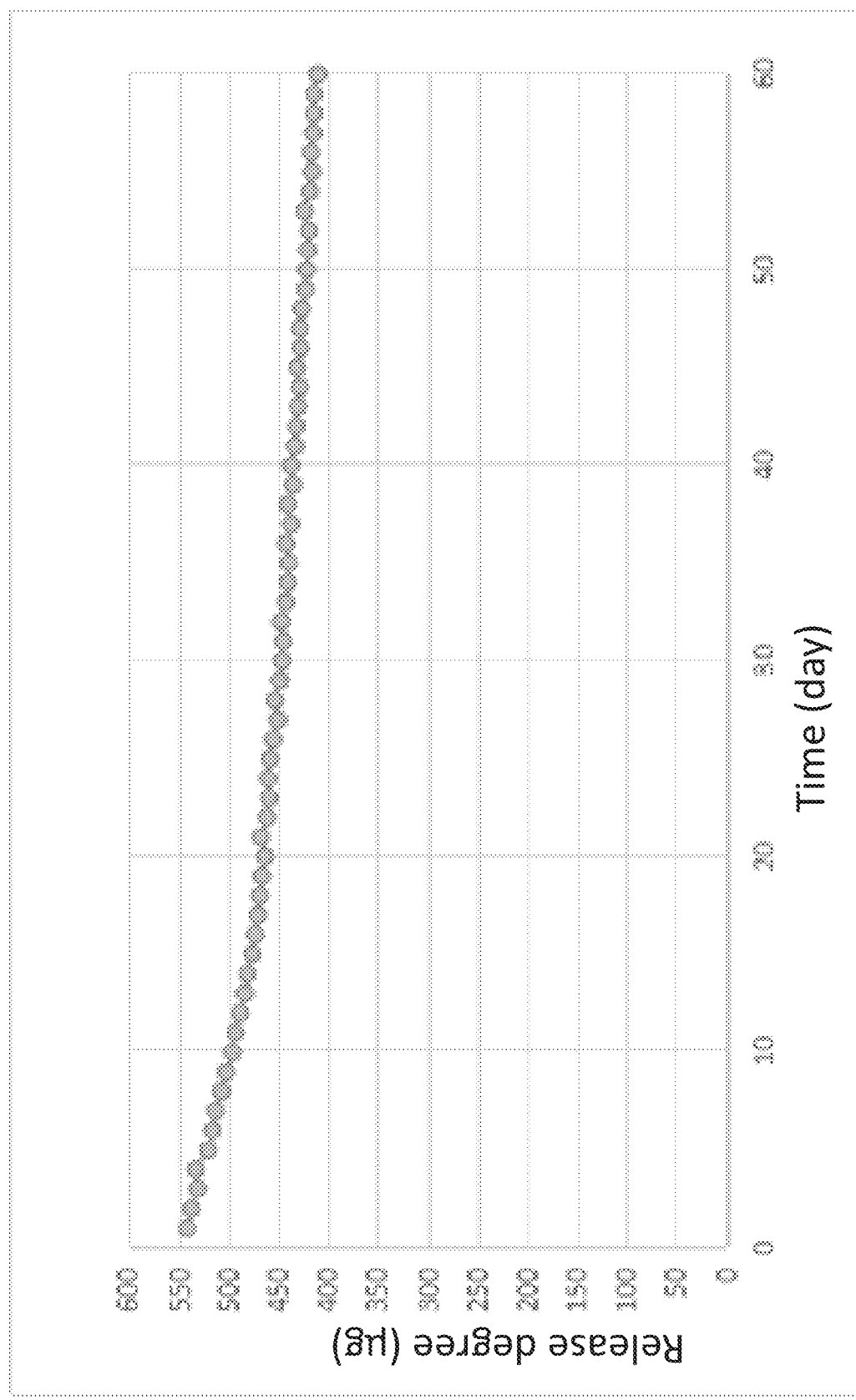
FIG. 51 shows the drug release curve of the elastic sheet of Embodiment 2.

FIG. 51 shows the drug release curve of the elastic sheet of Embodiment 2. Obviously, the drug dissolution can be increased by the addition of the surfactant, and the daily drug release maintains in a gentle manner.

Embodiment 3

The present embodiment provides an elastic sheet comprising a silicone rubber and a drug storage zone encased inside the silicone rubber, wherein the drug storage zone comprises a core silicone rubber and a drug. The silicone rubber has a thickness of 0.5 mm, an elastic modulus of 0.5 MPa, and a crosslink density of 5000 g/mol. The drug comprises estradiol with a mesh number of 5000 and aspirin. The content of estradiol per elastic sheet is 50 mg, and the content of aspirin per elastic sheet is 10 mg.

The embodiment further provides a method for forming an elastic sheet, which comprises following steps:
  i. 5 g of 17β estradiol (average particle size 5,000 mesh), 1 g of aspirin, 3 g of silica, 0.5 g of simethicone, 0.3 g of povidone and 4 g of distilled water were uniformly mixed. An appropriate volume was placed in a mold to form a solid drug core, and thus obtain a drug storage zone in a solid form with 50 mg of estradiol and 10 mg of aspirin.
  ii. 30 g of HTV medical silicone rubber (molecular weight 20-100 million), 10 g of silica, 5 g of hydroxy silicone oil, 6 g of medical barium sulfate, 0.5 g of iron oxide red, and 2 g of benzoyl peroxide were kneaded to a uniform on a rubber mixer, and hot pressed on a flat vulcanizer to form a sheet having a thickness of 0.5 mm, and then cut into a desired shape to obtain an outer silicone rubber.
  iii. The drug storage zone of step i. was encased inside the outer silicone rubber of step ii by vulcanization in a mold to form an elastic sheet, wherein the drug core is hand-pressed into a uniform powder form.

The sample was dissolved in PBS solution at 37° C. on a drug dissolution tester, and the dissolution content was measured by HPLC.

Figure 52:
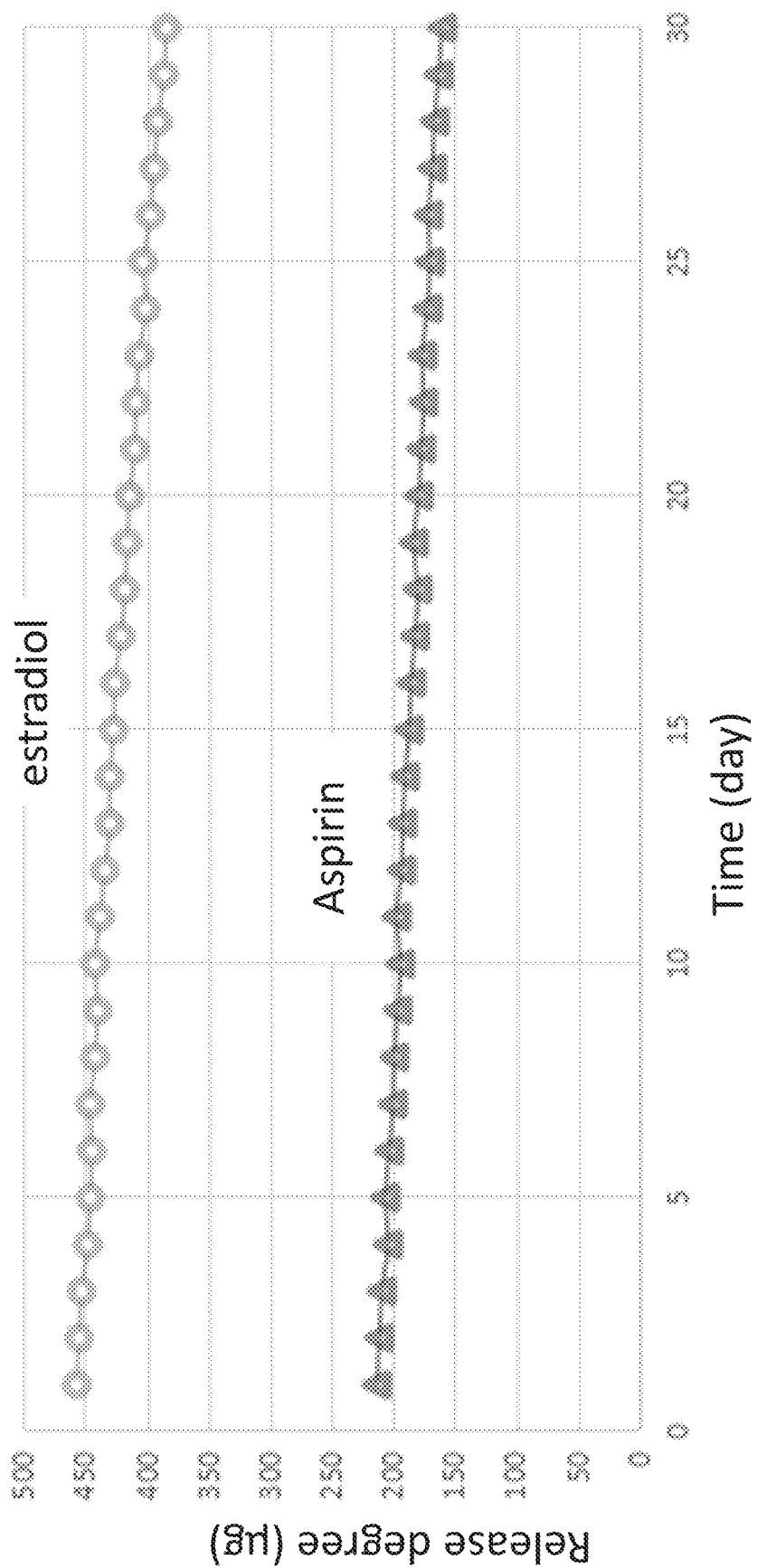
FIG. 52 shows the drug release curve of the elastic sheet of Embodiment 3.

FIG. 52 shows the drug release curve of the elastic sheet of Embodiment 3. Obviously, the daily release of estradiol and aspirin maintains in a gentle manner.

Embodiment 4

The present embodiment provides an elastic sheet comprising a silicone rubber and a drug storage zone encased inside the silicone rubber, wherein the drug storage zone is in a liquid form and comprises a core silicone rubber and a drug. The silicone rubber has a thickness of 0.3 mm, an elastic modulus of 0.7 MPa, and a crosslink density of 200 g/mol. The drug is estradiol with a mesh number of 5000. The content of estradiol per elastic sheet is 75 mg.

The embodiment further provides a method for forming an elastic sheet, which comprises following steps.
  i. 30 g of HTV medical silicone rubber (molecular weight 20-100 million), 10 g of silica, 5 g of hydroxy silicone oil, 6 g of medical barium sulfate, 0.5 g of iron oxide red, and 2 g of benzoyl peroxide were kneaded to a uniform on a rubber mixer, and hot pressed on a flat vulcanizer to form a sheet having a thickness of 0.3 mm, and then cut into a desired shape. An injection port was left after the vulcanized seal, to obtain an outer silicone rubber capsule.
  ii. 2 g of 17β estradiol (average particle size 5,000 mesh), 5 g liquid silicone rubber, 0.5 g of simethicone, and 2 g of glycerin were mixed to a uniform, which was then injected into the outer silicone rubber capsule of step i. through the injection port. Air bubbles were removed before sealing the injection port to form an elastic sheet.

The sample was dissolved in PBS solution at 37° C. on a drug dissolution tester, and the dissolution content was measured by HPLC.

Figure 53:
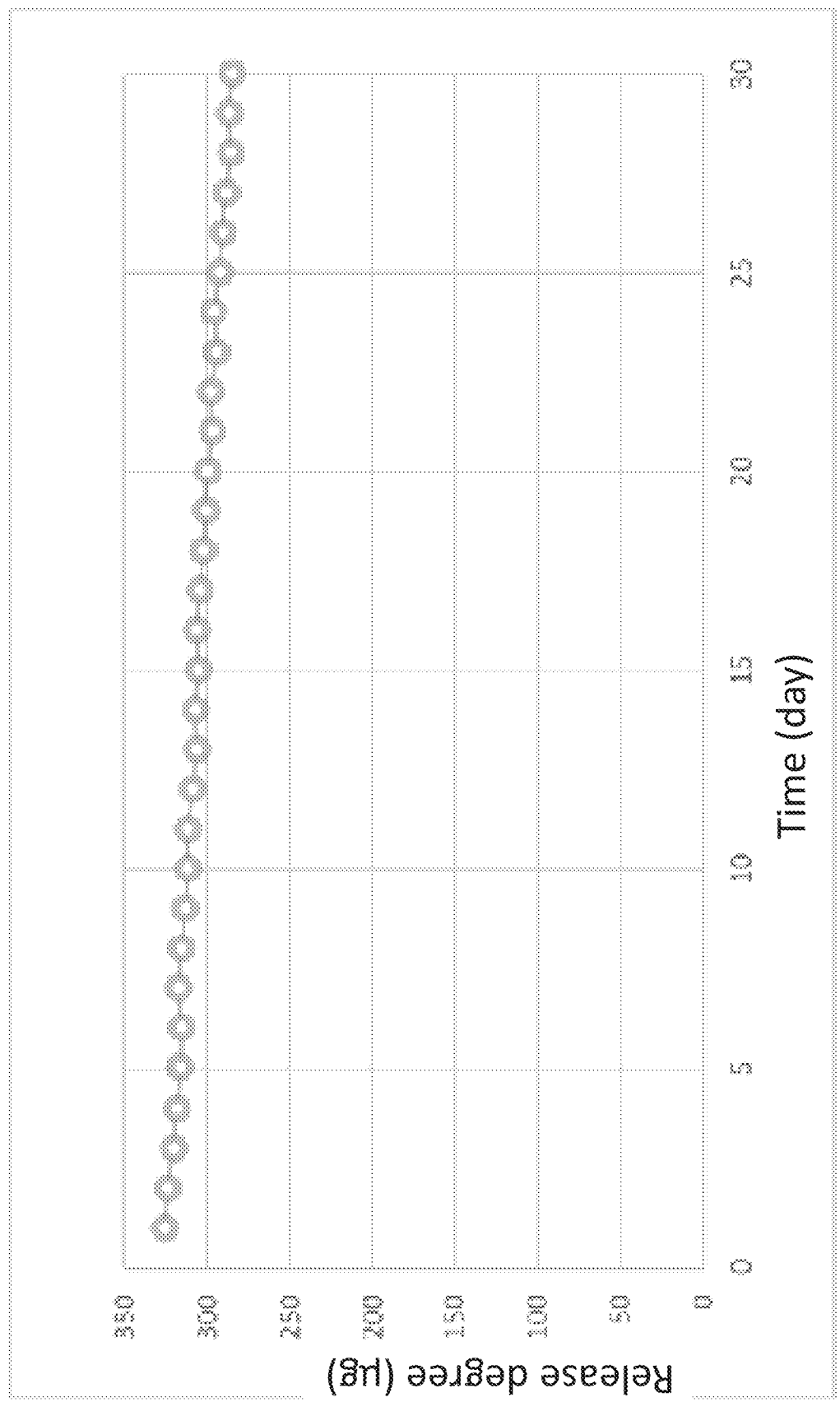
FIG. 53 shows the drug release curve of the elastic sheet of Embodiment 4.

FIG. 53 shows the drug release curve of the elastic sheet of Embodiment 4. Obviously, the daily drug release maintains in a gentle manner.

Comparative Example 2

The difference from the Embodiment 1 only lies in the mesh number 800 of estradiol.

The sample was dissolved in PBS solution at 37° C. on a drug dissolution tester, and the dissolution content was measured by HPLC. The result showed that within 30 days, the maximum amount of drug dissolution was 175 μg/d in the first 3 days, and then the drug dissolution was gradually stabilized, wherein the average drug release in 30 days was 65 μg/d.

Obviously, the drug with a bigger mesh number and a bigger specific surface area is less likely to be released, and vice versa. Thus, the mesh number of the drug should be above 500 to provide a preferable release. However, according to the drug micronization, since the production of the drug with a mesh number above 10,000 has a poor stability and a high cost, the mesh number of the drug should not exceed 10,000.

Comparative Example 3

The difference from the Embodiment 1 only lies in the elastic modulus of the silicone rubber, wherein the core silicone rubber has an elastic modulus of 0.5 MPa, and the outer silicone rubber has an elastic modulus of 0.3 MPa, with a crosslink density of 6000 g/mol.

The sample was dissolved in PBS solution at 37° C. on a drug dissolution tester, and the dissolution content was measured by HPLC. The result showed that within 30 days, the maximum amount of drug dissolution was 257 μg/d in the first 3 days, and then the drug dissolution was gradually stabilized, wherein the average drug release in 30 days was 93 μg/d.

The New Zealand rabbits were tested. Before the implantation, 6 trauma models were obtained by surgical curettage. During the implantation, the elastic sheet was curled and then flattened with an auxiliary device. After 30 days, different degrees of adhesions happened in the uteri of the test animals of the present Comparative example.

Comparative Example 4

The difference from the Embodiment 3 only lies in the elastic sheet without the surfactant of povidone in the solid drug core.

The sample was dissolved in PBS solution at 37° C. on a drug dissolution tester, and the dissolution content was measured by HPLC. The result showed that within 30 days, the maximum amount of estradiol dissolution was 169 μg/d and the maximum amount of aspirin dissolution was 93 µg/d in the first 3 days, and then the drug dissolution was gradually stabilized, wherein the average estradiol release in 30 days was 133 µg/d and the average aspirin release was 58 µg/d.

Obviously, the drug dissolution can be increased by the addition of the surfactant, and the daily drug release maintains in a gentle manner.

1. An elastic sheet, comprising: a silicone rubber; and a drug; wherein the drug is encased inside the silicone rubber in the manner of a drug storage zone, and the drug comprises an estrogen.
2. The elastic sheet according to the claim 1, wherein the silicone rubber has a thickness of 0.02-1 mm, preferably 0.02-0.3 mm; preferably, the silicone rubber has an elastic modulus of 0.5-1.2 MPa, preferably 0.5-0.8 MPa; preferably, the silicone rubber has a crosslink density of 1000-5000 g/mol, preferably 1000-3000 g/mol; preferably, the silicone rubber comprises any one or at least two of heat vulcanized silicone rubber (HTV), room temperature vulcanized silicone rubber (RTV), low temperature vulcanized silicone rubber (LTV), DOWCORNING Silastic-382 medical silicone rubber, and DOWCORNING Q7 medical silicone rubber series and implantable MDX series; preferably, the silicone rubber comprises any one or at least two of a self-modifying HTV, RTV solid silicone rubber, LTV solid silicone rubber, RTV liquid silicone rubber or LTV liquid silicone rubber.
3. The elastic sheet according to the claim 1, wherein the drug storage zone has a thickness of 0.2-1 mm; preferably, a minimum distance from an edge of the drug storage zone to an edge of the silicone rubber is 0.5-5 mm; preferably, the drug storage zone comprises a reactive drug storage zone and a mixed drug storage zone; preferably, the drug storage zone is the reactive drug storage zone which includes a substrate and a drug; preferably, a weight ratio of the substrate to the drug is (50-99%):(50%-1%); preferably, the substrate is a core silicone rubber; preferably, the core silicone rubber has an elastic modulus of 0.9-1.5 MPa, preferably 1.2-1.5 MPa.
4. The elastic sheet according to the claim 3, wherein the mixed drug storage zone comprises a solid drug core and/or a liquid drug core; preferably, the mixed drug storage zone comprises a drug; preferably, the mixed drug storage zone comprises an auxiliary material and a surfactant; preferably, the mixed drug storage zone is a solid drug core, and the mixed drug storage zone comprises 1-80 wt % of drug, 10-89 wt % of auxiliary material, and 0.05-10 wt % of surfactant; preferably, the mixed drug storage zone is a solid drug core, and the mixed drug storage zone comprises 50-80 wt % of drug, 19-45 wt % of auxiliary material, and 1-5 wt % of surfactant.
5. The elastic sheet according to the claim 1, wherein the estrogen comprises any one or at least two of 17β estradiol, estrone, estriol, and estradiol derivatives; preferably, the estrogen comprises any one or at least two of estradiol benzoate, estradiol valerate, ethinyl estradiol, ethinyl estradiol, conjugated estrogens, diethylstilbestrol, nylestriol and promestriene; preferably, the estrogen has a mesh number of 1000-10000, preferably 3000-8000.
6. The elastic sheet according to the claim 1, wherein the drug further comprises a drug for improving endometrial blood flow and/or a colony stimulating factor; preferably, the drug for improving endometrial blood flow comprises any one or at least two of aspirin, sildenafil citrate, pentoxifylline (PTX) and vitamin E, L-arginine, and low molecular weight heparin; preferably, the colony stimulating factor includes granulocyte colony stimulating factor (G-CSF), and/or granulocyte-macrophage colony stimulating factor (GM-CSF); preferably, a weight ratio of the estrogen to the drug for improving endometrial blood flow is 1:(0.1-1), preferably 1:(0.3-0.6); preferably, a weight ratio of the colony stimulating factor to the estrogen is (0.05-0.5):1.
7. The elastic sheet according to the claim 1, wherein the elastic sheet has a thickness of 0.1-4 mm, preferably 0.2-1 mm; preferably, the elastic sheet has a sustained release period of 3-90 days; preferably, the elastic sheet has a shape of an inverted trapezoid; preferably, the inverted trapezoid has a height of 25-35 mm, an upper bottom of 20-40 mm, and a lower bottom of 5-15 mm.
8. A method for forming the elastic sheet according to claim 1, comprising of encasing a drug storage zone drug inside a silicone rubber to form the elastic sheet; preferably, the drug storage zone is the reactive drug storage zone, and the method for forming the drug storage zone comprises of mixing, crosslinking and solidifying a core silicone rubber and a drug to form the drug storage zone; preferably, the crosslinking is realized by vulcanization; preferably, a surfactant is added during the crosslinking; preferably, the drug storage zone is the reactive drug storage zone, and the method for forming the drug storage zone comprises of hot-pressing the silicone rubber, and placing the reactive drug storage zone on the hot-pressed silicone rubber leaving a 0.5-5 mm edge-sealing position to obtain a film; and hot-pressing two films or two folded portions of one film to obtain the elastic sheet.
9. The method according to the claim 8, wherein the drug storage zone is the mixed drug storage zone, and the method for forming the drug storage zone comprises of physically mixing a drug, an optional auxiliary material, and a surfactant to obtain the mixed drug storage zone preferably, the mixed drug storage zone is a solid drug core, and water is added during the mixing; preferably, the mixed drug storage zone is a solid drug core, and the method for forming the drug storage zone comprises of hot-pressing the silicone rubber, and placing the mixed drug storage zone on the hot-pressed silicone rubber leaving a 0.5-5 mm edge-sealing position to obtain a film; and hot-pressing two films or two folded portions of one film to obtain the elastic sheet; preferably, the mixed drug storage zone is a liquid drug core, and the method for forming the drug storage zone comprises of hot pressing the silicone rubber into a film, hot-pressing two films or two folded portions of one film to obtain a prefabricated silicone rubber capsule, and injecting a liquid drug core into the prefabricated silicone rubber capsule to obtain the elastic sheet.

An elastic sheet and a forming method thereof are provided. The elastic sheet comprises a silicone rubber and a drug, wherein the drug is carried by an outer surface of the silicone rubber as a coating, and the drug comprises an estrogen. The elastic sheet provides a preferable therapeutic effect in a low dose. In addition, the elastic sheet provides a longer release period and preferable sustained release ability, for the treatment of uterine cavity damage. The method for forming the elastic sheet is simple from readily available materials. The easy-to-implement method is convenient for industrial large-scale production.

It is an object of the present disclosure to provide an elastic sheet and a forming method thereof. The elastic sheet has a longer release period, wherein the drug can be controlled into a steady release. In addition, an efficient therapeutic effect can be obtained by the drug in a small dose. Further, an adhesive force between the modified silicone rubber and the coating on the modified silicone rubber can be improved by modifying the surface of the silicone rubber. The method for forming the elastic sheet is simple from readily available materials. The easy-to-implement method provides the elastic sheet having a preferable effect in treating the damage to uterus, and is convenient for industrial large-scale production. The elastic sheet is implanted into the uterus, in order to provide a preferable therapeutic effect. In addition, the adhesion of the elastic sheet itself is effectively prevented, and a preferable fit with the uterus can be provided.

An object of the present disclosure is to provide an elastic sheet, comprising a silicone rubber and a drug, wherein the drug is carried by an outer surface of the silicone rubber as a coating, and the drug comprises an estrogen.

The elastic sheet of some embodiments provides an efficient therapeutic effect by the drug in a small dose. The elastic sheet has a longer release period and preferable sustained release ability for the treatment of uterine cavity damage. In some embodiments, the drug is atomized to particles which are sprayed onto the outer surface of the silicone rubber. In some embodiments, the silicone rubber is obtained by treating a surface of a prefabricated silicone rubber. In some embodiments, the treating comprises any one or at least two of a plasma treatment, a swelling treatment, a sandblasting treatment, a sanding treatment, a texture treatment, an electrostatic treatment or a wetting treatment.

In some embodiments, the drug is atomized to particles with a particle diameter of 50 nm-500 μm which are sprayed onto the outer surface of the silicone rubber. In some embodiments, the particle diameter of the drug atomized particles is 10-500 μm. In other embodiments, the particle diameter of the drug atomized particles is non-uniform, but generally within the above particle diameter range. In some embodiments, the particles are normally distributed in the above particle diameter range.

In some embodiments, the elastic sheet comprises a silicone rubber and a coating on the surface of the silicone rubber, wherein the silicone rubber has high stability and biocompatibility, and the silicone rubber has good memory elasticity to ensure good shape retention in the body. The prefabricate silicone rubber can be modified on the surface by swelling or the like. For example, the prefabricate silicone rubber can be immersed in a volatile organic solvent to replace the moisture inside the prefabricate silicone rubber. So that an adhesive force between the modified silicone rubber and the coating can be improved. The coating deforms correspondingly in case of the deformation of the elastic sheet, in order to maintain the well adhesion between the coating and the silicone rubber. Since the coating is formed by spraying, the drug can be uniformly distributed on the surface of the silicone rubber, which facilitates the uniform and stable release of the drug, in order to obtain a preferable therapeutic effect. In addition, local damage to the uterus can be treated by a local spraying coating.

In some embodiments, the coating comprises a drug and a controlled release factor. In some embodiments, a weight ratio of the drug to the controlled release factor is (10%-90%):(90%-10%), such as 10%:90%, 20%:80%, 30%:70%, 40%:60%, 50%:50%, 60%:40%, 70%:30%, 80%:20%, 90%:10%, etc.

In some embodiments, the coating has a thickness of 0.02-0.2 mm, such as 0.02 mm, 0.05 mm, 0.07 mm, 0.1 mm, 0.12 mm, 0.15 mm, 0.17 mm, 0.2 mm, etc. The coating of some embodiments has a thickness of 0.02-0.2 mm in order to provide the elastic sheet with sufficient support elasticity without increasing the overall thickness, simultaneously provide the elastic sheet with a sufficient dosage and a longer release period to provide a preferable therapeutic effect. Under the circumstance that the thickness of the coating is less than 0.02 mm, the drug amount and release period would be reduced, and therapeutic effect will be affected. Under the circumstance that the thickness of the coating is too high, the overall thickness of the elastic sheet may be affected, and the drug cannot be completely released. That is to say, the starting materials are wasted after the end of the treatment period.

In some embodiments, the controlled release factor is a degradable polymer. In some embodiments, the controlled release factor is a degradable polymer, and most of the drug is released by degradation of the degradable polymer. During the use of the sheet, the degradation process of the degradable polymer is relatively uniform and stable, thus the drug release is relatively more uniform and stable, in order to provide a preferably therapeutic effect. Therefore, there is no significant requirement for the particle diameter of the drug to the drug release, and it is not necessary to do the micronization treatment.

In some embodiments, the controlled release factor comprises any one or at least two of chitosan, gelatin, algin, starch, hyaluronic acid, cellulose and its derivatives, polylactide, polylactide-glycolide, polyglycolide, polylactic acid, L-polylactic acid, D-polylactic acid, polyvinyl alcohol, polyvinylpyrrolidone, polyglycolic acid/polylactic acid copolymer, polyethylene glycol, polycaprolactone, polyorthoesters and polyglycolic acid.

In some embodiments, a weight ratio of the drug to the degradable polymer is (30%-50%):(70%-50%), such as 30%:70%, 35%:65%, 40%:60%, 45%:55%, 50%:50%, etc. In some embodiments, the elastic sheet has estrogen of 10 mg-200 mg, such as 10 mg, 30 mg, 50 mg, 70 mg, 100 mg, 120 mg, 150 mg, 170 mg, 200 mg, etc. In some embodiments, the estrogen has a daily release of 10 μg-4 mg, such as 10 μg, 100 μg, 500 μg, 800 μg, 1 mg, 2 mg, 3 mg, 4 mg, etc.

Usually, when the basal layer of the uterus is damaged, the damaged part does not change with the change of hormones. Therefore, after the adhesion is separated by a known method, since the adhesive portion still cannot produce the functional layer, adhesion is likely to occur again. Surprisingly, according to some embodiments, the estrogen is loaded on the silicone rubber, and thus the endometrial basal layer is continuously activated through drug stimulation, allowing for the endometrial basal layer to re-proliferate the functional layers, thereby restoring the normal endometrial structure and completely preventing adhesions. In particular, in patients with scarred uterus or uterine fibrosis, it is only necessary to surgically separate the fibrotic endometrial basal layer or scar to create a wound surface, so that the regeneration ability of endometrial functional layers can be activated through continuous estrogen stimulation. In some embodiments, the estrogen has a daily release of 10 μg-4 mg to a threshold of action for at least one week to provide a sustained release system with a controlled release rate and a release period. In some embodiments, the estrogen has a daily release of estrogen of 20 µg-1 mg, and the elastic sheet has estrogen of 10 mg-200 mg.

In some embodiments, the estrogen comprises any one or at least two of 17β estradiol, estrone, estriol, and estradiol derivatives. In some embodiments, the estrogen comprises any one or at least two of estradiol benzoate, estradiol valerate, ethinyl estradiol, ethinyl estradiol, conjugated estrogens, diethylstilbestrol, nylestriol and promestriene.

Compared with oral administration or other administration methods, the estrogen of the present disclosure is locally targeted and released, and acts to stimulate endometrial hyperplasia without side effects such as hormonal disturbance caused by a large dose.

In some embodiments, the drug further comprises a drug for improving endometrial blood flow and/or a colony stimulating factor. In some embodiments, the colony stimulating factor is for modulating local immunity of the uterine cavity, which is capable of promoting endometrial basal cell proliferation.

In some embodiments, the estrogen, drug for improving endometrial blood flow and colony stimulating factor work together, in order to increase capillary blood supply, promote local targeted release of the drug, and promote endometrial hyperplasia. The efficient therapeutic effect can be obtained in a low dose without side effects such as hormonal disturbance caused by a large dose. In some embodiments, the drug for improving endometrial blood flow comprises any one or at least two of aspirin, sildenafil citrate, pentoxifylline (PTX) and vitamin E, L-arginine, and low molecular weight heparin. In some embodiments, the colony stimulating factor includes granulocyte colony stimulating factor (G-CSF), and/or granulocyte-macrophage colony stimulating factor (GM-CSF).

In some embodiments, a weight ratio of the estrogen to the drug for improving endometrial blood flow is 1:(0.1-1), such as 1:0.1, 1:0.2, 1:0.3, 1:0.4, 1:0.5, 1:0.6, 1:0.7, 1:0.8, 1:0.9, 1:1, etc., preferably 1:(0.3-0.6). In some embodiments, a weight ratio of the colony stimulating factor to the estrogen is (0.05-0.5):1, such as 0.05:1, 0.1:1, 0.15:1, 0.2:1, 0.25:1, 0.3:1, 0.35:1, 0.4:1, 0.45:1, 0.5:1, etc.

In some embodiments, the prefabricated silicone rubber comprises any one or at least two of heat vulcanized silicone rubber (HTV), room temperature vulcanized silicone rubber (RTV), low temperature vulcanized silicone rubber (LTV), DOWCORNING Silastic-382 medical silicone rubber, and DOWCORNING Q7 medical silicone rubber series and implantable MDX series.

In some embodiments, the elastic sheet has an elastic modulus of 0.5-3 MPa, such as 0.9 MPa, 1.0 MPa, 1.1 MPa, 1.2 MPa, 1.3 MPa, 1.4 MPa, 1.5 MPa, 1.8 MPa, 2.0 MPa, 2.5 MPa, etc., preferably 1.0-2.0 MPa. In some embodiments, the elastic sheet has a thickness of 0.1-4 mm, such as 0.1 mm, 0.5 mm, 0.8 mm, 1 mm, 1.2 mm, 1.5 mm, 1.8 mm, 2 mm, 2.2 mm, 2.5 mm, 2.8 mm, 3 mm, 3.2 mm, 3.5 mm, 3.8 mm, 4 mm, etc., preferably 0.2-0.8 mm. In some embodiments, the coating comprises at least two coating layers, such as two layers, three layers, four layers, five layers, six layers, etc.

In some embodiments, the elastic sheet has a sustained release period of 3-90 days, such as 3 days, 10 days, 20 days, 30 days, 40 days, 50 days, 60 days, 70 days, 80 days, 90 days, etc. In some embodiments, the elastic sheet has a shape of an inverted trapezoid. In some embodiments, the inverted trapezoid has a height of 25-35 mm (such as 25 mm, 26 mm, 27 mm, 28 mm, 29 mm, 30 mm, 31 mm, 32 mm, 33 mm, 34 mm, 35 mm, etc.), an upper bottom of 20-40 mm (such as 20 mm, 22 mm, 25 mm, 27 mm, 30 mm, 32 mm, 35 mm, 37 mm, 40 mm, etc.), and a lower bottom of 5-15 mm (such as 5 mm, 6 mm, 7 mm, 8 mm, 9 mm, 10 mm, 11 mm, 12 mm, 13 mm, 14 mm, 15 mm, etc.).

The elastic sheet may have an inverted trapezoidal shape. After the implantation, the trapezoidal long bottom is located at the uterine fundus, and the trapezoidal short bottom is located at the cervix opening. In the stretched state after the implantation, the shape of the elastic sheet is adapted to the physiological shape and size of the uterus to isolate the anterior and posterior walls of the uterus as completely as possible, so that the contact between the anterior and posterior walls of the uterus is minimized. During the implantation, a conventional device is enough for the doctor to put the elastic sheet into the uterus. It should be understood that the elastic sheet can be contracted into a cylindrical shape by the doctor if necessary. The contracted elastic sheet can be delivery through the cervical canal into the uterus by a tube, and then be stretched after the implantation. In particular, the silicone rubber with an elastic modulus of 1.2-1.5 MPa is beneficial to the contraction to provide the curled state of the elastic sheet during the delivery. In addition, the elastic characteristic of the silicone rubber provides for automatic stretch in the uterine cavity to the maximum extent, and the re-curl or re-contraction caused by the movement of the uterine cavity is prevented, the isolation of the anterior wall from the posterior wall of the uterus is maximize.

Another object of the present disclosure is to provide a method forming the elastic sheet. The method comprises of mixing a drug with a controlled release factor to form a mixed solution; and spraying the mixed solution onto an outer surface of a silicone rubber to form the elastic sheet.

In some embodiments, the drug and the controlled release factor are co-dissolved or uniformly dispersed in a solvent to form a uniform solution, and the solution is atomized into uniform mixed liquid particles by an atomized device. The particle size of the mixed liquid particles after atomization is uniform, which can be sprayed on the surface of the prefabricated silicone rubber in a wet or semi-dry state, wherein the coating is formed by the crosslink between the controlled release factors or between the controlled release factor and the surface of the silicone rubber. In some embodiments, the atomized particles have a diameter of 50 nm-500 µm, preferably 10 µm-500 µm. The atomized particles are uniform in size, which is beneficial to the drug release control.

The wet or semi-dry state according to the present disclosure refers to the state of the mixed liquid particles after atomization, and the atomized mixed liquid particles can be dried by any one or at least two of natural volatilization, air drying, and heat drying. The crosslink of the present disclosure includes chemical crosslink and physical crosslink. The chemical crosslink comprises but not limited to condensation polymerization crosslink, addition polymerization crosslink, etc. The physical crosslink comprises but not limited to photo-crosslink, thermal crosslink, radiation crosslink, natural crosslink, etc.

In some embodiments, when the drug coating layer is one layer, the elastic sheet is formed by the above method, and the elastic sheet can be used for the treatment of the overall uterine cavity trauma, and can also be used for the treatment of the local uterine cavity trauma. Namely, the uterine cavity can be treated as a whole by the overall spraying coating or treated locally according to the local trauma by the local spraying coating. For example, two different drugs are carried on two sides of the elastic sheet to treat different damages.

In some embodiments, when the coating has two layers, different drugs can be selected by spraying in an overlapping manner. Namely, a first drug is sprayed and dried or semi-dried, and a second drug is sprayed to overlap the first drug. Thus, different drugs with different amounts or different release periods can be used and adjusted according to actual needs.

In some embodiments, the mixed solution is obtained by dissolving the drug and the controlled release factor in a solvent. In some embodiments, the solvent comprises an organic solvent. In some embodiments, the organic solvent comprises any one or at least two of dichloromethane, chloroform, acetone, isopropanol, ethanol, tetrahydrofuran, hexafluoroisopropanol, hexafluoroacetone, dimethyl sulfoxide, acetonitrile, diethyl ether, ethyl acetate, n-hexane, pyridine, toluene, benzene, dimethylformamide, n-heptane, methanol, ethylamine, lactic acid, petroleum ether, glycerin, octanoic acid, n-hexanol or cyclohexane.

In some embodiments, a concentration of the drug in the mixed solution is 0.1%-50%, such as 0.1%, 5%, 10%, 15%, 20%, 25%, 30%, 35%, 40%, 45%, 50%, etc., preferably 5%-30%. In some embodiments, a concentration of the controlled release factor in the mixed solution is 0.1%-50%, such as 0.1%, 5%, 10%, 15%, 20%, 25%, 30%, 35%, 40%, 45%, 50%, etc., preferably 5%-30%. In some embodiments, the mixed solution is atomized into particles having a particle diameter of 50 nm-500 μm by an atomizing device and then sprayed on the surface of the silicone rubber. The drug and the controlled release factor are initially mixed uniformly during the dissolution or dispersion of the solvent, and are further homogenized during the atomization process. Thus, the drug can be uniformly released from the elastic sheet to achieve uniform administration to the lesion site to reduce complications.

Yet another object of the present disclosure is to provide an application method for the elastic sheet in a drug sustained release system. In some embodiments, the drug sustained release system refers to a device made of a drug and a carrier or a medium, which enables the drug to be released in a designed dose and in a controlled manner, in order to treat a certain disease or improve the immunity of the body.

The elastic sheet of the present disclosure provides several benefits compared with the prior art. In some embodiments, the elastic sheet comprises a silicone rubber and a coating on the surface of the silicone rubber. The elastic sheet provides a preferable therapeutic effect in a low dose. In addition, the elastic sheet provides a longer release period and preferable sustained release ability, for the treatment of uterine cavity damage. The silicone rubber has high stability and biocompatibility, and the silicone rubber has good memory elasticity to ensure good shape retention in the body. The prefabricate silicone rubber can be modified on the surface by swelling or the like. So that an adhesive force between the modified silicone rubber and the coating can be improved. The coating deforms correspondingly in case of the deformation of the elastic sheet, in order to maintain the well adhesion between the coating and the silicone rubber. Since the coating is formed by spraying, the drug can be uniformly distributed on the surface of the silicone rubber, which facilitates the uniform and stable release of the drug, in order to obtain a preferable therapeutic effect. In addition, the overall or the local damage to the uterus can be treated. The method for forming the elastic sheet is simple from readily available materials. The method is convenient for industrial large-scale production with a low cost.

Embodiment 1

The present embodiment provides an elastic sheet comprising a silicone rubber and a coating located on an outer surface of the silicone rubber. The silicone rubber is obtained by plasma-treating the surface of the prefabricated silicone rubber. The coating is formed from atomized particles with a particle diameter of 10-300 μm. The coating comprises a drug and a controlled release factor. The drug is estradiol, the controlled release factor is D-polylactic acid, and a weight ratio of the two is 10%:90%. The coating has a thickness of 0.1 mm. The content of estradiol per elastic sheet is 10 mg. The thickness of the elastic sheet is 0.5 mm. The shape of the elastic sheet is an inverted trapezoid, with a height of 30 mm, an upper bottom of 30 mm and a lower bottom of 10 mm. The elastic modulus of the elastic sheet is 1.2 MPa.

The embodiment further provides a method for forming an elastic sheet, which comprises following steps:
  i. A certain amount of HTV medical silicone rubber was weighted and hot pressed to form a prefabricated film with a thickness of 0.1 mm for use.
  ii. 100 mg of estradiol and 900 mg of PLGA (mol ratio 10:90) were dissolved in 50 ml of acetone, and the obtained drug solution was sprayed on both sides of the prefabricated film obtained in step i, and then the solvent was evaporated (i.e., the solvent was removed by evaporation drying) to form the elastic sheet.

The content of the estradiol per elastic sheet was calculated to 10 mg according to the weight gain of the elastic sheet, wherein the content of drug per elastic sheet=the weight gain of the elastic sheet×(the drug weight in the drug solution)/(the drug weight in the drug solution+the controlled release factor weight in the drug solution)). The sample was dissolved in PBS solution at 37° C. on a drug dissolution tester, and the dissolution content was measured by HPLC. The result showed that within 30 days, the maximum amount of drug dissolution was 309 μg/d in the first 7 days, and then the drug dissolution was gradually stabilized, wherein the average drug release in 30 days was 267 μg/d.

The New Zealand rabbits were tested. Before the implantation, 6 trauma models were obtained by surgical curettage and divided into two groups A and B. The group A was given the same dose per weight of estradiol by oral, and the group B was implanted the suitable size of the elastic sheet of the present embodiment without oral estradiol. After 30 days, different degrees of adhesions happened in the uteri of the test animals in group A, but there was no adhesion happened in the uteri of the test animals in group B.

Comparative Example 1

The present example provides a matrix-type elastic sheet comprising a silicone rubber and a drug uniformly dispersed inside the silicone rubber. The drug is estradiol with a mesh number of 3000. The content of estradiol per elastic sheet is 25 mg. The thickness of the elastic sheet is 0.5 mm. The shape of the elastic sheet is an inverted trapezoid, with a height of 30 mm, an upper bottom of 30 mm and a lower bottom of 10 mm.

The example further provides a method for forming a matrix-type elastic sheet, which comprises following steps:
1 g of 17β estradiol, 30 g of HTV medical silicone rubber (molecular weight 20-100 million), 10 g of silica, 5 g of hydroxy silicone oil, 6 g of medical barium sulfate, 0.5 g of iron oxide red, and 2 g of benzoyl peroxide were kneaded to a uniform on a rubber mixer, and hot pressed on a flat vulcanizer to form a sheet having a thickness of 0.5 mm, and then cut into a desired shape to obtain a matrix-type elastic sheet.

The content of estradiol per elastic sheet was calculated to 25 mg according to the volume of the matrix-type elastic sheet. The sample was dissolved in PBS solution at 37° C. on a drug dissolution tester, and the dissolution content was measured by HPLC. The result showed that within 30 days, the maximum amount of drug dissolution was 427 µg/d in the first 3 days, and then the drug dissolution was gradually stabilized, wherein the average drug release in 30 days was 218 µg/d.

The New Zealand rabbits were tested. Before the implantation, 6 trauma models were obtained by surgical curettage and divided into two groups A and B. The group A was given the same dose per weight of estradiol by oral, and the group B was implanted the suitable size of the elastic sheet of the present embodiment without oral estradiol. After 30 days, different degrees of adhesions happened in the uteri of the test animals in group A, but there was no adhesion happened in the uteri of the test animals in group B, wherein the endometrial in group B grew well with mild and visible surgical trace.

Figure 54:
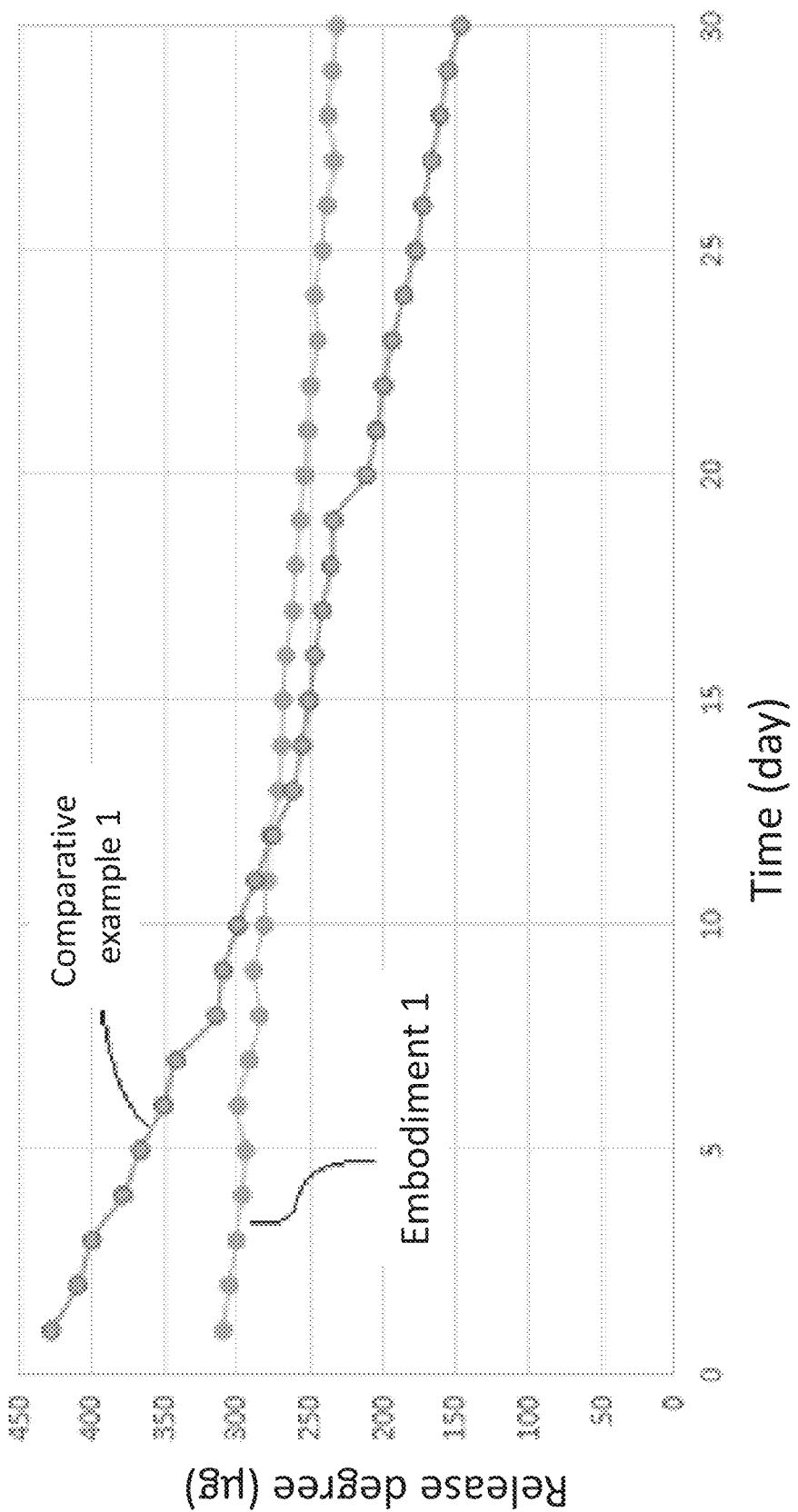
FIG. 54 shows the comparison of the 30-day drug release curve in vitro after the implantation of the elastic sheets of Embodiment 1 and Comparative example 1.

FIG. 54 shows the comparison of the 30-day drug release curve in vitro after the implantation of the elastic sheets of Embodiment 1 and Comparative example 1. Compared with Comparative example 1, the Embodiment 1 provides a stable and uniform drug release without the sudden release in the early stage of the matrix-type elastic sheet. The required drug amount of the elastic sheet is less than the matrix-type elastic sheet, and there is no significant requirement for the particle diameter of the drug.

Embodiment 2

The only difference from the Embedment 1 lies in the micronization of the estradiol with a mesh number of 2000.

The sample was dissolved in PBS solution at 37° C. on a drug dissolution tester, and the dissolution content was measured by HPLC. The result showed that within 30 days, the maximum amount of drug dissolution was 317 µg/d in the first 7 days, and then the drug dissolution was gradually stabilized, wherein the average drug release in 30 days was 276 µg/d.

Figure 55:
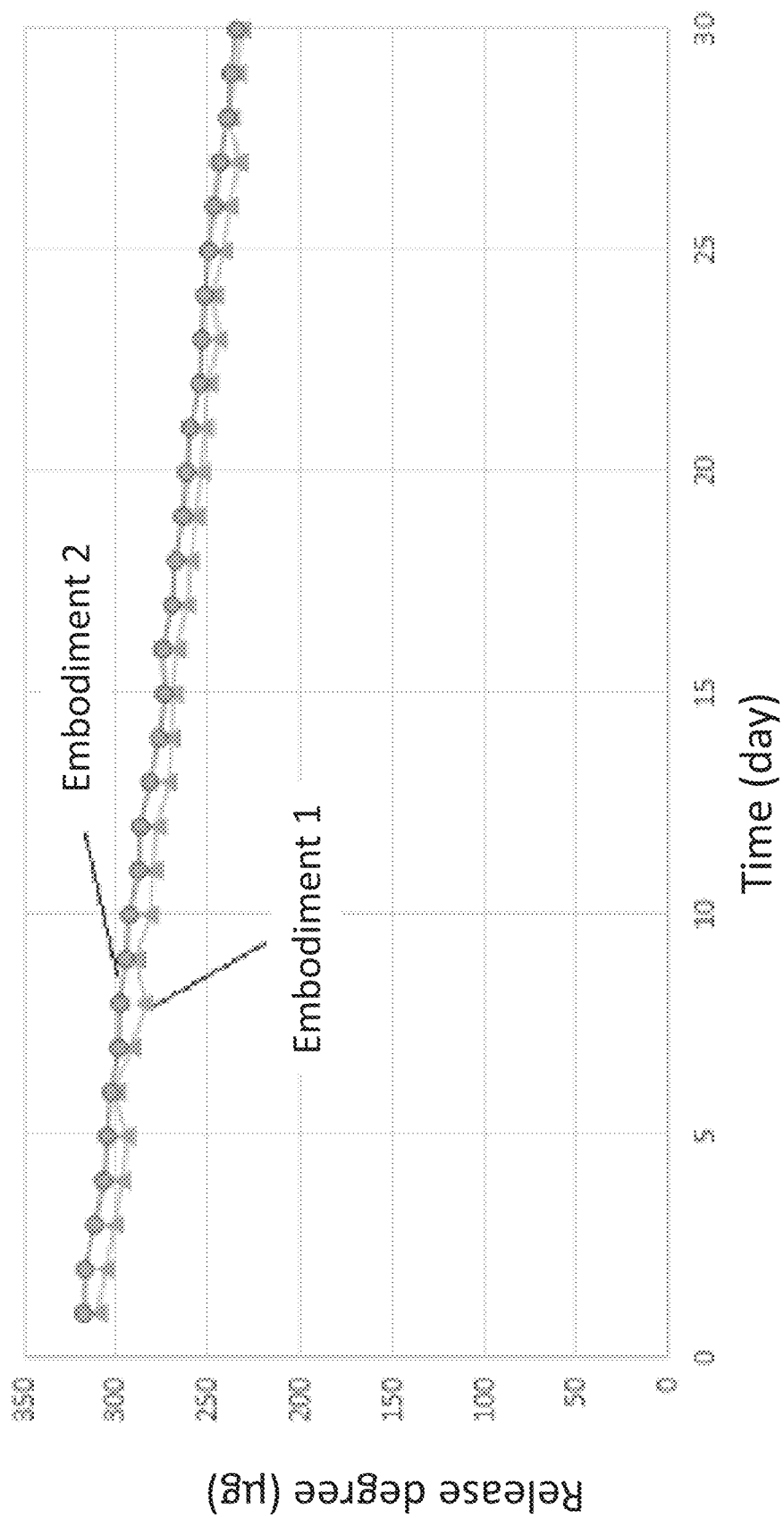
FIG. 55 shows the comparison of the 30-day drug release curve in vitro after the implantation of the elastic sheets of Embodiment 1 and Embodiment 2.

FIG. 55 shows the comparison of the 30-day drug release curve in vitro after the implantation of the elastic sheets of Embodiment 1 and Embodiment 2.

Embodiment 3

The present embodiment provides an elastic sheet comprising a silicone rubber and a coating located on an outer surface of the silicone rubber. The silicone rubber is obtained by isopropyl alcohol wiping and swelling the surface of the prefabricated silicone rubber. The coating is formed from atomized particles with a particle diameter of 10-300 µm. The coating comprises a drug and a controlled release factor. The drug is estradiol, the controlled release factor is D-polylactic acid, and a weight ratio of the two is 28%:72%. The coating has a thickness of 0.2 mm. The content of estradiol per elastic sheet is 20 mg. The thickness of the elastic sheet is 0.1 mm. The shape of the elastic sheet is an inverted trapezoid, with a height of 25 mm, an upper bottom of 20 mm and a lower bottom of 5 mm. The elastic modulus of the elastic sheet is 1.2 MPa.

The embodiment further provides a method for forming an elastic sheet, which comprises following steps:
 i. A certain amount of HTV medical silicone rubber was weighted and hot pressed to form a prefabricated film with a thickness of 0.1 mm for use.
 ii. 200 mg of estradiol and 500 mg of PLGA were dissolved in 50 ml of acetone, and the obtained drug solution was sprayed on both sides of the prefabricated film obtained in step i, and then the solvent was evaporated to form the elastic sheet.

The content of the estradiol per elastic sheet was calculated to 20 mg according to the weight gain of the elastic sheet. The sample was dissolved in PBS solution at 37° C. on a drug dissolution tester, and the dissolution content was measured by HPLC. The result showed that within 60 days, the maximum amount of drug dissolution was 472 µg/d in the first 7 days, and then the drug dissolution was gradually stabilized, wherein the average drug release in 60 days was 391 µg/d.

The New Zealand rabbits were tested. Before the implantation, 6 trauma models were obtained by surgical curettage and divided into two groups A and B. The group A was given the same dose per weight of estradiol by oral, and the group B was implanted the suitable size of the elastic sheet of the present embodiment without oral estradiol. After 60 days, different degrees of adhesions happened in the uteri of the test animals in group A, but there was no adhesion happened in the uteri of the test animals in group B.

Comparative Example 2

The present example provides an elastic sheet comprising a silicone rubber and a drug dispersed inside the silicone rubber. The drug is estradiol with a mesh number of 5000. The content of estradiol per elastic sheet is 100 mg.

The example further provides a method for forming an elastic sheet, which comprises following steps: 5 g of estradiol, 30 g of HTV medical silicone rubber, 10 g of silica, 5 g of hydroxy silicone oil, 6 g of medical barium sulfate, 0.5 g of iron oxide red, and 2 g of benzoyl peroxide were kneaded to a uniform on a rubber mixer, and hot pressed on a flat vulcanizer to form a sheet having a thickness of 0.2 mm, and then cut into a desired shape to obtain an elastic sheet.

The content of estradiol per elastic sheet was calculated to 100 mg according to the volume of the elastic sheet. The sample was dissolved in PBS solution at 37° C. on a drug dissolution tester, and the dissolution content was measured by HPLC. The result showed that within 60 days, the maximum amount of drug dissolution was 903 µg/d in the first 3 days, and then the drug dissolution was gradually stabilized, wherein the average drug release in 60 days was 333 µg/d.

The New Zealand rabbits were tested. Before the implantation, 6 trauma models were obtained by surgical curettage and divided into two groups A and B. The group A was given the same dose per weight of estradiol by oral, and the group B was implanted the suitable size of the elastic sheet of the present embodiment without oral estradiol. After 60 days, different degrees of adhesions happened in the uteri of the test animals in group A, but there was no adhesion happened in the uteri of the test animals in group B, wherein the endometrial in group B grew well.

Figure 56:
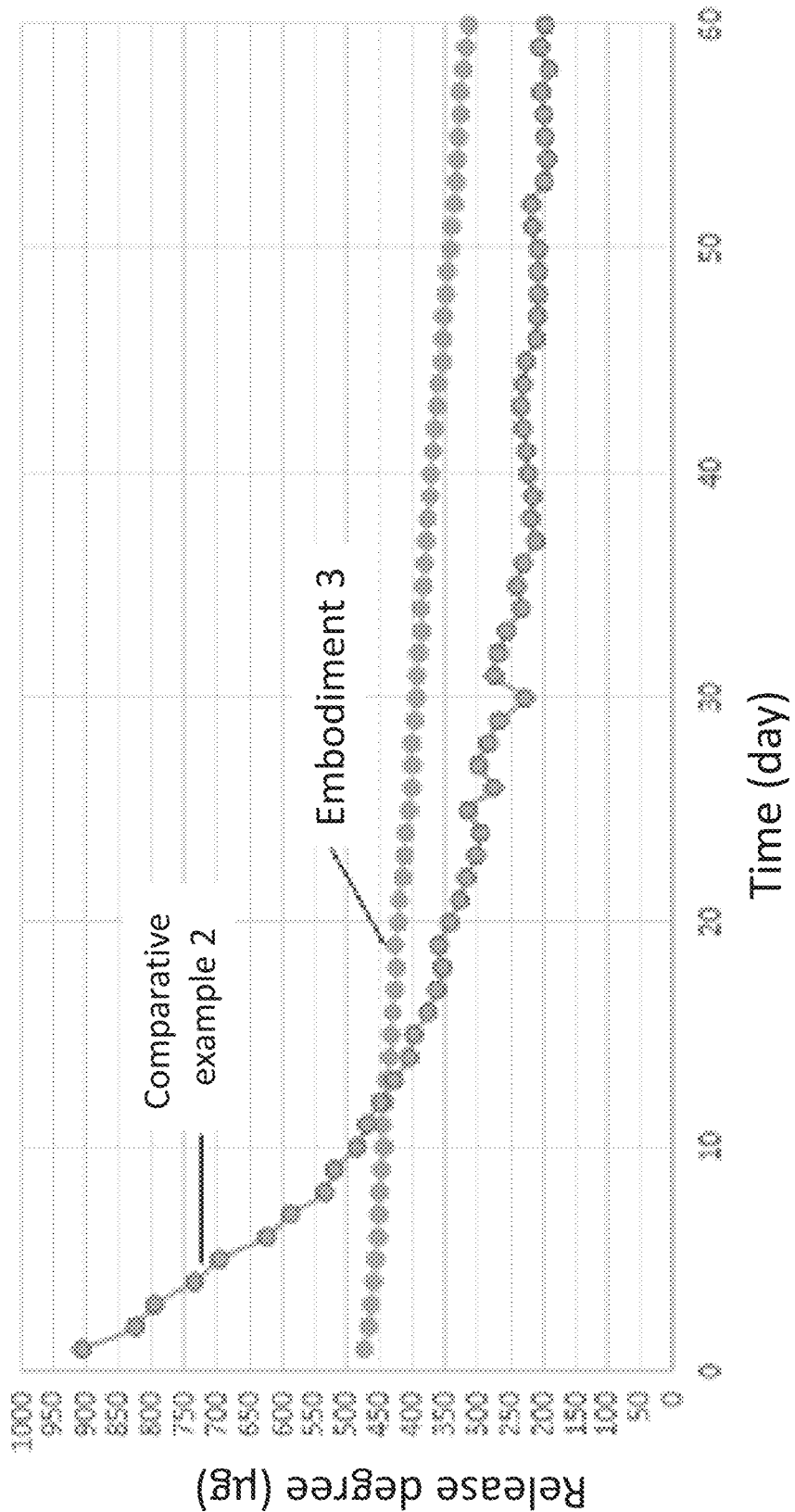
FIG. 56 shows the comparison of the 60-day drug release curve in vitro after the implantation of the elastic sheets of Embodiment 3 and Comparative example 2.

FIG. 56 shows the comparison of the 60-day drug release curve in vitro after the implantation of the elastic sheets of Embodiment 3 and Comparative example 2. Compared with Comparative example 2, the Embodiment 3 provides a stable and uniform drug release without the sudden release in the early stage of the elastic sheet. The required drug amount of the elastic sheet is less, and there is no significant requirement for the particle diameter of the drug.

Embodiment 4

The present embodiment provides an elastic sheet comprising a silicone rubber and a coating located on an outer surface of the silicone rubber. The silicone rubber is obtained by isopropyl alcohol wiping and swelling the surface of the prefabricated silicone rubber. The coating is formed from atomized particles with a particle diameter of 10-300 μm. The coating comprises a drug and a controlled release factor. The drug is estradiol and Vitamin E, the controlled release factor is D-polylactic acid, and a weight ratio of the two is 12%:88%. The coating has a thickness of 0.08 mm. The content of estradiol per elastic sheet is 10 mg, and the content of Vitamin E per elastic sheet is 2 mg. The thickness of the elastic sheet is 0.2 mm. The shape of the elastic sheet is an inverted trapezoid, with a height of 35 mm, an upper bottom of 40 mm and a lower bottom of 15 mm. The elastic modulus of the elastic sheet is 0.9 MPa.

The embodiment further provides a method for forming an elastic sheet, which comprises following steps:
i. A certain amount of HTV medical silicone rubber was weighted and hot pressed to form a prefabricated film with a thickness of 0.1 mm for use.
ii. 100 mg of estradiol, 20 mg Vitamin E and 900 mg of D-polylactic acid were dissolved in 50 ml of acetone, and the obtained drug solution was sprayed on both sides of the prefabricated film obtained in step i, and then the solvent was evaporated to form the elastic sheet.

The content of the estradiol per elastic sheet was calculated to 10 mg according to the weight gain of the elastic sheet. The sample was dissolved in PBS solution at 37° C. on a drug dissolution tester, and the dissolution content was measured by HPLC. The result showed that within 30 days, the maximum amount of estradiol dissolution was 379 μg/d, and the maximum amount of Vitamin E dissolution was 146 μg/d in the first 3 days, and then the drug dissolution was gradually stabilized, wherein the average estradiol release in 30 days was 294 μg/d, and the average Vitamin E release in 30 days was 116 μg/d.

The New Zealand rabbits were tested. Before the implantation, 6 trauma models were obtained by surgical curettage and divided into two groups A and B. The group A was given the same dose per weight of estradiol by oral, and the group B was implanted the suitable size of the elastic sheet of the present embodiment without oral estradiol. After 30 days, different degrees of adhesions happened in the uteri of the test animals in group A, but there was no adhesion happened in the uteri of the test animals in group B.

Embodiment 5

The present embodiment provides an elastic sheet comprising a modified silicone rubber and a coating located on an outer surface of the modified silicone rubber. The modified silicone rubber is obtained by plasma-treating the surface of the prefabricated silicone rubber. The coating is formed from atomized particles with a particle diameter of 10-300 μm. The coating comprises a drug and a controlled release factor. The drug is estradiol and aspirin, the controlled release factor is polylactic acid, and a weight ratio of the two is 15%:85%. The coating has a thickness of 0.2 mm. The elastic sheet coating comprises a first coating layer containing estradiol and a second coating layer containing aspirin. The content of estradiol per elastic sheet is 10 mg, and the content of aspirin per elastic sheet is 5 mg. The thickness of the elastic sheet is 0.6 mm. The shape of the elastic sheet is an inverted trapezoid, with a height of 30 mm, an upper bottom of 30 mm and a lower bottom of 10 mm. The elastic modulus of the elastic sheet is 1.5 MPa.

The embodiment further provides a method for forming an elastic sheet, which comprises following steps:
i. A certain amount of HTV medical silicone rubber was weighted and hot pressed to form a prefabricated film with a thickness of 0.2 mm for use.
ii. 50 mg of aspirin and 900 mg of polylactic acid were dissolved in 50 ml of acetone, and the obtained drug solution was sprayed on both sides of the prefabricated film obtained in step i, and then the solvent was evaporated to form the elastic sheet with a first coating layer.
iii. 100 mg of estradiol and 900 mg of polylactic acid were dissolved in 50 ml of acetone, and the obtained drug solution was sprayed on both sides of the elastic sheet with a first coating layer obtained in step ii, and then the solvent was evaporated to form the elastic sheet with a second coating layer.

The content of the estradiol per elastic sheet was calculated to 10 mg and the content of the aspirin was calculated to 5 mg according to the weight gain of the elastic sheet. The sample was dissolved in PBS solution at 37° C. on a drug dissolution tester, and the dissolution content was measured by HPLC. The result showed that within 30 days the average estradiol release was 372 μg/d and the average aspirin release was 0 μg/d; within the following 30 days, the average estradiol release was 31 μg/d and the average aspirin release was 172 μg/d.

The New Zealand rabbits were tested. Before the implantation, 6 trauma models were obtained by surgical curettage and divided into two groups A and B. The group A was given the same dose per weight of estradiol by oral, and the group B was implanted the suitable size of the elastic sheet of the present embodiment without oral estradiol. After 30 days, different degrees of adhesions happened in the uteri of the test animals in group A, but there was no adhesion happened in the uteri of the test animals in group B.

Comparative Example 3

The only difference from the Embedment 1 lies in the prefabricated silicone rubber without plasma-treating.

After spraying, about 10% of the coating of the curled elastic sheet is shed. That is to say, the coating is insecure enough, and the loaded amount and release of the drug would be affected.

Obviously, compared with Embedment 1, no surface treatment of the prefabricated silicone rubber may result in the coating shedding.

Comparative Example 4

The only difference from the Embedment 1 lies in the atomized particles forming the coating with a particle diameter above 500 μm.

The sample was dissolved in PBS solution at 37° C. on a drug dissolution tester, and the dissolution content was measured by HPLC. The result showed that the average estradiol release was 593 µg/d in 20 days, and the average estradiol release was 26 µg/d in following 10 days.

Compared with Embedment 1, the drug is released faster if the atomized particles forming the coating with a bigger particle diameter.

Since the existing equipment provides atomized particles with a minimum particle diameter of about 50 nm, and particles with a too small diameter cause great damage to the equipment and high failure rate, it is not recommended to spray particles with the size below 50 nm.

1. An elastic sheet, comprising: a silicone rubber; and a drug; wherein the drug is carried by an outer surface of the silicone rubber as a coating, and the drug comprises an estrogen.
2. The elastic sheet according to the claim 1, wherein the drug is atomized to particles which are sprayed onto the outer surface of the silicone rubber; preferably, the silicone rubber is obtained by treating a surface of a prefabricated silicone rubber; preferably, the treating comprises any one or at least two of a plasma treatment, a swelling treatment, a sandblasting treatment, a sanding treatment, a texture treatment, an electrostatic treatment or a wetting treatment; preferably, the drug is atomized to particles with a particle diameter of 50 nm-500 µm which are sprayed onto the outer surface of the silicone rubber.
3. The elastic sheet according to the claim 1, wherein the coating comprises a drug and a controlled release factor; preferably, a weight ratio of the drug to the controlled release factor is (10%-90%):(90%-10%); preferably, the coating has a thickness of 0.02-0.2 mm; preferably, the controlled release factor is a degradable polymer; preferably, a weight ratio of the drug to the degradable polymer is (30%-50%):(70%-50%).
4. The elastic sheet according to the claim 1, wherein the elastic sheet has estrogen of 10 mg-200 mg; preferably, the estrogen has a daily release of 10 µm-4 mg.
5. The elastic sheet according to the claim 1, wherein the estrogen comprises any one or at least two of 17β estradiol, estrone, estriol, and estradiol derivatives; preferably, the estrogen comprises any one or at least two of estradiol benzoate, estradiol valerate, ethinyl estradiol, ethinyl estradiol, conjugated estrogens, diethylstilbestrol, nylestriol and promestriene.
6. The elastic sheet according to the claim 1, wherein the drug further comprises a drug for improving endometrial blood flow and/or a colony stimulating factor; preferably, the drug for improving endometrial blood flow comprises any one or at least two of aspirin, sildenafil citrate, pentoxifylline (PTX) and vitamin E, L-arginine, and low molecular weight heparin; preferably, the colony stimulating factor includes granulocyte colony stimulating factor (G-CSF), and/or granulocyte-macrophage colony stimulating factor (GM-CSF); preferably, a weight ratio of the estrogen to the drug for improving endometrial blood flow is 1:(0.1-1), preferably 1:(0.3-0.6); preferably, a weight ratio of the colony stimulating factor to the estrogen is (0.05-0.5):1.
7. The elastic sheet according to the claim 2, wherein the prefabricated silicone rubber comprises any one or at least two of heat vulcanized silicone rubber (HTV), room temperature vulcanized silicone rubber (RTV), low temperature vulcanized silicone rubber (LTV), DOWCORNING Silastic-382 medical silicone rubber, and DOWCORNING Q7 medical silicone rubber series and implantable MDX series; preferably, the elastic sheet has an elastic modulus of 0.5-3 MPa, preferably 1.0-2.0 MPa.
8. The elastic sheet according to the claim 1, wherein the elastic sheet has a thickness of 0.1-4 mm, preferably 0.2-0.8 mm; preferably, the coating comprises at least two coating layers; preferably, the elastic sheet has a sustained release period of 3-90 days; preferably, the elastic sheet has a shape of an inverted trapezoid; preferably, the inverted trapezoid has a height of 25-35 mm, an upper bottom of 20-40 mm, and a lower bottom of 5-15 mm.
9. A method for forming the elastic sheet according to claim 1, comprising of: mixing a drug with a controlled release factor to form a mixed solution; and spraying the mixed solution onto an outer surface of a silicone rubber to form the elastic sheet; preferably, the mixed solution is obtained by dissolving the drug and the controlled release factor in a solvent; preferably, the solvent comprises an organic solvent; preferably, the organic solvent comprises any one or at least two of dichloromethane, chloroform, acetone, isopropanol, ethanol, tetrahydrofuran, hexafluoroisopropanol, hexafluoroacetone, dimethyl sulfoxide, acetonitrile, diethyl ether, ethyl acetate, n-hexane, pyridine, toluene, benzene, dimethylformamide, n-heptane, methanol, ethylamine, lactic acid, petroleum ether, glycerin, octanoic acid, n-hexanol or cyclohexane; preferably, a concentration of the drug in the mixed solution is 0.1%-50%, preferably 5%-30%; preferably, a concentration of the controlled release factor in the mixed solution is 0.1%-50%, preferably 5%-30%; preferably, the mixed solution is atomized into particles having a particle diameter of 50 nm-500 µm by an atomizing device and then sprayed on the surface of the silicone rubber.

The above embodiments of the present disclosure are not intended to limit the scope of the present invention, and the invention may be practiced otherwise than as specifically described. That is to say, the simple and equivalent changes and modifications are possible in light of the above teaching and fall within the scope of the appended claims. The conventional technical contents are not described in detail. The foregoing description is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An insertable device with a function of re-activating an endometrial basal layer in a uterine cavity, the insertable device comprising:
    an elastic membrane including a silicone rubber and a drug;
    an intervening wire; and
    a thin tube,
    wherein the drug comprises an estrogen, and the drug is encased in at least one of: a drug storage zone within the silicone rubber, uniformly dispersed inside the silicone rubber, or as a coating on an outer surface of the silicone rubber, wherein the elastic membrane has an inverted trapezoidal structure to isolate an anterior wall from a posterior wall of the uterine cavity, wherein the elastic membrane has at least two connecting through-holes, the at least two connecting through-holes including a first connecting through-hole and a second connecting through-hole, wherein the intervening wire passes through the first connecting through-hole and the second connecting through-hole in sequence, wherein the intervening wire has two free ends that are combined and fixed together, a part of the intervening wire between the first connecting through-hole and the second connecting through-hole is a non-free end portion of the intervening wire, the non-free end portion of the intervening wire is sleeved with the thin tube, wherein an entire length of the thin tube contacts the elastic membrane and exerts mutual interaction forces with the elastic membrane during a force application process, causing the thin tube to distribute the mutual interaction forces, and thereby reducing a cutting force of the intervening wire on the elastic membrane.

2. The insertable device according to claim 1, wherein the inverted trapezoidal structure of the elastic membrane includes a short side and a long side, and wherein the short side of the elastic membrane defines a lower base, the long side of the elastic membrane defines an upper base, and a vertical distance from the first connecting through-hole to the lower base of the elastic membrane in a direction perpendicular to the lower base is not more than 8 mm.

3. The insertable device according to claim 2, wherein the vertical distance from the first connecting through-hole to the lower base of the elastic membrane in the direction perpendicular to the lower base is not more than 1 mm.

4. The insertable device according to claim 1, wherein the at least two connecting through-holes includes three connecting through-holes, the three connecting through-holes including a first connecting through-hole, a second connecting through-hole, and a third connecting through-hole, the first connecting through-hole and the second connecting through-hole are located above the third connecting through-hole, the free ends of the intervening wire pass through the first connecting through-hole and the second connecting through-hole, respectively, and then pass through the third connecting through-hole after following an outer contour line of the elastic membrane.

5. The insertable device according to claim 4, wherein the two free ends of the intervening wire pass through the first connecting through-hole and the second connecting through-hole on a front side of the elastic membrane, respectively, and are combined and fixed after passing through the third connecting through-hole from a back side of the elastic membrane, opposite the front side of the elastic membrane.

6. The insertable device according to claim 4, wherein the two free ends of the intervening wire pass through the first connecting through-hole and the second connecting through-hole on a front side of the elastic membrane, respectively, and then pass through the third connecting through-hole after being combined on the front side of the elastic membrane.

7. The insertable device according to claim 1, wherein the elastic membrane has a thickness of 0.1-4 mm.

8. The insertable device according to claim 1, wherein the inverted trapezoidal structure of the elastic membrane includes a short side and a long side, and wherein the short side of the elastic membrane defines a lower base having a length of 5-15 mm, the long side of the elastic membrane defines an upper base having a length of 20-40 mm, and wherein the inverted trapezoidal structure of the elastic membrane defines a height of 25-35 mm between the upper base and the lower base.

9. The insertable device according to claim 1, wherein the at least two connecting through-holes each have a circular shape with a diameter of 0.3-1.2 mm, and wherein the diameters of the at least two connecting through-holes are each greater than a diameter of the intervening wire.

10. The insertable device according to claim 1, wherein the thin tube is an elastic tube, or the thin tube is a silicone tube.

11. The insertable device according to claim 1, wherein the inverted trapezoidal structure of the elastic membrane includes a short side and a long side, wherein the short side of the elastic membrane defines a lower base, and wherein a vertical distance from the at least two connecting through-holes to the lower base of the elastic membrane is at least 0.5 mm.

12. The insertable device according to claim 11, wherein the vertical distance from the at least two connecting through-holes to the lower base of the elastic membrane is at least 4 mm.

13. The insertable device according to claim 1, wherein the inverted trapezoidal structure of the elastic membrane includes a short side and a long side, and wherein the short side of the elastic membrane defines a lower base, the long side of the elastic membrane defines an upper base, and wherein any two connecting through-holes of the at least two connecting through-holes are separated by a horizontal distance perpendicular to the lower base and which is not more than 10 mm.

14. The insertable device according to claim 13, wherein the horizontal distance perpendicular to the lower base between the any two connecting through-holes is not more than 2 mm.

15. The insertable device according to claim 1, wherein the elastic membrane further includes two fixing through-holes, wherein the two fixing through-holes are configured to receive another intervening wire for attaching the elastic membrane to a delivery device.

16. A system for preventing intrauterine adhesion, the system comprising: the insertable device according to claim 1, and a delivery device for delivering the insertable device into the uterine cavity.

* * * * *

UNITED STATES PATENT AND TRADEMARK OFFICE
CERTIFICATE OF CORRECTION

Page 1 of 1

PATENT NO. : 12,427,106 B2
APPLICATION NO. : 16/445939
DATED : September 30, 2025
INVENTOR(S) : Peipei Xia et al.

It is certified that error appears in the above-identified patent and that said Letters Patent is hereby corrected as shown below:

On the Title Page

The following foreign priority data should be added:
(30) Foreign Application Priority Data
April 4, 2019 (CN)................201910270119.3
April 4, 2019 (CN)................201910270128.2
April 4, 2019 (CN)................201910270137.1

Signed and Sealed this
Twentieth Day of January, 2026

John A. Squires
*Director of the United States Patent and Trademark Office*